US008916581B2

(12) United States Patent  
Boyd et al.

(10) Patent No.: US 8,916,581 B2
(45) Date of Patent: *Dec. 23, 2014

(54) (S)-N-METHYLNALTREXONE

(75) Inventors: Thomas A. Boyd, Grandview, NY (US); Howard Wagoner, Warwick, NY (US); Suketu P. Sanghvi, Kendall Park, NJ (US); Christopher Verbicky, Broadalbin, NY (US); Stephen Andruski, Clifton Park, NY (US)

(73) Assignee: Progenics Pharmaceuticals, Inc., Tarrytown, NY (US)

( * ) Notice: Subject to any disclaimer, the term of this patent is extended or adjusted under 35 U.S.C. 154(b) by 344 days.

This patent is subject to a terminal disclaimer.

(21) Appl. No.: 13/167,348

(22) Filed: Jun. 23, 2011

(65) Prior Publication Data

US 2012/0136019 A1 May 31, 2012

Related U.S. Application Data

(60) Continuation of application No. 12/460,507, filed on Jul. 20, 2009, now Pat. No. 8,003,794, which is a division of application No. 11/441,452, filed on May 25, 2006, now Pat. No. 7,563,899.

(60) Provisional application No. 60/684,570, filed on May 25, 2005.

(51) Int. Cl.
*A61K 31/485* (2006.01)
*C07D 489/08* (2006.01)

(52) U.S. Cl.
CPC ................................ *C07D 489/08* (2013.01)
USPC ............................................ 514/282; 546/45

(58) Field of Classification Search
USPC ............................................ 514/282; 546/45
See application file for complete search history.

(56) References Cited

U.S. PATENT DOCUMENTS

| | | | |
|---|---|---|---|
| 3,714,159 A | 1/1973 | Janssen et al. | |
| 3,723,440 A | 3/1973 | Freter et al. | |
| 3,854,480 A | 12/1974 | Zaffaroni | |
| 3,884,916 A | 5/1975 | Janssen et al. | |
| 3,937,801 A | 2/1976 | Lippmann | |
| 3,996,214 A | 12/1976 | Dajani et al. | |
| 4,012,393 A | 3/1977 | Markos et al. | |
| 4,013,668 A | 3/1977 | Adelstein et al. | |
| 4,025,652 A | 5/1977 | Diamond et al. | |
| 4,060,635 A | 11/1977 | Diamond et al. | |
| 4,066,654 A | 1/1978 | Adelstein et al. | |
| 4,069,223 A | 1/1978 | Adelstein | |
| 4,072,686 A | 2/1978 | Adelstein et al. | |
| 4,115,400 A | 9/1978 | Zimmerman | |
| 4,115,564 A | 9/1978 | Diamond et al. | |
| 4,116,963 A | 9/1978 | Adelstein | |
| 4,125,531 A | 11/1978 | Yen | |
| 4,176,186 A * | 11/1979 | Goldberg et al. | 514/282 |
| 4,194,045 A | 3/1980 | Adelstein | |
| 4,203,920 A | 5/1980 | Diamond et al. | |
| 4,241,066 A | 12/1980 | Kobylecki et al. | |
| 4,277,605 A | 7/1981 | Buyniski et al. | |
| 4,311,833 A | 1/1982 | Namikoshi et al. | |
| 4,322,426 A | 3/1982 | Hermann et al. | |
| 4,326,074 A | 4/1982 | Diamond et al. | |
| 4,326,075 A | 4/1982 | Diamond et al. | |
| 4,377,568 A | 3/1983 | Chopra et al. | |
| 4,385,078 A | 5/1983 | Onda et al. | |
| 4,427,676 A | 1/1984 | White et al. | |
| 4,430,327 A | 2/1984 | Frederickson et al. | |
| 4,452,775 A | 6/1984 | Kent | |
| 4,457,907 A | 7/1984 | Porter et al. | |
| 4,462,839 A | 7/1984 | McGinley et al. | |
| 4,466,968 A | 8/1984 | Bernstein | |
| 4,518,433 A | 5/1985 | McGinley et al. | |
| 4,533,739 A | 8/1985 | Pitzele et al. | |
| 4,556,552 A | 12/1985 | Porter et al. | |
| 4,606,909 A | 8/1986 | Bechgaard et al. | |
| 4,615,885 A | 10/1986 | Nakagame et al. | |
| 4,670,287 A | 6/1987 | Tsuji et al. | |
| 4,675,189 A | 6/1987 | Kent et al. | |
| 4,689,332 A | 8/1987 | McLaughlin et al. | |
| 4,719,215 A | 1/1988 | Goldberg | |
| 4,730,048 A | 3/1988 | Portoghese | |
| 4,765,978 A | 8/1988 | Abidi et al. | |
| 4,806,556 A | 2/1989 | Portoghese | |
| 4,824,853 A | 4/1989 | Wals et al. | |
| 4,836,212 A | 6/1989 | Schmitt et al. | |
| 4,837,214 A | 6/1989 | Tanaka et al. | |
| 4,857,533 A | 8/1989 | Sherman et al. | |

(Continued)

FOREIGN PATENT DOCUMENTS

AU 610 561 8/1988
AU 758 416 B2 7/1999

(Continued)

OTHER PUBLICATIONS

Internatinal Search Report and Written Opinion for PCT/US2006/020232 mailed Oct. 24, 2006.
International Preliminary Report on Patentability for PCT/US2006/020232 mailed Dec. 13, 2007.
Notice of Allowance mailed Mar. 20, 2009 for U.S. Appl. No. 11/441,452.
Office Action mailed May 1, 2008 U.S. Appl. No. 11/441,452.
[No Author Listed] Extracolonic Motility Abnormalities. Persistence of Abdominal Symptoms after Successful Surgery from Southern Medical Journal. 2002;95(9);1042-1046. http://www.medscape.com/viewarticle/442893_4, 2 pages.
[No Author Listed] Medseape General Medicine. 2005;7(3):17 http://www.medscape.com/viewarticle/506798_5, 3 pages.
[No Author Listed] Methylnaltrexone: MNTX. Drugs R D. 2006;7(6):374-8.
[No Author Listed] Oncology. 1996;10(12):1880.

(Continued)

*Primary Examiner* — Charanjit Aulakh
(74) *Attorney, Agent, or Firm* — McCarter & English, LLP; Jonathan M. Sparks; Maneesh Gulati

(57) ABSTRACT

This invention relates to S-MNTX, methods of producing S-MNTX, pharmaceutical preparations comprising S-MNTX and methods for their use.

29 Claims, 6 Drawing Sheets

(56) References Cited

U.S. PATENT DOCUMENTS

| | | |
|---|---|---|
| 4,861,781 A | 8/1989 | Goldberg |
| 4,863,928 A | 9/1989 | Atkinson et al. |
| 4,867,979 A | 9/1989 | Sheth et al. |
| 4,870,084 A | 9/1989 | Eggler et al. |
| 4,888,346 A | 12/1989 | Bihari et al. |
| 4,891,379 A | 1/1990 | Zimmerman et al. |
| 4,912,114 A | 3/1990 | Revesz |
| 4,965,269 A | 10/1990 | Brändström et al. |
| 4,987,136 A | 1/1991 | Kreek et al. |
| 4,990,521 A | 2/1991 | Van Daele et al. |
| 4,999,342 A | 3/1991 | Ahmad et al. |
| 5,102,887 A | 4/1992 | Goldberg |
| 5,116,868 A | 5/1992 | Chen et al. |
| 5,133,974 A | 7/1992 | Paradissis et al. |
| 5,159,081 A | 10/1992 | Cantrell et al. |
| 5,202,159 A | 4/1993 | Chen et al. |
| 5,220,017 A | 6/1993 | Bock et al. |
| 5,236,947 A | 8/1993 | Calvet et al. |
| 5,250,542 A | 10/1993 | Cantrell et al. |
| 5,256,154 A | 10/1993 | Liebert et al. |
| 5,270,328 A | 12/1993 | Cantrell et al. |
| 5,312,899 A | 5/1994 | Schiller |
| 5,391,372 A | 2/1995 | Campbell |
| 5,407,686 A | 4/1995 | Patel et al. |
| 5,426,112 A | 6/1995 | Zagon et al. |
| 5,434,171 A | 7/1995 | Frank et al. |
| 5,472,943 A | 12/1995 | Crain et al. |
| 5,512,578 A | 4/1996 | Crain et al. |
| 5,536,507 A | 7/1996 | Abramowitz et al. |
| 5,567,423 A | 10/1996 | Ying et al. |
| 5,585,348 A | 12/1996 | Crain et al. |
| 5,591,433 A | 1/1997 | Michael et al. |
| 5,597,564 A | 1/1997 | Ying et al. |
| 5,609,871 A | 3/1997 | Michael et al. |
| 5,614,219 A | 3/1997 | Wunderlich et al. |
| 5,614,222 A | 3/1997 | Kaplan et al. |
| 5,626,875 A | 5/1997 | Ballester Rodes et al. |
| 5,629,001 A | 5/1997 | Michael et al. |
| 5,656,290 A | 8/1997 | Kelm et al. |
| 5,686,072 A | 11/1997 | Uhr et al. |
| 5,714,586 A | 2/1998 | Kunstmann et al. |
| 5,739,152 A | 4/1998 | Andersson et al. |
| 5,767,125 A | 6/1998 | Crain et al. |
| 5,804,595 A | 9/1998 | Portoghese et al. |
| 5,811,451 A | 9/1998 | Minoia et al. |
| 5,821,219 A | 10/1998 | Grandy et al. |
| 5,866,154 A | 2/1999 | Bahal et al. |
| 5,866,164 A | 2/1999 | Kuczynski et al. |
| 5,958,452 A | 9/1999 | Oshlack et al. |
| 5,972,954 A | 10/1999 | Foss et al. |
| 5,981,185 A | 11/1999 | Matson et al. |
| RE36,547 E | 2/2000 | Crain et al. |
| 6,025,154 A | 2/2000 | Li et al. |
| 6,096,756 A | 8/2000 | Crain et al. |
| 6,096,763 A | 8/2000 | Hoffman et al. |
| 6,096,764 A | 8/2000 | Bryant et al. |
| 6,099,853 A | 8/2000 | Hertelendy et al. |
| 6,136,780 A | 10/2000 | Zagon et al. |
| 6,153,620 A | 11/2000 | Kornetsky |
| 6,190,691 B1 | 2/2001 | Mak |
| 6,194,382 B1 | 2/2001 | Crain et al. |
| 6,261,599 B1 | 7/2001 | Oshlack et al. |
| 6,274,591 B1 | 8/2001 | Foss et al. |
| 6,277,384 B1 | 8/2001 | Kaiko et al. |
| 6,353,004 B1 | 3/2002 | Farrar et al. |
| 6,359,111 B1 | 3/2002 | Meyer et al. |
| 6,362,194 B1 | 3/2002 | Crain et al. |
| 6,384,044 B1 | 5/2002 | Bihari |
| 6,395,705 B2 | 5/2002 | Crain et al. |
| 6,419,959 B1 | 7/2002 | Walter et al. |
| 6,426,094 B1 | 7/2002 | Piver et al. |
| 6,451,806 B2 | 9/2002 | Farrar |
| 6,455,537 B1 | 9/2002 | Cooper |
| 6,469,030 B2 | 10/2002 | Farrar et al. |
| 6,479,500 B1 | 11/2002 | Fukushima et al. |
| 6,559,158 B1 | 5/2003 | Foss et al. |
| 6,608,075 B2 | 8/2003 | Foss et al. |
| 6,693,125 B2 | 2/2004 | Borisy et al. |
| 6,696,066 B2 | 2/2004 | Kaiko et al. |
| 6,720,336 B2 | 4/2004 | Liras |
| 6,723,712 B2 | 4/2004 | Bourhis et al. |
| 6,734,188 B1 | 5/2004 | Rhodes et al. |
| 6,756,364 B2 | 6/2004 | Barbier et al. |
| 6,777,534 B1 | 8/2004 | Klagsbrun et al. |
| 6,794,370 B2 | 9/2004 | Achterrath |
| 6,800,639 B2 | 10/2004 | Giles et al. |
| 6,833,349 B2 | 12/2004 | Xia et al. |
| 6,838,469 B2 | 1/2005 | Sumegi |
| 6,884,879 B1 | 4/2005 | Baca et al. |
| 6,900,234 B1 | 5/2005 | Fossa |
| 6,946,556 B1 | 9/2005 | Likhotvorik et al. |
| 6,960,596 B2 | 11/2005 | Bissery |
| 6,967,016 B2 | 11/2005 | van Gemen et al. |
| 6,984,403 B2 | 1/2006 | Hagen et al. |
| 6,986,901 B2 | 1/2006 | Meisel et al. |
| 6,989,383 B2 | 1/2006 | Rosen et al. |
| 6,992,106 B2 | 1/2006 | Morinaga et al. |
| 7,012,100 B1 | 3/2006 | Edwards et al. |
| 7,074,825 B2 | 7/2006 | Mo et al. |
| 7,094,775 B2 | 8/2006 | Strugnell et al. |
| 7,129,265 B2 | 10/2006 | Mason |
| 7,132,554 B2 | 11/2006 | Rose |
| 7,141,554 B2 | 11/2006 | Rochat et al. |
| 7,160,913 B2 | 1/2007 | Schneider |
| 7,183,269 B2 | 2/2007 | Kreutz |
| 7,196,115 B2 | 3/2007 | Khanuja et al. |
| 7,259,233 B2 | 8/2007 | Dodd et al. |
| 7,501,434 B2 | 3/2009 | Shah et al. |
| 7,563,899 B2 * | 7/2009 | Boyd et al. .................. 546/45 |
| 7,674,904 B2 | 3/2010 | Doshan et al. |
| 8,003,794 B2 * | 8/2011 | Boyd et al. .................. 546/45 |
| 2001/0010919 A1 | 8/2001 | Grandy et al. |
| 2001/0018413 A1 | 8/2001 | Crain et al. |
| 2001/0033865 A1 | 10/2001 | Oshlack et al. |
| 2001/0036469 A1 | 11/2001 | Gooberman |
| 2001/0036476 A1 | 11/2001 | Oshlack et al. |
| 2001/0036951 A1 | 11/2001 | Farrar et al. |
| 2001/0046968 A1 | 11/2001 | Zagon et al. |
| 2001/0047005 A1 | 11/2001 | Farrar et al. |
| 2002/0028825 A1 | 3/2002 | Foss et al. |
| 2002/0064771 A1 | 5/2002 | Zhong et al. |
| 2002/0068712 A1 | 6/2002 | Stevens |
| 2002/0173466 A1 | 11/2002 | Crain et al. |
| 2002/0176888 A1 | 11/2002 | Bartholomaeus et al. |
| 2002/0188005 A1 | 12/2002 | Farrar et al. |
| 2003/0022909 A1 | 1/2003 | Moss et al. |
| 2003/0026801 A1 | 2/2003 | Weiner et al. |
| 2003/0039689 A1 | 2/2003 | Chen et al. |
| 2003/0065003 A1 | 4/2003 | Foss et al. |
| 2003/0105121 A1 | 6/2003 | Bihari |
| 2003/0124086 A1 | 7/2003 | Bentley et al. |
| 2003/0144312 A1 | 7/2003 | Schoenhard |
| 2003/0158220 A1 | 8/2003 | Foss et al. |
| 2003/0187010 A1 | 10/2003 | Foss et al. |
| 2003/0191147 A1 | 10/2003 | Sherman et al. |
| 2003/0219406 A1 | 11/2003 | Schroit et al. |
| 2004/0010996 A1 | 1/2004 | Karlstrom et al. |
| 2004/0010997 A1 | 1/2004 | Close |
| 2004/0010998 A1 | 1/2004 | Turco |
| 2004/0024006 A1 | 2/2004 | Simon |
| 2004/0136908 A1 | 7/2004 | Olson et al. |
| 2004/0162306 A1 | 8/2004 | Foss et al. |
| 2004/0162307 A1 | 8/2004 | Foss et al. |
| 2004/0162308 A1 | 8/2004 | Foss et al. |
| 2004/0167147 A1 | 8/2004 | Foss et al. |
| 2004/0167148 A1 | 8/2004 | Foss et al. |
| 2004/0180916 A1 | 9/2004 | Levine |
| 2004/0242523 A1 | 12/2004 | Weichselbaum et al. |
| 2004/0254156 A1 | 12/2004 | Le Bourdonnec et al. |
| 2004/0254208 A1 | 12/2004 | Weber et al. |
| 2004/0259898 A1 | 12/2004 | Moss et al. |
| 2004/0259899 A1 | 12/2004 | Sanghvi et al. |
| 2004/0266806 A1 | 12/2004 | Sanghvi et al. |
| 2005/0004029 A1 | 1/2005 | Garcia |

(56) References Cited

U.S. PATENT DOCUMENTS

| | | | |
|---|---|---|---|
| 2005/0004155 A1 | 1/2005 | Boyd et al. |
| 2005/0011468 A1 | 1/2005 | Moss et al. |
| 2005/0048117 A1 | 3/2005 | Foss et al. |
| 2005/0085514 A1 | 4/2005 | Cosford et al. |
| 2005/0124657 A1 | 6/2005 | Christ et al. |
| 2005/0124885 A1 | 6/2005 | Abend et al. |
| 2005/0187255 A1 | 8/2005 | Lee et al. |
| 2006/0025592 A1 | 2/2006 | Stranix et al. |
| 2006/0063792 A1 | 3/2006 | Dolle et al. |
| 2006/0094658 A1 | 5/2006 | Currie et al. |
| 2006/0115424 A1 | 6/2006 | Gray et al. |
| 2006/0128742 A1 | 6/2006 | Edwards et al. |
| 2006/0204512 A1 | 9/2006 | Krasnoperov et al. |
| 2006/0205753 A1 | 9/2006 | Israel |
| 2006/0258696 A1 | 11/2006 | Moss et al. |
| 2007/0010450 A1 | 1/2007 | Currie et al. |
| 2007/0020261 A1 | 1/2007 | Sliwkowski et al. |
| 2007/0060501 A1 | 3/2007 | Jhamandas et al. |
| 2007/0071761 A1 | 3/2007 | Seon |
| 2007/0082044 A1 | 4/2007 | Yeum |
| 2007/0099946 A1 | 5/2007 | Doshan et al. |
| 2007/0265293 A1 | 11/2007 | Boyd et al. |
| 2008/0064743 A1 | 3/2008 | Shah et al. |
| 2008/0064744 A1 | 3/2008 | Shah et al. |
| 2008/0070975 A1 | 3/2008 | Shah et al. |
| 2008/0075771 A1 | 3/2008 | Vaughn et al. |
| 2008/0103438 A1 | 5/2008 | Prais et al. |
| 2008/0194611 A1 | 8/2008 | Alverdy et al. |
| 2008/0274119 A1 | 11/2008 | Moss et al. |
| 2009/0312359 A1 | 12/2009 | Foss et al. |
| 2010/0087472 A1 | 4/2010 | Foss et al. |
| 2010/0099699 A1 | 4/2010 | Melucci et al. |
| 2010/0105911 A1 | 4/2010 | Wagoner et al. |
| 2010/0120813 A1 | 5/2010 | Bazhina et al. |

FOREIGN PATENT DOCUMENTS

| | | |
|---|---|---|
| AU | 2003204844 B2 | 9/2007 |
| BE | 876 968 A1 | 10/1979 |
| CA | 2 064 373 A1 | 9/1992 |
| CA | 1 315 689 | 4/1993 |
| CA | 2 312 234 | 5/1999 |
| DE | 3 780 819 T2 | 1/1993 |
| DE | 4 303 214 A1 | 8/1994 |
| DE | 196 51 551 A1 | 6/1998 |
| EP | 0 278 821 A1 | 8/1988 |
| EP | 0 289 070 A1 | 11/1988 |
| EP | 0 306 575 B1 | 3/1989 |
| EP | 0 352 361 A1 | 1/1990 |
| EP | 0 506 468 A1 | 9/1992 |
| EP | 0 643 967 A2 | 3/1995 |
| EP | 0 663 401 A1 | 7/1995 |
| EP | 0 760 661 B1 | 12/1998 |
| EP | 1 047 726 A1 | 7/1999 |
| EP | 0 984 004 a2 | 3/2000 |
| ES | 2226933 T3 | 4/2005 |
| GB | 1 202 148 | 8/1970 |
| JP | 1 068 376 A | 3/1989 |
| JP | 2-25427 | 1/1990 |
| JP | 4-183371 | 6/1992 |
| JP | 4-225922 A | 8/1992 |
| JP | 5-213763 | 8/1993 |
| JP | 2 625 457 B2 | 7/1997 |
| JP | 4-217924 B2 | 2/2009 |
| NZ | 222911 | 12/1987 |
| SG | 116167 | 1/2008 |
| WO | WO 83/03197 A1 | 9/1983 |
| WO | WO 88/05297 A1 | 7/1988 |
| WO | WO 93/20826 A1 | 10/1993 |
| WO | WO 94/10202 A1 | 5/1994 |
| WO | WO 95/31985 A2 | 11/1995 |
| WO | WO 96/14058 A1 | 5/1996 |
| WO | WO 96/23793 A1 | 8/1996 |
| WO | WO 97/07118 A1 | 2/1997 |
| WO | WO 97/29739 A2 | 8/1997 |
| WO | WO 97/33566 A2 | 9/1997 |
| WO | WO 98/25613 A2 | 6/1998 |
| WO | WO 99/22737 A1 | 5/1999 |
| WO | WO 99/36470 A1 | 7/1999 |
| WO | WO 99/40089 A1 | 8/1999 |
| WO | WO 01/13909 A2 | 3/2001 |
| WO | WO 01/32180 A2 | 5/2001 |
| WO | WO 01/37785 A2 | 5/2001 |
| WO | WO 01/41705 A2 | 6/2001 |
| WO | WO 01/42207 A2 | 6/2001 |
| WO | WO 01/70031 A1 | 9/2001 |
| WO | WO 01/85257 A2 | 11/2001 |
| WO | WO 02/060870 A2 | 8/2002 |
| WO | WO 02/098422 A1 | 12/2002 |
| WO | WO 03/020296 A1 | 3/2003 |
| WO | WO 03/032990 A2 | 4/2003 |
| WO | WO 03/037340 A1 | 5/2003 |
| WO | WO 03/077867 A2 | 9/2003 |
| WO | WO 2004/014291 A2 | 2/2004 |
| WO | WO 2004/043964 A2 | 5/2004 |
| WO | WO 2004/080996 A1 | 9/2004 |
| WO | WO 2004/091623 A1 | 10/2004 |
| WO | WO 2006/096626 A2 | 9/2006 |
| WO | WO 2006/127898 A2 | 11/2006 |
| WO | WO 2006/127899 A2 | 11/2006 |
| WO | WO 2006/132963 A2 | 12/2006 |
| WO | WO 2006/135650 A1 | 12/2006 |
| WO | WO 2007/053194 A2 | 5/2007 |
| WO | WO 2007/053698 A2 | 5/2007 |
| WO | WO 2007/131154 A2 | 11/2007 |
| WO | WO 2008/016704 A1 | 2/2008 |
| WO | WO 2008/019115 A2 | 2/2008 |
| WO | WO 2008/064150 A1 | 5/2008 |
| WO | WO 2008/064351 A2 | 5/2008 |
| WO | WO 2008/064353 A2 | 5/2008 |
| WO | WO 2008/070462 A2 | 6/2008 |
| WO | WO 2008/121348 A2 | 10/2008 |
| WO | WO 2008/121860 A1 | 10/2008 |

OTHER PUBLICATIONS

[No Author Lsted] Pain management; cancer-pain remedy wins orphan drug status. Cancer Biotechnology Weekly. Aug. 12, 1996; 2 pages.

[No Author Listed] Progenics achieves enrollment target in pivotal phase 3 clinical trial of methylnaltrexone for opioid-induced constipation. Press Release. Progenics Pharmaceuticals, Inc. Dec. 3, 2004.

[No Author Listed] Progenics announces positive top-line results from pivotal phase 3 clinical trial of MNTX in opioid-induced constipation. Pre0ss Release. Progenics Pharmaceuticals, Inc. Mar. 10, 2005.

[No Author Listed] Progenics initiates second phase 3 clinical trial of methylnaltrexone in opioid-induced constipation. Press Release. Progenics Pharmaceuticals, Inc. Jan. 13, 2004.

[No Author Listed] Remington's Pharmaceutical Sciences. 15$^{th}$ Edition. 1995:1614-5.

[No Author Listed] Remington's Pharmaceutical Sciences. 15$^{th}$ Edition. 1995:201-02.

[No Author Listed] Remington's Pharmaceutical Sciences. 15$^{th}$ Edition. 1995:273-74.

[No Author Listed] Remington's Pharmaceutical Sciences. 15$^{th}$ Edition. 1995:1466.

[No Author Listed] The Merck Manual. 17$^{th}$ edition. 1999:312-315.

Akinbami et al., Effect of a peripheral and a central acting opioid antagonist on the testicular response to stress in rats. Neuroendocrinology. Apr. 1994:59(4):343-8.

Altier et al., Opioid receptors in the ventral tegmental area contribute to stress-induced analgesia in the formalin test for tonic pain. Brain Res. Apr. 29, 1996;718(1-2):203-6.

Amin et al., Efficacy of methylnaltrexone versus naloxone for reversal of morphine-induced depression of hypoxic ventilatory response. Anesth Analg. Apr. 1994;78(4):701-5.

Amir, Naloxone improves, and morphine exacerbates, experimental shock induced by release of endogenous histamine by compound 48/80. Brain Res. Apr. 9, 1984;297(1):187-90.

(56) References Cited

OTHER PUBLICATIONS

Amir et al., Endorphins in endotoxin-induced hyperglycemia in mice. Arch Toxicol Suppl. 1983;6:261-5.
Arendt et al., Bidirectional effects of endogenous opioid peptides on endothelin release rates in porcine aortic endothelial cell culture: mediation by delta opioid receptor and opioid receptor antagonis-insensitive mechanism. J Pharmacol Exp Ther. Jan. 1995;272(1):1-7.
Arerangaiah et al., Opioids induce renal abnormalities in tumor-bearing mice. Nephron Exp Nephrol. 2007;105(3):e80-9. Epub Jan. 12, 2007.
Argentieri et al., Interation of the opiate antagonist, naltrexone methyl bromide, with the acetylcholine receptor system of the motor end-plate. Brain Res. Oct. 31, 1983;277(2):377-9.
Armstead, Relationship among NO, the KATP channel, and opioids in hypoxic pial artery dilation. Am J Physiol. Sep. 1998;275(3 Pt 2):H988-94.
Armstrong et al., The gastrointestinal activity and peripheral selectivity of alvimopan, ADL08-0011, and naloxone in mice. May 21, 2006 DDW Presentation in Los Angeles. Clincial Phar Therap. 2005;77:74. Abstract #221957.
Attali et al., Kappa opiate agonists inhibit Ca2+ influx in rat spinal cord-dorsal root ganglion cocultures. Involvement of a GTP-binding protein. J Biol. Chem. Jan. 5, 1989;264(1):347-53.
Aung et al., Methylnaltrexone prevents morphine-induced kaolin intake in the rat. Life Sci. Apr. 16, 2004;74(22):2685-91.
Aung et al., *Scutellaria baicalensis* decreases ritonavir-induced nausea. AIDS Res. Ther. Dec. 20, 2005;2:12.
Bagnol et al., Changes in enkephalin immunoreactivity of sympathetic ganglia and digestive tract of the cat after splanchnic nerve ligation. Regul Pept. Sep. 22, 1993;47(3):259-73. Abstract Only.
Baker, et al., Functional effects of systemically administered agonists and antagonists of mu, delta, and kappa opioid receptor subtypes on body temperature in mice. J Pharmacol Exp. Ther. Sep. 2002;302(3):1253-64.
Balasubramanian et al., Morphine sulfate inhibits hypoxia-induced vascular endothelial growth factor expression in endothelial cells and cardiac myocytes. J Mol Cell Cardiol. Dec. 2001;33(12):2179-87.
Baratti et al., Brain opioid peptides may participate in the reversal of pentylenetetrazol-induced amnesia. Methods Find Exp Clin Pharmacol. Sep. 1990;12(7):451-6.
Basilisco et al., Oral naloxone antagonizes loperatmide-induced delay of orocecal transit. Dig Dis Sci. Aug. 1987;32(8):829-32.
Basilisco et al., Effect of loperamide and naloxone on mouth-to-caecum transit time evaluated by lactulos hydrogen breath test. Gut. Jul. 1985;26(7):700-3.
Bedingfield et al., Methylnaltrexone attenuates taste aversion conditioned by low-dose ethanol. Alcohol. Jan. 1998;15(1):51-4.
Belcheva et al., μ-Opioid receptor-mediated ERK activation involves calmodulin-dependent epidermal growth factor receptor transactivation. J Biol Chem. Sep. 7, 2001;276(36):33847-53. Epub Jul. 16, 2001.
Belcheva et al., μ opioid transactivation and down-regulation of the epidermal growth factor receptor in astrocytes: implications for mitogen-activated protein kinase signaling. Mol Pharmacol. Dec. 2003;64(6):1391-401.
Bianchetti et al., Quaternary derivatives of narcotic antagonists: sterochemical requirements at the chiral nitrogen for in vitro and in vivo activity. Life Sci. 1983;33 Suppl. 1:415-8.
Bianchi et al., Quaternary narcotic antagonists' relative ability to prevent antinociception and gastrointestinal transit inhibition in morphine-treated rats as an index of peripheral selectivity. Life Sci. May 31, 1982;30(22):1875-83.
Bickel, Stimulation of colonic motility in dogs and rats by an enkephalin analogue pentapeptide. Life Sci. 1983;33 Suppl 1:469-72.
Bigliardi et al., Changes of epidemal mu-opiate receptor expression and nerve endings in chronic atopic dermatitis. Dermatology. 2005;210(2):91-9.
Bigliardi et al., Different expression of mu-opiate receptor in chronic and acute wounds and the effect of beta-endorphin on transforming growth factor beta type II receptor and cytokeratin 16 expression. J Invest Dermatol. Jan. 2003;120(1):145-52.
Binder et al., Effect of the peripherally selective kappa-opioid agonist, asimadonline, on adjuvant arthritis. Br J Pharmacol. Jun. 1998;124(4):647-54.
Blank et al., Central, stereoselctive receptors mediate the acute effects of opiate antagonist on luteinizing hormone secretion. Life Sci. Oct. 27, 1986;39(17):1493-99.
Blebea et al., Differential effects of vascular growth factors on arterial and venous angiogenesis. J Vasc Surg. Mar. 2002;35(3):532-8.
Blebea et al., Opioid growth factor modulates angiogenesis. J Vasc Surg. Aug. 2000;32(2):364-73.
Bond et al., Investigation of small bowel transit time in man utilizing pulmonary hydrogen (H2) measurements. J Lab Clin Med. Apr. 1975;85(4):546-55. Abstract Only.
Bonn, Morphine stimulates tumour growth. Lancet Oncol. Sep. 2002;3(9):530.
Boonnstra et al., Engineering novel biocatalytic routes for production of semisynthetic opiate drugs. Biomol Eng. Sep. 2001;18(2):41-7.
Bös et al., A Short and Efficient Synthesis of C-Nor-Dihydrocodeinone—The Antipode of Goto's Sinomenilone, Heterocycles. 1983;20(6):1077-81.
Bowen et al., Antagonism of the antinociceptive and discriminative stimulus effects of heroin and morphine by 3-methoxynaltrexone and naltrexone in rhesus monkeys. J Pharmacol Exp Ther. Jul. 2002;302(1):264-73.
Bowen et al., College on Problems of Drug Dependence 64th Annual Scientific Meeting. Jun. 8-13, 2002. Quebec City, Quebec, Canada. Abstracts. Drug Alcohol Depend. May 1, 2002;66 Suppl 1:S1-220. Abstract No. 65.
Breitbart et al., Control of non-pain symptoms in HIV/AIDS. J Back Musculoskelet Rehabil. 1997;8(3):243-46.
Brix-Christensen et al., Endogenous morphine is produced in response to cardiopulmonary bypass in neonatal pigs. Acta Anaesthesiol Scand. Nov. 2000;44(10):1204-8.
Brix-Christensen el al., Endogenous morphine levels increase following cardiac surgery as part of the nti-inflammatory response? Int J Cardiol. Dec. 19, 1997;62(3):191-7.
Brondsted et al., Hydrogels for site-specific drug delivery to the colon: in vitro and in vivo degradation. Pharm Res. Dec. 1992;9(12):1540-5. Abstract Only.
Brown et al., Opiate antagonists: central sites of action in suppressing water intake of the rat. Brain Res. Sep. 28, 1981;221(2):432-6.
Brown et al., Reversal of morphine-induced catalepsy in the rat by narcotic antagonists and their quaternary derivatives. Neuropharmacology. Mar. 1983;22(3):317-21.
Brown et al., Techniques for mechanical stimulation of cells in vitro: a review. J Biomech. Jan. 2000;33(1):3-14.
Brown et al., The use of quaternary narcotic antagonists in opiate research. Neuropharmacology, Mar. 1985;24(3):181-91.
Bruce et al., Microbial degradation of the morphine alkaloids: identification of morphine as an intermediate in the metabolism of morphine by *Pseudomonas putida* M10, Arch Microbiol. 1990;154(5):465-70.
Bruley-Des-Varannes et al.,Cholécystokine et ses antagonistes: effets sur la motricité digestive. Gastroenterol Clin Biol. 1991;15:744-57. French.
Bundgaard et al., (C) Means to Enhance Penetration, (1) Prodrugs as a means to improve the delivery of peptide drugs. J Drug Delivery Rev. 1992;8:1-38.
Burkhart et al., Metkephamid (Tyr-D-Ala-Ciy-Phe-N(Me)Met-NH$_2$), a Potent Opioid Peptide: Receptor Binding and Analgesic Properties. Peptides. 1982;3:869-71.
Caballero-Hernandez et al, Potentiation of rat lymphocyte proliferation by novel non-peptidic synthetic opioids. Int Immunopharmacol. Jul. 2005;5(7-8):1271-8. Epub Apr. 12, 2005.
Cadet et al., Differential expression of the human mu opiate receptor from different primary vascular endothelial cells, Med Sci Monit. Oct. 2004;10(10):BR351-5. Epub Sep. 23, 2004.
Cadet el al., Molecular identification and functional expression of mu 3, a novel alternatively spliced variant of the human mu opiate receptor gene. J Immunol, May 15, 2003;170(10):5118-23.

(56) References Cited

OTHER PUBLICATIONS

Calcagnetti et al., Quaternary naltrexone reveals the central mediation of conditional opioid analgesia. Pharmacol Biochem Behav. Jul. 1987;27(3):S29-31.

Cao et al., Cardioprotection of interleukin-2 is mediated via kappa-opioid receptors. J Pharmacol Exp Ther. May 2004;309(2):560-7. Epub Jan. 27, 2004.

Carr et al., Naltrexone antagonizes the analgesic and immunosuppressive effects of morphine in mice. J Pharmacol Exp Ther. May 1994;269(2):693-8.

Chang et al., An antiabsorptive basis for precipitated withdrawal diarrhea in morphine-dependent rats. J Pharmacol Exp Ther. Feb. 1984;228(2)364-9.

Chang et al., The association between opiates and cytokines in disease. Adv Exp Med Biol. 1998;437:4-6.

Chatterjie et al., Stereospecific synthesis of the 6beta-hydroxy metabolites of naltrexone and naloxone. J Med Chem. May 1975;18(5):490-2. Abstract Only.

Chen et al., Morphine stimulates vascular endothelial growth factor-like signaling in mouse retinal endothelial cells, Curr Neurovasc Res. Aug. 2006;3(3):171-80.

Choi et al., Opioid antagonists: a review of their role in palliative care, focusing on use in opioid-related constipation. J Pain Symptom Manage. Jul. 2002;24(1):71-90. Review.

Choi et al., Inhibition of chemokine-induced chemotaxis of monkey leukocytes by mu-opioid receptor agonist. In Vivo. Sep.-Oct. 1999;13(5):389-96.

Collins et al., Peak plasma concentrations after oral morphine: a systematic review. J Pain Symptom Manage. Dec. 1998;16(6):388-402.

Cone et al., The identification and measurement of two new metabolites of naltrexone in human urine. Res Commun Chem Pathol Pharmacol. Jun. 1978;20(3):413-3. Abstract Only.

Cozzolino et al., Acute effects of beta-endorphin on cardiovascular function in patients with mild to moderate chronic heart failure. Am Heart J. Sep. 2004;148(3):E13.

Culpepper-Morgan et al., Treatment of opioid-induced constipation with oral naloxone: a pilot study. Clin Pharmacol Ther. Jul. 1992;52(1):90-5. Abstract Only.

D'Amato et al., Studies of three non-peptide cholecystokinin antagonists (devazepide, lorglumide and loxiglumide) in human isolated alimentary muscle and guinea-pig ileum. Br J Pharmacol. Feb. 1991;102(2):391-5.

Dajani et al., Effects of E prostaglandins, diphenoxylate and morphine on intestinal motility in vivo. Eur J Pharmacol. Nov. 1975;34(1):105-13. Abstract Only.

Dajani et al., The pharmacology of SC-27166: a novel antidiarrheal agent. J Pharmacol Exp Ther. Dec. 1977;203(3):512-26. Abstract Only.

Daniel et al., Effects of morphine and other drugs on motility of the terminal ileum. Gastroenterology. Apr. 1959;36(4):510-23.

De Ponti et al., Methylnaltrexone Progenics. Curr Opin Investig Drugs. Apr. 2002;3(4):614-20. Review.

De Schryver et al., New developments in the treatment of irritable bowel syndrome. Scand J Gastroenterol Suppl. 2000;(232):38-42. Review.

Doherty el al., Route-dependent metabolism of morphine in the vascularly perfused rat small intestine preparation. Pharm Res. Mar. 2000,17(3):291-8.

Dragonetti et al., Levallorphan methyl iodide (SR 58002), a potent narcotic antagonist with peripheral selectivity superior to that of other quaternary compounds. Life Sci. 1983:33 Suppl 1:477-80.

Egan et al., Prospective pharmacokinetic and pharmacodynamic validation of propofol's context sensitive T1/2. Anesthesiology. Sep. 1999;91(3A): Abstract A347.

Eisenberg, Effects of naltrexone on plasma corticosterone in opiate-naïve rats: a central action. Life Sci. Mar. 19, 1984;34(12):1185-91.

Eisenstein et al., Effect of opioids on oral *Salmonella* infection and immune function. Adv Exp Med Biol. 2001;493:169-76.

Epstein et al., Naltrexone attenuates acute cigarette smoking behavior, Pharmacol Biochem Behav. Jan. 2004,77(1):29-37.

Farthing et al., New drugs in the management of the irritable bowel syndrome. Drugs. Jul. 1998;56(1):11-21.

Farooqui et al., µ opioid receptor stimulates a growth promoting and pro-angiogenic tumor microenvironment. Proc Amer Assoc Cancer Res. 2005;46. AACR Meeting Abstract, Abstract #4650.

Farooqui et al., Naloxone acts as an antagonist of estrogen receptor activity in MCF-7 cells. Mol Cancer Ther. Mar. 2006;5(3):611-20.

Farup et al., The Symptomatic Effect of Cisapride in Patients with Irritable Bowel Syndrome and Constipation. Scand J Gastronenerol. 1998;33:28-31.

Faura et al., Systematic review of factors affecting the ratios of morphine and its major metabolites. Pain. Jan. 1998;74(1):43-53.

Fecho et al., Assessment of the involvement of central nervous system and peripheral opioid receptors in the immunomodulatory effects of acute morphine treatment in rats. J Pharmacol Exp Ther. Feb. 1996;276(2):626-36.

Fernandez-Tome et al., Interaction between opioid agonists or naloxone and 5-HTP on feeding behavior in food-deprived rats, Pharmacol Biochem Behav. Feb. 1988;29(2):387-92.

Fingl et al., Chapter 43: Laxatives and cathartics. In Pharmacological Basis of Therapeutics. 1980: 1002-5.

Finn et al., Endocytosis of the mu opioid receptor reduces tolerance and a cellurlar hallmark of opiate withdrawal. Neuron. Dec. 6, 2001;32(5):829-39.

Flores et al., Mechanisms of morphine-induced immunosuppression: effect of acute morphine administration on lymphocyte trafficking. J Pharmacol Exp Ther. Mar. 1995;272(3):1246-51.

Foss et al., Alvimopan (Entereg™), a novel opioid antagonist; achieves active systemic concentrations. Amer Soc Clin Pharma Ther. 2005:74. Abstract P11-90.

Foss et al., Dose-related antagonism of the emetic effect of morphine by methylnaltrexone in dogs. J Clin Pharmacol. Aug. 1993;33(8):747-51.

Foss et al., Effects of methylnaltrexone on morphine-induced cough suppression in guinea pigs. Life Sci. 1996;59(15):PL235-8.

Foss et al., Enteric-coated methylnaltrexone prevents opioid-induced oral-cecal transit delay in humans. Anesth Analg. 2000;90. Abstract S409.

Foss et al., Methylnaltrexone does not antagonize the analgesic effect of morphine: a clinical study, 1995 Annual scientific meeting of the American Society of Anesthesiologists, Atlanta, Georgia, Oct. 21-25, 1995. Abstracts. Anesthesiology. Sep. 1995;83(3A Suppl):A361.

Foss et al., Methylnaltrexone reduces morphine-induced postoperative emesis by 30%. Anesth Analg. 1994;78:S119.

Foss et al., Prevention of apomorphine- or cisplatin-induced emesis in the dog by a combination of methylaltrexone and morphine. Cancer Chemother Pharmacol. 1998;42(4):287-91.

Foss et al., Safety and tolerance of methylnaltrexone in healthy humans: a randomized, placebo-controlled, intravenous, ascending-dose, pharmacokinetic study. J Clin Pharmacol. Jan. 1997;37(1):25-30.

Foss et al., Subcutaneous methylnaltrexone reduces morphine-induced subjective effects in humans. Anesthesiology. 2001;95. Abstract A-817.

Foss et al., The efficacy or oral methylnaltrexone in decreasing the subjective effects of IV morphine. Anesth Analg. 1997;84. Abstract S484.

Foss, A review of the potential role of methylnaltrexone in opioid bowel dysfunction. Am J Surg. Nov. 2001;182(5A Suppl):19S-26S.

France et al., Morphine, saline and naltrexone discrimination in morphine-treated pigeons. J Pharm and Exper Ther. 1987;242:195-202.

France et al., Comparison of naltrexone and quaternary naltrexone after systemic and intracerebroventricular administration in pigeons. Neuropharmacology. Jun. 1987;26(6):541-8.

France et al., Intracerebroventricular drug administration in pigeons. Pharmacol Biochem Behav. Nov. 1985;23(5):731-6.

Fraser et al., Methods for evaluating addiction liability. (A) "Attitude" of opiate addicts toward opiate-like drugs. (B) a short-term "direct" addiction test. J Pharmacol Exp Ther. Sep. 1961;133:371-87. Abstract Only.

(56) References Cited

OTHER PUBLICATIONS

Frässdorf et al., Morphine induces late cardioprotection in rat hearts in vivo: the involvement of opioid receptors and nuclear transcription factor kappaB. Anesth Analg. Oct. 2005;101(4):934-41.
Frederickson et al., Metkephamid, a Systemically Active Analog of Methionine Enkephalin Potent Opioid δ-Receptor Activity. Science. 1991;211:603-05.
French et al., Purification and characterization of morphinone reductase from *Pseudomonas putida* M10. Biochem J. Jul. 1, 1994;301 ( Pt 1):97-103.
Friedman et al., Opioid antagonists in the treatment of opioid-induced constipation and pruritus. Ann Pharmacother. Jan. 2001;35(1):85-91.
Funke et al., A proton and carbone-13 nuclear magnetic resonance study of three quaternary salts of naloxone and oxymorphone. J Chem Soc. 1986:735-8.
Galligan et al., Centrally mediated inhibition of small intestinal transit and motility by morphine in the rat. J Pharmacol Exp Ther. Aug. 1983;226(2):356-61 Abstract Only.
Gan et al., Consensus guidelines for managing postoperative nausea and vomiting. Anesth Analg. Jul. 2003;97(1):62-71. Review.
Gervitz, Targeted approach: methylnaltrexone blocks opioid-induced constipation and other peripheral side effects. Topics in Pain Management 2005;21(1):6-8.
Giles et al., Quaternary opiate antagonists lower blood pressure and inhibit leucine-enkephalin responses. Eur J Pharmacol. Nov. 25, 1983;95(3-4):247-52.
Gmerek et al., Independent central and peripheral mediation of morphine-induced inhibition of gastrointestinal transit in rats. J Pharmacol Exp Ther, Jan. 1986;236(1):8-13.
Green, Comparative effects of analgesics on pain threshold, respiratory frequency and gastrointestinal propulsion. Br J Pharmacol Chemother. Mar. 1959;14(1):26-34.
Grigoriev et al., Clinical gastroenterology. Ministry of Health of the Russian Federation. Russian State Medical University. 2001;491-492. Russian.
Goumon et al., *Ascaris suum*, an intestinal parasite, produces morphine. J Immunol. Jul. 1, 2000;165(1):339-43.
Gupta et al., Angiogenesis: a curse or cure? Postgrad Med J. Apr. 2005;81(954):236-42.
Gupta et al., Morphine mimics VEGF in vascular endothelium by promoting pro-angiogenic and survival promoting signaling and angiogenesis. FASEB Journal. 2002;16(4):A207. Abstract #182.12.
Gupta et al., Morphine stimulates angiogenesis by activating; proangiogenic and survival-promoting signaling and promotes breast tumor growth. Cancer Res. Aug. 1, 2002;62(15):4491-8.
Gutstein et al., Role of inositol 1,4,5-trisphosphate receptors in regulating apoptotic signaling and heart failure. Heart Vessels. 1997;Suppl 12:53-7.
Guy et al., Structural models of $Na^+$, $Ca^{2+}$, and $K^+$ channels. Ion Channels and Genetic Diseases. 1995;Chapter 1, 1-28.
Hailes et al., Biological synthesis of the analgesic hydromorphone, an intermediate in the metabolism of morphine, by *Psendomonas putida* M10. Appl Environ Microbiol. Jul. 1993;59(7):2166-70.
Hanif et al., Hypotensive effect of novel chimeric peptides of met-enkephalin and FMRFa. Regul Pept. Feb. 15, 2005;125(1-3):155-61.
He et al., Improvement of Bowel Dysfunction Caused by Opioid Analgesics: Research Advances on Methylnaltrexone. Chinese Journal of Clinical Rehabilitation. 2002;6(20):3104-05.
Hein et al., Pharmacological analysis of the discriminative stimulus characteristics of ethylketazocine in the rhesus monkey. J Pharmacol Exp Ther. Jul. 1981;218(1):7-15.
Hicks et al., Differential effects of the novei non-peptidic opioid 4-tyrosylamido-6-benzyl-1,2,3,4 tetrahydroquinoline (CGPM-9) on in vitro rat t lymphocyte and macrophage functions. Life Sci. May 4, 2001;68(24):2685-94.
Hirota et al., Loss of a gp130 cardiac muscle cell survival pathway is a critical event in the onset of heart failure during biomechanical stress. Cell. Apr. 16, 1999;97(2):189-98.

Ho et al., Suppression of immunological functions in morphine addicted mice. NIDA Res Monogr. 1986;75:599-602.
Ho et al., Beta-endorphin: periperal opioid activity of homolgues from six species. Int J Pept Protein Res. Apr. 1987;29(4):521-4.
Ho et al., Methylnaltrexone antagonizes opioid-mediated enhancement of HIV infection of human blood mononuclear phagocytes. J Pharmacol Exp Ther. Dec. 2003;307(3):1158-62. Epub Oct. 14, 2003.
Hoffmann et al., [Calcium in the prevention of stress ulcer in the rat] Langenbecks Arch Chir. 1976;Suppl:228-32. German.
Hofmann et al., Hypocalcemia during restraint stress in rats. Indication that gastric ulcer prophylaxis by exogenous calcium interferes with calcitonin release. Res Exp Med (Berl). May 30, 1979;175(2):159-68.
Hou et al., A mu-receptor opioid agonist induces AP-1 and NF-kappa B transcription factor activity in primary cultures of rat cortical neurons. Neurosci Lett. Jul. 19, 1996;212(3):159-62.
Howd et al., Naloxone and intestinal motility. Experientia. Oct. 15, 1978;34(10):1310-1.
Hussain et al., Improvement of the oral bioavailability of naltrexone in dogs: a prodrug approach. J Pharm Sci. May 1987;76(5):356-8.
Hussain et al., Naltrexone-3-salicylate (a prodrug of naltrexone): synthesis and pharmacokinetics in dogs. Pharm Res. Feb. 1988;5(2):113-5.
Hutchinson et al., Assessment in the guinea-pig ileum and mouse vas deferens of benzomorphans which have strong antinociceptive activity but do not substitute for morphine in the dependent monkey. Br J Pharmacol. Dec. 1975;55(4):541-6.
Hutchinson et al., Scintigraphic measurement of ileocaecal transit in irritable bowel syndrome and chronic idiopathic constipation. Gut. Apr. 1995;36(4):585-9.
Iorio et al., Narcotic agonist/antagonist properties of quaternary diastereoisomers derived from oxymorphone and naloxone. Eur J Med Chem. 1984;19(4):301-3.
Iorio et al., Diastereoisomerie Quaternary Morphinium Salts: Synthesis, Stereochemistry and Analgesic Properties. European Journal of Medicinal Chemistry. 1984;19(1):11-16.
Jalowiec et al., Suppression of juvenile social behavior requires antagonism of central opioid systems. Pharmacol Biochem Behav. Jul. 1989;33(3):697-700.
Jankovic el al., Quaternary naltrexone: its immunomodulatory activity and interaction with brain delta and kappa opioid receptors. Immunopharmacology. Sep.-Oct. 1994;28(2):105-12.
Jasinski, Assesment of the Abuse Potentiality of Morphinelike Drugs (Methods Used in Man). Drug Addiction J. 1997:197-258.
Jasinski, Tolerance and Dependence to opiates. Acta Anaesthesiol Scand. Jan. 1997;41(1 Pt 2):184-6.
Jenab et al., Ethanol and naloxone differentially upregulate delta opioid receptor gene expression in neuroblastoma hybrid (NG108-15) cells. Brain Res Mol Brain Res. Nov. 1994;27(1):95-102.
Johnson et al., Stability of tacrolimus with morphine sulfate, hydromorphone hydrochloride, and ceftazidime during simulated intravenous coadministration. Am J Health Syst Pharm. Jan. 15, 1999;56(2):164-9.
Kakeji et al., Preclinical studies of the cmbination of angiogenic inhibitors with cytotoxic agents. Invest New Drugs. 1997;15(1):39-48.
Kasamatsu et al., Attenuation of aortic baroreflex responses by microinjections of endomorphin-2 into the rostral ventrolateral medullary pressor area of the rat. Am J Physiol Regul Integr Comp Physiol. Jul. 2005;289(1):R59-67. Epub Feb. 17, 2005.
Kaufman et al., Role of opiate receptors in the regulation of colonic transit. Gastroenterology. Jun. 1988;94(6):1351-6.
Kehlet et al., Review of postoperative ileus. Am J Surg. Nov. 2001;182(5A Suppl):3S-10S. Review.
Keith et al., Failure of naloxone to prevent the emetic activity of apomorphine in dogs. J Vet Pharmacol Ther. Dec. 1981;4(4):315-6.
Kim et al., Assay for methylnaltrexone in rat brain regions and serum by high-performance liquid chromatography with coulometric electrochemical detection. Chromatographia. Oct. 1989;28(7-8):359-63.
King et al., Hypothalamic-pituitary-adrenocortical(HPA) axis response and biotransformation of oral naltrexone: preliminary

(56) References Cited

OTHER PUBLICATIONS examination of relationship to family history of alcoholism. Neuropsychopharmacology, Jun. 2002:26(6):778-88.

Kinsman et al., Effect of naloxone on feedback regulation of small bowel transit by fat. Gastroenterology. Aug. 1984;87(2):335-7.

Knowles et al., Slow transit constipation: a model of human gut dysmotility. Review of possible aetiologies. Neurogastroenterol Motil. Apr. 2000;12(2):181-96.

Kodani et al., Delta-opioid receptor-induced late preconditioning is mediated by cyclooxygenase-2 in conscious rabbits. Am J Physiol Heart Circ Physiol. Nov. 2002;283(5):H1943-57.

Koblish el al., Behavioral profile ADL 8-2698, a novel GI-restricted μ opioid receptor antagonist. Society for Neuroscience Abstracts. 2001;27(2):2407. Abstract Only.

Kobylecki et al., N-Methylnalorphine: definition of N-allyl conformation for antagonism at the opiate retceptor. J. Med Chem. Nov. 1982;25(11):1278-80.

Koch et al., Inhibitory neuropeptides and intrinsic inhibitory innervation of descending human colon. Dig Dis Sci. Jun. 1991;36(6):712-8. Abstract Only.

Koczka, et al., Acta Chimic Academica Scien. Hung. (1967) 51(4), 393-02.

Koob et al., Effects of opiate antagonists and their quaternary derivatives on heroin self-administration in the rat. J Pharmacol Exp Ther. May 1984;229(2):481-6.

Kosten et al., Naltrexone and morphine alter the discrimination and plasma levels of ethanol. Behav Pharmacol. Feb. 1999;10(1):1-13.

Kostic, CAS Abstract Document No. 127: 13345, 1997.

Kotake et al., Variations in demethylation of N-methylnaltrexone in mice, rats, dogs, and humans. Xenobiotica. Nov. 1989;19(11):1247-54.

Kratzel et al., An Effificent Synthesis of 14-Halogenomethyl-Substituted C-Normorphinans. Heterocycles. 1987;26(10):2703-10.

Kratzel et al., Synthesis of 5a,11b-Propanonaphthor[,1,2-e][1,2]oxazepines as Potential Opioid Analgesics. J Chem Soc Perkin 1. 1994;11:1541-43.

Kromer et al., Endogenous opioids, the enteric nervous system and gut motility. Dig Dis. 1990;8(6):361-73.

Kromer et al., The current status of opioid research on gastrointestinal motility. Life Sci. 1989;44(9):579-89.

Law et al., Agonist activation of delta-opioid receptor but not mu-opioid receptor potentiates fetal calf serum or tyrosine kinase receptor-mediated cell proliferation in a cell-line-specific manner. Mol Pharmacol. Jan. 1997;51(1):152-60.

Law et al., Properties of delta opioid receptor in neuroblastoma NS20Y: receptor activation and neuroblastoma proliferation. J Pharmacol Exp Ther, Jan. 1995;272(1):322-32.

Law et al., Regulation of opioid receptor activities. J Pharmacol Exp Ther, May 1999:289(2):607-24.

Lazar et al., Synthesis and biological activity of the phosphate and sulfate esters of naloxone and naltrexone. Eur J Med Chem. 1994;29:45-53.

Leander, A kappa opioid effect: increased urination in the rat. J Pharmacol Exp Ther. Jan. 1983:224(1):89-94.

Li et al., Methadone enhances human immunodeficiency virus infection of human immune cells. J Infect Dis. Jan. 1, 2002;185(1):118-22. Epub Dec. 14, 2001.

Lim et al., Morphine preconditions Purkinje cells against cell death under in vitro simulated ischemia-reperfusion conditions. Anesthesiology. Mar. 2004;100(3):562-8.

Linn et al., Peripherally restricted μ-opioid receptor antagonists: a review. Tech Reg Anesth Pain Manag. Jul. 2007;11(1):27-32.

Little, et al., ADL 8-2698, a GI restricted opioid antagonist, blocks the antisecretory and colorectal transit effects of morphine and loperamide. Society for Neuroscience Abstracts. 2001; 27(2):2407. Abstract Only.

Livingston et al., Postoperative ileus. Dig Dis Sci. Jan. 1990;35(1):121-32.

Lopez et al., Demonstration of long-lasting blockade of experimental ileus in rats by an opioid k-agonist. Gastroenterology. 1995;108(4):A640. Abstract.

Lydon et al., Intravenous methylnaltrexone attenuates intrathecal morphine induced delayed gastric emptying in rats. ESA Free Paper Prize Competition. Eur J Anaesthesiol. Apr. 2001;18 Suppl 21:92. Abstract A-327.

Lysle et al., Evidence for the involvement of the caudal region of the periaqueductal gray in a subset of morphine-induced alterations of immune status. J Pharmacol Exp Ther. Jun. 1996;277(3):1533-40.

Lysle et al., Modulation of immune status by a conditioned aversive stimulus: evidence for the involvement of endogenous opioids. Brain Behav Immun. Jun. 1992;6(2):179-88.

Machelska et al., Selectins and integrins but not platelet-endothelial cell adhesion molecule-1 regulate opioid inhibition of inflammatory pain. Br J Pharmacol. Jun. 2004;142(4):772-80. Epub May 24, 2004.

Mack, Paralytic ileus: response to naloxone. Br J Surg. Oct. 1989;76(10):1101.

Magazine et al., Morphine-induced conformational changes in human monocytes, granulocytes, and endothelial cells and in invertebrate immunocytes and microglia are mediated by nitric oxide. J Immunol. Jun. 15, 1996;156(12):4845-50.

Magnan et al., The binding spectrum of narcotic analgesic drugs with different agonist and antagonist properties. Naunyn Schmiedebergs Arch Pharmacol. Jun. 1982;319(3):197-205.

Maguire el al., Pharmacological profiles of fentanyl analogs at mu, delta and kappa opiate receptors. Eur J Pharmacol. Mar. 24, 1992;213(2):219-25. Abstract Only.

Malspeis et al., Metabolic Reduction of Naltrexone 1. Synthesis, Separation and Characterization of Naloxone and Maltrexone Reduction Products and Qualitative Assay of Urine and Bile Following Adminstration of Naltrexone, α-naltrexol, or β-naltrexol. Chem Pathol Pharmacol. 1975;12(1):43-65.

Manara et al., Inhibition of gastrointestinal transit by morphine in rats results primarily from direct drug action on gut opioid sites. J Pharmacol Exp Ther. Jun. 1986;237(3):945-9. Abstract Only.

Manara et al., Peripheral selectivity of quaternary narcotic antagonists: relative ability to prevent gastrointestinal transit inhibition and antinociception in morphinized rats. Adv. Endog. Exog. Opioids, Poroc. Int. Narc. Res. Conf., 12th (1981): 402-4.

Manara et al., The central and peripheral influences of opioids on gastrointestinal propulsion. Annu Rev Pharmacol Toxicol. 1985;25:249-73.

Mančev et al., The immunomodulating effects of specific opioid receptor antagonists after their intracerebroventricular application. Intl J Thymol. 1999;7(12-13):589-95.

Marmor et al., Coronary artery disease and opioid use. Am J Cardiol. May 15, 2004;93(10):1295-7.

McBride et al., Delta2 opioid receptor agonist facilitates mean arterial pressure recovery after hemorrhage in conscious rats. Shock. Mar. 2005;23(3):264-8.

McCance-Katz et al., Ineractions between buprenoorphine and antiretrovirals. II. The protease inhibitors nelfinavir, lopinaviar/ritonavir, and ritonavir. Clin Infect Dis. Dec. 15, 2006;43 Suppl 4:S235-46.

McCarthy et al., Opioids, opioid receptors, and the immune response, Drug Alcohol Depend. Apr. 1, 2001;62(2):111-23.

McCarthy et al., Preliminary studies on the use of plasma β-endorphin in horses as an indicator of stress and pain. J Equine Vet Sci. 1993;13(4):216-9.

McQuay et al., Opioid problems and morphine metabolism and excretion. http://www.medicine.ox.ac.uk/bandolier/booth/painpag/wisdom/c14.html. Last accessed Feb. 8, 2010. 24 pages.

McQuay, Opioid use in chronic pain. Acta Anaesthesiol Scand. Jan. 1997;41(1 Pt 2):175-83.

Mellon et al., Evidence for central opioid receptors in the immornodulatory effects of morphine: review of potential mechanism(s) of action. J Neuroimmunol. Mar. 15, 1998;83(1-2):19-28.

Melzig et al., Stimulation of endothelial angiotensin-converting enzyme by morphine via non-opioid receptor mediated processes. Pharmazie. Sep. 1998;53(9):634-7.

Mickley et al., Quaternary naltrexone reverses morphine-induced behaviors. Physiol Behav. Aug. 1985;35(2):249-53.

(56) References Cited

OTHER PUBLICATIONS

Miedema et al., Methods for decreasing postoperative gut dysmotility. Lancet Oncol. Jun. 2003;4(6):365-72.
Misra et al., Intavenous kinetics and metabolism of [15,16-3H]naltrexonium methiodide in the rat. J Pharm Pharmacol. Mar. 1987;39(3):225-7.
Miyagi et al., Morphine induces gene expression of CCR5 in human CEMx174 lymphocytes. J Biol Chem. Oct. 6, 2000;275(40):31305-10.
Moerman et al., Evaluation of methylnaltrexone for the reduction of postoperative vomiting and nausea incidences. Acta Anaesthesiol Belg. 1995;46(3-4):127-32.
Moss, et al., Selective postoperative inhibition of gastrointestinal opioid receptors. N. Engl. J. Med. 2002;346(6):455.
Moss et al., Methylnaltrexone prevents morphine-induced CCR5 receptor expression. Anesthesiology. 2003;99. Abstract A-961.
Moss et al., Opioid-induced changes in pulmonary barrier integrity may explain heroid-induced pulmonary edema. American Society of Anesthesiologists presentation, Oct. 17, 2007 in San Francisco, CA. Abstract.
Moss et al., Pain relief without side effects: peripheral opiate antagonists. 33$^{rd}$ ASA Refresher Courses in Anesthesiology, Philadelphia, Lippincott Williams Wilkins, Schwartz, A.J. editor. 2006;33:175-86.
Mucha, Is the motivational effect of opiate withdrawal reflected by common somatic indices of precipitated withdrawal? A place conditioning study in the rat. Brain Res. Aug. 25, 1987;418(2):214-20.
Mucha, Taste aversion involving central opioid antagonism is potentiated in morphine-dependent rats. Life Sci. 1989;45(8):671-8.
Murphy et al., Pharmacokinetic profile of epidurally administered methylnaltrexone, a novel peripheral opioid antagonist in a rabbit model. Br J Anaesth. Jan. 2001;86(1):120-2.
Murphy et al., American Society of Anesthesiologists 1999 annual meeting. Dallas, Texas, USA. Oct. 9-13, 1999. Abstracts. Anesthesiology. Sep. 1999;91(3A Suppl):A349.
Murphy et al., Opioid-induced delay in gastric emptying: a peripheral mechanism in humans. Anesthesiology. Oct. 1997;87(4):765-70.
Murphy et al., Opioid antagonist modulation of ischaemia-induced ventricular arrhythmias: a peripheral mechanism. J Cardiovasc Pharmacol. Jan. 1999;33(1):122-5.
Nair et al., Morphine Modulates the Expression of Chemokines and their Receptors by Peripheral Blood Mononuclear Cells (PBMC) from Normal Donors. J Allergy Clin Immunol. 1998:101(1):S57. Abstract 244.
Naranjo et al., Evidence for a central but not adrenal, opioid mediation in hypertension induced by brief isolation in the rat. Life Sci. May 26, 1986;38(21):1923-30.
Nelson et al., Involvement of central mu- but not delta- or kappa-opioid receptors in immunomodulation, Brain Behav Immun. Sep. 2000;14(3):170-84.
Nielsen et al., Glycolamide Esters as Biolabile Prodrugs of Carboxylic Acid Agents: Synthesis, Stability, Biocenversion, and Physicochemical Properties. J Pharma Sci. 1988;77:285-98.
Nemeth-Lefkowitz et al., Research communication in Substances of Abuse (1980) 1(2): 177-83.
Neumann et al., Plasma morphine concentrations during chronic oral administration in patients with cancer pain. Pain. Jul. 1982;13(3):247-52.
Niemegeers et al., Difenoxine (R 15403), the active metabolite of diphenoxylate (R 1132). 2. Difneozine, a potent, orally active and safe antidiarrheal agent in rats. Arzneimittelforschung. Mar. 1972;22(3):516-8.
Novick et al., Natural killer cell activity and lymphocyte subsets in patenteral heroin abusers and long-term methadone maintenance patients. J Pharmacol Exp Ther. Aug. 1989;250(2):606-10.
Odio et al., Central but not peripheral opiate receptor blockade prolonged pituitary-adrenal responses to stress. Pharmacol Biochem Behav. Apr. 1990;35(4):963-9.
O'Keefe et al., Bowel Disorders Impair Functional Status and Quality of Life in the Elderly: A Population-Based Study. J Gerontol. 1995;50:184-89.
Osinski et al., Determination of methylnaltrexone in clinical samples by solid-phase extraction and high-performance liquid chromatography for a pharmacokinetics study. J Chromatogr B Analyt Technol Biomed Life Sci. Nov. 25, 2002;780(2):251-9.
Papapetropoulos et al., Nitric oxide synthase inhibitors attenuate transforming-growth-factor-beta 1-stimulated capillary organization in vitro. Am J Pathol. May 1997;150(5):1835-44.
Pappagallo, Incidence, prevalence, and management of opioid bowel dysfunction. Am J Surg. Nov. 2001;182(5A Suppl):11S-18S.
Pasi et al., Angiogenesis: modulation with opioids. Gen Pharmacol. 1991;22(6):1077-9.
Patel et al., Cox-2 and iNOS in opioid-induced delayed cardioprotection in the intact rat. Life Sci. May 28, 2004;75(2):129-40.
Paulson et al., Alvimopan: an oral, peripherally acting, mu-opioid receptor antagonist for the treatment of opioid-induced bowel dysfunction—a 21-day treatment-randomized clinical trial. J Pain. Mar. 2005;6(3):184-92.
Peart et al., Opioid-induced preconditioning: recent advances and future perspectives. Vascul Pharmacol. Apr.-May 2005;42(5-6):211-8. Epub Mar. 17, 2005.
Peeters et al., The motilin antagonist ANQ-11125 blocks motilide-induced contractions in vitro in the rabbit. Biochem Biophys Res Commun. Jan. 28, 1994;198(2):411-6. Abstract Only.
Peterson et al., Morphine promotes the growth of HIV-1 in human peripheral blood mononuclear cell cocultures. AIDS. Sep. 1900;4(9):869-73.
Pham et al., Drugs of Abuse: Chemistry, Pharmacology, Immunology and AIDS; National Institute of Drug Research 96: Monograph Series. U.S. Department of Health and Human Services; 1990.
Polak et al., Enkephalin-like immunoreactivity in the human gastrointestinal tract. Lancet. May 7, 1977;1(8019):972-4.
Polakiewicz et al., Mu-Opioid receptor activates signaling pathways implicated in cell survival and translational control, J Biol Chem. Sep. 4, 1998;273(36):23534-41.
Poonawala et al., Opioids heal ischemic wounds in the rat. Wound Repair Regen. Mar.-Apr. 2005;13(2):165-74.
Powell et al., Paradoxical effects of the opioid antagonist naltrexone on morphine analgesia, tolerance, and reward in rats. J Pharmacol. Exp Ther. Feb. 2002;300(2):588-96.
Pugsley et al., Cardiovascular actions of the kappa-agonist, U-50,488H, in the absence and presence of opioid receptor blockade. Br J Pharmacol. Mar 1992;105(3):521-6.
Quang-Contagrel el al., Long-term methadone treatment: effect on CD4+ lymphocyte counts and HIV-1 plasma RNA level in patients with HIV infection. Eur J Pain. 2001;5(4):415-20.
Quock, et al, Microwave facilitation of methylnaltrexone antagonism of morphine-induced analgesia in mice. J Bioelect. 1986;5(1):35-46.
Quock et al., Narcotic antagonist-induced hypotension in the spontaneously hypertensive rat. Life Sci. Sep. 2, 1985;37(9):819-26.
Quock et al., Narcotic antagonist-induced potentiation of apomorphine drug effect: a stereospecific, centrally mediated drug action. Prog Neuropsychopharmacol Biol Psychiatry. 1985;9(3):239-43.
Radulović et al., Opioid receptor-mediated suppression of humoral immune resonse in vivo and in vitro: involvement of kappa opioid receptors. J Neuroimmunol. Mar. 1995;57(1-2):55-62.
Ramabadran, Effects of N-methylnaloxone and N-methylnaltrexone on nociception and precipitated abstinence in mice. Life Sci. Sep. 20-27, 1982;31(12-13):1253-6.
Read et al., Interpretation of the breath hydrogen profile obtained after ingesting a solid meal containing unabsorbable carbohydrate. Gut. Aug. 1985;26(8):834-42.
Reisine et al., Opioid Analgesics and Anagonists. In: Goodman & Goodman's The Pharmacological Basis of Therapeutics, 9$^{th}$ Ed. 1996:521-55.
Resnick et al., Delayed gastric emptying and postoperative ileus after nongastric abdominal surgery: part I. Am J Gastroenterol. May 1997;92(5):751-62.
Resnick et al., Delayed gastric emptying and postoperative ileus after nongastric abdominal surgery: part II. Am J Gastroenterol. Jun. 1997;92(6):934-40.
Risdahl et al., Opiates and infection. J Neuroimmunol. Mar. 15, 1998;83(1-2):4-18.

(56) References Cited

OTHER PUBLICATIONS

Riviere et al., Fedotozine reverses ileus induced by surgery or peritonitis: action at peripheral kappa-opioid receptors. Gastroenterology. Mar. 1993;104(3):724-31.
Robinson et al., Oral naloxone in opioid-associated constipation. Lancet. Aug. 31, 1991;338(8766):581-2.
Roger et al., Colonic motor responses in the pony: relevance of colonic stimulation by opiate antagonists. Am J Vet Res. Jan. 1985;46(1):31-5.
Roy et al., Morphine modulates NF kappa B activation in macrophages. Biochem Biophys Res Commun. Apr. 17, 1998;245(2):392-6.
Russell el al., Antagonism of gut, but not central effects of morphine with quaternary narcotic antagonists. Eur J Pharmacol. Mar. 12, 1982;78(3):255-61.
Sachs et al., Peripheral analgesic blockade of hypernociception: activation of arginine/NO/cGMP/protein kinase G/ATP-sensitive K+ channel pathway. Proc Natl Acad Sci U S A. Mar. 9, 2004;101(10):3680-5. Epub Feb. 27, 2004.
Saffran et al., A new approach to the oral administration of insulin and other peptide drugs. Science. Sep. 5, 1986;233(4768):1081-4. Abstract Only.
Sakurada et al., Differential antagonism of endomorphin-1 and endomorphin-2 supraspinal antinociception by naloxonazine and 3-methylnaltrexone. Peptides. May 2002;23(5):895-901.
Sandner-Keisling et al., Pharmacology of opioid inhibition to noxious uterine cervical distension. Anesthesiology. Oct. 2002;97(4):966-71.
Sawhney et al., Bioerodible Hydrogels Based on Photopolymerized Poly(ethylene glycol)-co-poly(α-hydroxy acid) Diacrylate Macromers. Macromolecules. 1993;26:581-87.
Schaefer et al., Effects of opioid antagonists and their quaternary derivatives on locomotor activity and fixed ratio responding for brain self-stimulation in rats. Pharmacol Biochem Behav. Nov. 1985;23(5):797-802.
Schang et al., Beneficial effects of naloxone in a patient with intestinal pseudoobstruction. Am J Gastroenterol. Jun. 1985;80(6):407-11.
Schang et al., How does morphine work on colonic motility? An electromyographic study in the human left and sigmoid colon. Life Sci. Feb. 24, 1986;38(8):671-6.
Schiller et al., Studies of the mechanism of the antidiarrheal effect of codeine. J. Clin Invest. Nov. 1982;70(5):999-1008.
Schmidhammer, et al., Synthesis and biological evaluation of 14-alkoxymorphinans, Part 10[1]. 14-O-methyl derivatives of 5-methylnaltrexone and 5-methylnaloxone. Helv Chim Acta. 1994;77(6):1585-9.
Schmidhammer, et al., Synthesis and biological evaluation of 14-alkoxymorphinans. Part 9[1]. 14-O-ethyl-5-methylnaltrexone, an opioid antagonist with unusual selectivity. Helv Chim Acta. 1993;(1):476-80.
Schmidt et al., Alvimopan* (ADL 8-2698) is a novel peripheral opioid antagonist. Am J Surg. Nov. 2001;182(5A Suppl):27S-38S.
Scholz, Managing constipation that's opioid-induced. 2000; 63(6):103.
Schreier et al., Central regulation of intestinal function: morphine withdrawal diarrhea. Proc West Pharmacol Soc. 1982;25:151-4.
Schubert-Zsilavecz et al., Das reizdarmsyndrom irritable bowel syndrome. Deutsche apotheker zeitung. Aug. 22, 2002; 142(34); 40-9.
Schug et al., A long-term survey of morphine in cancer patients. J Pain Symptom Manage. Jul. 1992;7(5):259-66. Abstract Only.
Schuller et al., M6G, but not morphine, inhibits GI transit in mu opioid receptor deficient mice. Society of Neuroscience Abstracts. 1998;24:524. Abstract 210.7.
Sezen et al., Renal excretory responses produced by the delta opioid agonist, BW373U86, in conscious rats. J Pharmacol Exp Ther. Oct. 1998;287(1):238-45.
Shahbazian et al., Involvement of mu- and kappa-, but not delta-, opioid receptors in the peristaltic motor depression caused by endogenous and exogenous opioids in the guinea-pig intestine. Br J Pharmacol. Feb. 2002;135(3):741-50.
Shavit et al., Effects of a single administration of morphine or footshock stress on natural killer cell cytotoxicity. Brain Behav Immun. Dec. 1987;1(4):318-28.
Shi et al., Cardioprotective effects of morphine on rat heart suffering from ischemia and reperfusion. Chin Med J (Engl). Jul. 2003;116(7):1059-62.
Simonin et al., Kappa-Opioid receptor in humans: cDNA and genomic cloning, chromosomal assignment, functional expression, pharmacology, and expression pattern in the central nervous system.. Proc Natl Acad Sci U S A. Jul. 1995;92(15):7006-10.
Simonin et al., The human delta-opioid receptor: genosmc organization, cDNA cloning, functional expression, and distribution in human brain. Mol Pharmacol. Dec. 1994;46(6):1015-21. Abstract Only.
Soldani et al., Central and peripheral involvement of mu receptors in gastric secretory effects of opioids in the dog. Eur J Pharmacol. Nov. 19, 1985;117(3):295-301.
Solvason et al., Naltrexone blocks the expression of the conditioned elevation of natural killer cell activity in BALB/c mice. Brain Behav Immun. Sep. 1989;3(3)247-62.
Stankski et al., Kinetics of intravenous and intramuscular morphine. Clin Pharmacol Ther. Jul. 1978;24(1):52-9.
Steele et al., HIV-1 Infection and Opioid Administration Modulate the Expression of Chemokine Receptors. Drug and Alcohol Dependence. 2000:60(Supp 1):S212. Abstract 599.
Stefano et al., Delta2 opioid receptor subtype on human vascular endothelium uncouples morphine stimulated nitric oxide release. Int J Cardiol. Apr. 30, 1998;64 Suppl 1:S43-51.
Stefano et al., Long-term exposure of human blood vessels to HIV gp120, morphine, and anandamide increases endothelial adhesion of monocytes: uncoupling of nitric oxide release. J Cardiovasc Pharmacol. Jun. 1998;31(6):862-8.
Stefano et al., Morphine enhances nitric oxide release in the mammalian gastrointestinal tract via the micro(3) opiate receptor subtype: a hormonal role for endogenous morphine. J Physiol Pharmacol. Mar. 2004;55(1 Pt 2):279-88.
Stefano et al., Presence of the mu3 opiate receptor in endothelial cells. Coupling to nitric oxide prouction and vasodilation. J Biol Chem. Dec. 22, 1995;270(51):30290-3.
Steinbrook et al., An opioid antagonist for postoperative ileus. N Engl J Med. Sep. 27, 2001;345(13):988-9.
Stephenson el al., Methylnaltrexone reverses opioid-induced constipation. Lancet Oncol. Apr. 2002;3(4):202.
Sternini et al., The opioid system in the gastrointestinal tract. Neurogastroenterol Motil. Oct. 2004;16 Suppl 2:3-16.
Stewart et al., Central and peripheral actions of morphine on intestinal transit. J Pharmacol Exp Ther. Jun. 1978;205(3):547-55.
Stiene-Martin et al., Regional, developmental, and cell cycle-dependent differences in mu, delta, and kappa-opioid receptor expression among cultured mouse astrocytes. Glia, Mar. 1998;22(3):249-59.
Suzuki et al., Morphine suppresses lymphocyte apoptosis by blocking p53-mediated death signaling. Biochem Biophys Res Commun. Sep. 5, 2003;308(4):802-8.
Swan, et al., NIDA plays key role in studying links between AIDS and drug abuse. AIDS Research, NIDA Notes. 1995; 10(3):1-6.
Sykes, Oral naloxone in opioid-associated constipation. Lancet. Jun. 15, 1991;337(8755):1475.
Sykes, Chapter 9. Using oral naloxone in management of opioid bowel dysfunction. Handbook of Opioid Bowel Syndrome, New York, Haworth Medical Press, Yuan, C-S editor. 2005:175-95.
Szabo et al., Interactions of opioid receptors, chemokines, and chemokine receptors. Adv Exp Med Biol. 2001;493:69-74.
Taguchi et al., Selective postoperative inhibition of gastrointestinal opioid receptors. N Engl J Med. Sep. 27, 2001;345(13):935-40.
Talley et al., Pharmacologic therapy for the irritable bowel syndrome. Am J Gastroenterol. Apr. 2003;98(4):750-8.
Tavani et al., Morphine is most effective on gastrointestinal propulsion in rats by intraperitoneal route: evidence for local action. Life. Sci. Dec. 8, 1980;27(23):2211-7.
Tegeder et al., Opioids as modulators of cell death and survival—unraveling mechanisms and revealing new indications. Pharmacol Rev. Sep. 2004;56(3):351-69.
Thomas et al., A phase III double-blind placebo-controlled trial of methylnaltrexone (MNTX) for opioid-induced constipation (OIC) in

(56) References Cited

OTHER PUBLICATIONS advanced medical illness (AMI). Abstract No. LBA8003 from the 2005 ASCO Annual Meeting. 3 pages.
Thomas et al., Amelioration of peripheral side effects of opioids: clinical experience with methylnaltrexone (MNTX). Proc World Congr Anesth. 2004:107. Abstract Only.
Thompson et al., Opioid stimulation in the ventral tegmental area facilitates the onset of maternal behaviror in rats. Brain Res. Dec. 16, 1996;743(1-2):184-201.
Thompson et al., Laxatives: clinical pharmacology and rational use. Drugs. Jan. 1980;19(1):49-58.
Tomiyasu et al., Analysis of intercostal nerve damage associated with chronic post-thoracotomy pain. Anesthesiology. 2001;95. Abstract A-964.
Tryoen-Toth et al., Regulation of kappa-opioid receptor mRNA level by cyclic AMP and growth factors in cultured rat glial cells. Brain Res Mol Brain Res. Mar. 30, 1998;55(1):141-50.
Ukai et al., Suppression of deprivation-induced water intake in the rat by opioid antagonists: central sites of action. Psychopharmacology (Berl). 1987;91(3):279-84.
Uwai et al., Syntheses and receptor-binding studies of derivatives of the opioid antagonist naltrexone. Bioorg Med Chem. Jan. 15, 2004;12(2):417-21.
Valentino et al., Quaternary naltrexone: evidence for the central mediation of discriminative stimulus effects of narcotic agonists and antagonists. J Pharmacol Exp Ther. Jun. 1981;217(3):652-9.
Valentino et al., Receptor binding, antagonist, and withdrawal precipitating properties of opiate antagonists. Life Sci. Jun. 20, 1983;32(25):2887-96.
Vallejo et al., Opioid therapy and immunosuppression: a review. Am J Ther. Sep.-Oct. 2004;11(5):354-65.
Vaughan et al., Human antibodies by design. Nat Biotechnol. Jun. 1998;16(6):535-9.
Vermiere et al., Stability and compatibility of morphine. International Journal of Pharmaceutics 1999;187:17-51.
Waldhoer et al., Opioid receptors. Aunnu Rev Biochem. 2004;73:953-90.
Walker, et al., Role of central versus peripheral opioid receptors in analgesia induced by repeated administration of opioid antagonists. Psychopharmacology. 1991;104(2):164-6.
Walsh et al., The symptoms of advanced cancer: relationship to age, gender, and performance status in 1,000 patients. Support Care Cancer. May 2000;8(3):175-9. Abstract Only.
Wang et al., A non-peptide substance P antagonist (CP-96,345) inhibits morphine-induced NF-kappa B promoter activation in human NT2-N neurons. J Neurosci Res. Feb. 15, 2004;75(4):544-53.
Wang et al., Determination of tungsten in bulk drug substance and intermediates by ICP-AES and ICP-MS. J Pharm Biomed Anal. May 1999;19(6):937-43. Abstract Only.
Wang et al., Human mu opiate receptor. cDNA and genomic clones, pharmacologic characerization and chromosomal assignment. FEBS Lett Jan. 31, 1994;338(2);217-22. Abstract Only.
Wang et al., Mobilization of calcium from intracellular stores as one of the mechanisms underlying the antiopioid effect cholecystokinin octapeptide. Peptides. Sep.-Oct. 1992;13(5):947-51.
Wang et al., Morphine negatively regulates interferon-gamma promoter activity in activated murine T cells through two distinct cyclic AMP-dependent pathways. J Biol Chem. Sep. 26, 2003;278(39):37622-31. Epub Jul. 3, 2003.
Wang et al., The immunosuppressive effects of chronic morphine treatment are partially dependent on corticosterone and mediated by the mu-opioid receptor. J Leukoc Biol. May 2002;71(5):782-90.
Warren et al., Effects of quaternary naltrexone and chlordiazepoxide in squirrel monkeys with enhanced sensitivity to the behavioral effects of naltrexone. J Pharmacol Exp. Ther. Nov. 1985;235(2):412-7.
Wei et al., Abstracts of the 2002 Annual Meeting of the American Society for Clinical Pharmacology and Therapeutics. Atlanta, Georgia, USA. Mar. 24-27, 2002. Clin Pharmacol. Ther. Feb. 2002;71(2):p. 1-136.
Wei et al., Opioid-induced immunosuppression: is it centrally mediated or peripherally mediated? Biochem Pharmacol. Jun. 1, 2003;65(11):1761-6.
Wei et al., Pharmacokinetics of subcutaneous methylnaltrexone: different route administration comparison. 2001. ASA Annual Meeting Abstracts. Oct. 14-18, 2001. Chicago, IL. Abstract A-962.
Wentland et al., Synthesis and opioid receptor binding properties of a highly potent 4-hydroxy analogue of naltrexone. Bioorg Med Chem Lett. Apr. 15, 2005;15(8):2107-10.
Whistler et al., Functional dissociation of mu opioid receptor signaling and endocytosis: implications for the biology of opiate tolerance and addiction. Neuron. Aug. 1999;23(4):737-46.
Willett et al., Direct evidence that the VEGF-specific antibody bevacizumab has antivascular effects in human rectal cancer, Nat Med. Feb. 2004;10(2):145-7. Epub Jan. 25, 2004.
Willette, et al., Evidence for anticholinergic effects of naltrexone methylbromide. Res Comm Subst Abuse. 1983;4(4):325-37.
Wilmore et al., Can we minimize the effects of opioids on the bowel and still achieve adequate pain control? Am J Surg. Nov. 2001;182(5A Suppl):1S-2S.
Wingo et al., Cancer statistics, 1995. CA Cancer J Clin. Jan.-Feb. 1995;45(1):8-30.
Witkin et al., Pharmacology of 2-amino-indane hydrochloride (Su-8629): a potent non-narcotic analgesic. J Pharmacol Exp Ther. Sep. 1961;133:400-8. Abstract Only.
Wittert et al., Tissue distribution of opioid receptor gene expression in the rat. Biochem Biophys Res Commun. Jan. 26, 1996;218(3):877-81.
Wolff et al., Alvimopan, a novel, peripherally acting mu opioid antagonist: results of a multicenter, randomized, double-blind, placebo-controlled, phase III trial of major abdominal surgery and postoperative ileus. Ann surg. Oct. 2004;240(4):728-34; discussion 734-5.
Wybran et al., Suggestive evidence for receptors for morphine and methionine-enkephalin on normal human blood T lymphocytes. J Immunol. Sep. 1979;123(3):1068-70.
Yamamoto et al., Inhibition of stress-stimulated colonic propulsion by alpha 2-adrenoceptor antagonists in rats. Neurogastroenterol Motil. Dec. 1998;10(6):523-32. Abstract Only.
Yeh et al., Stability of morphine in aqueous solution. Am J Hosp Pharmacy. 1960;17(2):101-103.
Yoshida et al., Effect of sugical stress on endogenous morphine and cytokine levels in the plasma after laparoscopoic or open cholecystectomy. Surg Endosc. Feb. 2000;14(2):137-40.
Yuan et al., Antagonism of chronic opioid-induce gut effects. Anesth Analg. 2000;90:S1-523. Abstract S479.
Yuan et al., Antagonism of gastrointestinal opioid effects. Reg Anesth Pain Med. Nov.-Dec. 2000;25(6):639-42.
Yuan et al., Clinical status or methylnaltrexone, a new agent to prevent and manage opioid-induced side effects. J Support Oncol, Mar.-Apr. 2004;2(2):111-7; discussion 119-22.
Yuan et al., Dose-related effects of oral acetaminophen on cold-induced pain: a double-blind, randomized, placebo-controlled trial. Clin Pharmacol Ther. Mar. 1998;63(3):379-83.
Yuan et al., Effects of enteric-coated methylnaltrexone in preventing opioid-induced delay in oral-cecal transit time. Clin Pharmacol Ther. Apr. 2000;67(4):398-404.
Yuan et al., Effects of intravenous methylnaltrexone on opioid-induced gut motility and transit time changes in subjects receiving chronic methadone therapy: a pilot study. Pain. Dec. 1999;83(3):631-5.
Yuan et al., Effects of low-dose morphine on gastric emptying in healthy volunteers. J Clin Pharmacol. Nov. 1993;38(II):1017-20.
Yuan et al., Effects of methylnatrexone on chronic optioid induced gut motility and transit time changes. Br J Anaesth. 1998;81(1):94. Abstract Only.
Yuan et al., Effects of methylnaltrexone on chronic opioid-induced gut motility and transit time changes. University of Leicester—Abstracts from the Eighth International Symposium on Pain, Anaesthesia and Endocrinology. Sep. 18-19, 1997.
Yuan et al., Effects of methylnaltrexone on morphine-induced inhibition of contractions in isolated guinea-pig and human intestine. Anesthesiology. Sep. 1995; 83(3A). Abstract A358.

(56) References Cited

OTHER PUBLICATIONS

Yuan et al., Effects of methylnaltrexone on morphine-induced inhibition of contractions in isolated guinea-pig ileum and human intestine. Eur J Pharmacol. Mar. 24, 1995;276(1-2):107-11.
Yuan et al., Effects of subcutaneous methylnaltrexone on morphine-induced peripherally mediated side effects: a double-blind randomized placebo-controlled trial. J Pharmacol Exp Ther. Jan. 2002;300(1):118-23.
Yuan et al., Efficacy of orally administered methylnaltrexone in decreasing subjective effects after intravenous morphine. Drug Alcohol Depend. Oct. 1, 1998;52(2):161-5.
Yuan et al., Gastric effects of methylnaltrexone on mu, kappa, and delta opioid agonists induced brainstem unitary responses. Neuropharmacology. Mar. 1999;38(3):425-32.
Yuan et al., Gastric effects of mu-, delta- and kappa-opioid receptor agonists on brainstem unitary responses in the neonatal rat. Eur J Pharmacol. Oct. 24, 1996;314(1-2):27-32.
Yuan et al., Gut and brain effects of American ginseng root on brainstem neuronal activities in rats. Amer J Chin Med. 1998; 26: 47-55.
Yuan et al., Gut motility and transit changes in patients receiving long-term methadone maintenance. J Clin Pharmacol. Oct. 1998;38(10):931-5.
Yuan et al. Methylnaltrexone, a novel peripheral opioid receptor antagonist for the treatment of opioid side effects. Expert Opin Investig Drugs. May 2006;15(5):541-52.
Yuan et al., Methylnaltrexone (MNTX) for chronic opioid-induced constipation. 2002 ASCO Annual Meeting. Proc Am Soc Clin Oncol. 2002;21:376a. Abstract 1501.
Yuan et al., Methylnaltrexone (MNTX) reverses chronic opioid constipation: a double-blind, randomized, placebo-controlled trial. Anesthesiology. Sep. 1999; 91 (3A). Abstract A973.
Yuan et al., Methylnaltrexone changes gut motility and transit time in chronic methadone-maintained subjects. Anesth Anal. 1999;88: S1-424. Abstract S404.
Yuan et al., Methylnaltrexone effects on morphine-induced inhibition in isolated guinea-pig and human intestine. Clin Pharm & Therapeut. Feb. 1995;57:138. Abstract PI-II.
Yuan el al., Methylnaltrexone for reversal of constipation due to chronic methadone use: a randomized controlled trial. JAMA. Jan. 19, 2000;283(3):367-72.
Yuan et al., Methylnaltrexone prevents morphine-induced delay in oral-cecal transit time without affecting analgesia: a double-blind randomized placebo-controlled trial. Clin Pharmacol Ther. Apr. 1996;59(4):469-75.
Yuan et al., Methylnaltrexone prevents morphine-induced kaolin intake in the rat. Anesthesiology. 2003;99. Abstract A-922.
Yuan et al., Methylnaltrexone reduces oral-cecal transit time in humans. Dig Dis Week Abstr. 2003:A-578, Abstract T1840.
Yuan et al., Methylnaltrexone reverses morphine-induced changes in gastrointestinal motility: a clinical study. Anesthesiology Sep. 1995; 83(3A): Abstract A360.
Yuan et al., Methylnaltrexone: investigation of clinical applications. Drug Develop Res. 2000;50(2):133-41.
Yuan et al., Opioid anagesia without gut side effects: effects of methylnaltrexone as a novel peripheral opioid antagonist. Assoc Univ Anesth Abst. 2003: PD2.
Yuan et al., Oral methylnaltrexone for opioid-induced constipation. JAMA. Sep. 20, 2000;284(11):1383-4.
Yuan et al., Oral methylnaltrexone reverses chronic opioid-induced constipation. Anesthesiology. Sep. 2000;93(3A). Abstract A-872.
Yuan et al., Oral methylnaltrexone reverses morphine-induced changes in gastrointestinal motility. Anesthesiology. Sep. 1995;85(3A). Abstract A335.
Yuan et al., Pain control without side effects: clinical studies on methylnaltrexone as a novel peripheral opioid antagonist, 7th America-Japan Anesth Congr. Yamanashi, Japan. 2002:41.
Yuan et al., Pharmacokinetics of intravenous vs. oral methylnaltrexone: evidence for direct gut effects. Anesth Analg. 2001;92: S1-363. Abstract S274.
Yuan et al. Safety and tolerance of oral methylnaltrexone in healthy volunteers. Anesth Analg. 1997;84:S1-599. Abstract S574.
Yuan et al., Subcutaneous methylnaltrexone prevents morphine-induced delay in gut transit time: a clinical trial. Anesthesiology. 2001;95. Abstract A-963.
Yuan et al., The safety and efficacy of oral methylnaltrexone in preventing morphine-induced delay in oral-cecal transit time. Clin Pharmacol Ther. Apr. 1997;61(4):467-75.
Yuan et al., Tolerability, gut effects, and pharmacokinetics of methylnaltrexone following repeated intravenous administration in humans. J Clin Pharmacol. May 2005;45(5):538-46.
Zagon et al., Opioids and differentiation in human cancer cells. Neuropeptides. Oct. 2005;39(5):495-505. Epub Sep. 15, 2005.
Zagon et al., Opioids and the apoptotic pathway in human cancer cells. Neuropeptides. Apr. 2003;37(2):79-88.
Zagon et al., Opioid antagonists inhibit the growth of metastatic murine neuroblastoma. Cancer Lett. Nov. 1983;21(1):89-94.
Zagon et al., Opioid growth factor regulates the cell cycle of human neoplasias. Int J Oncol. Nov. 2000;17(5):1053-61.
Zhang et al., Dynorphin A as a potential endogenous ligand for four members of the opioid receptor gene family. J Pharmacol Exp Ther. Jul. 1998;286(1):136-41.
Zhang et al., Effect of the endogenous kappa opioid agonist dynorphin A(1-17) on cocaine-evoked increases in striatal dopamine levels and cocaine-induced place preference in C57BL/6J mice. Psychopharmacology (Berl). Apr. 2004;172(4):422-9. Epub Jan. 8, 2004.
Zimmerman et al., Discovery of a potent, peripherally selective trans-3,4-dimethyl-4-(3-hydroxyphenyl) piperidine opioid antagonist for the treatment of gastrointestinal motility disorders. J Med Chem. Jul. 22, 1994, 37(15):2262-5.
Burks, T.F. et al. Regulation of gastrointestinal function by multiple opioid receptors. Life Sciences 1988; 43:2177-2181.
Kromer, W. Unexpected prosecretory action component of loperamide at µ-opioid receptors in the guinea-pig colonic mucosa in vitro. British J Pharmacology 1995; 114:739-744.
Lesbros-Pantoflickova, D. et al. Meta-analysis: the treatment of irritable bowel syndrome. Aliment Pharmacol Ther 2004; 20:1253-1269.
Philippe, D. et al. Anti-inflammatory properties of the µ opioid receptor support its use in the treatment of colon inflammation. J Clinical Investigation 2003; 11:1329-1338.
Ragnarsson G. et al. Treatment of irritable bowel syndrome with loperamide oxide. An open study to determine optimal dosage. J Internal Medicine 2000; 248:165-169.
Tegeder I. et al. Peripheral opioid analgesia in experimental human pain models. Brain 2003; 126:1092-1102.
The Second Office Action, Issued by the State Intellectual Property Office of the People's Republic of China on Jan. 15, 2013 in Chinese Patent Application 200680022964.X citing You, Q. and Lin, G., Chiral Drugs—Study and Application. Chemical Industry Press, First Edition, Jan. 2004, pp. 510-517, China.

\* cited by examiner

1 - OXYCODONE
2 - OXYMORPHONE
3 - IODIDE SALT OF S-MNTX

(S)-N-METHYLNALTREXONE

RELATED APPLICATIONS

The present application is a continuation of U.S. application Ser. No. 12/460,507, filed Jul. 20, 2009, which is a divisional of U.S. application Ser. No. 11/441,452, filed May 25, 2006, which claims priority to U.S. Provisional Application No. 60/684,570, filed May 25, 2005, the entire contents of each of which are hereby incorporated by reference herein.

FIELD OF THE INVENTION

This invention relates to (S)-N-methylnaltrexone (S-MNTX), stereoselective synthetic methods for the preparation of S-MNTX, pharmaceutical preparations comprising S-MNTX and methods for their use.

BACKGROUND OF INVENTION

Methylnaltrexone (MNTX) is a quaternary derivative of the pure opioid antagonist, naltrexone. It exists as a salt. Names used for the bromide salt of MNTX in the literature include: Methylnaltrexone bromide; N-Methylnaltrexone bromide; Naltrexone methobromide; Naltrexone methyl bromide; MRZ 2663BR. MNTX was first reported in the mid-70s by Goldberg et al as described in U.S. Pat. No. 4,176,186. It is believed that addition of the methyl group to the ring nitrogen forms a charged compound with greater polarity and less liposolubility than naltrexone. This feature of MNTX prevents it from crossing the blood-brain barrier in humans. As a consequence, MNTX exerts its effects in the periphery rather than in the central nervous system with the advantage that it does not counteract the analgesic effects of opioids on the central nervous system.

MNTX is a chiral molecule and the quaternary nitrogen can be in R or S configuration. (See FIG. 1.) It is unknown whether the different stereoisomers of MNTX exhibit different biological and chemical properties. All of the reported functions of MNTX described in the literature indicate that MNTX is a peripheral opioid antagonist. Some of these antagonist functions are described in U.S. Pat. Nos. 4,176,186, 4,719,215, 4,861,781, 5,102,887, 5,972,954, 6,274,591, 6,559,158, and 6,608,075, and in U.S. patent application Ser. No. 10/163,482 (2003/0022909A1), Ser. No. 10/821,811 (20040266806), Ser. No. 10/821,813 (20040259899) and Ser. No. 10/821,809 (20050004155). These uses include reducing the side-effects of opioids without reducing the analgesic effect of opioids. Such side-effects include nausea, emesis, dysphoria, pruritus, urinary retention, bowel hypomotility, constipation, gastric hypomotility, delayed gastric emptying and immune suppression. The art discloses that MNTX not only reduces the side-effects stemming from opioid analgesic treatment but also reduces the side-effects mediated by endogenous opioids alone or in conjunction with exogenous opioid treatment. Such side-effects include inhibition of gastrointestinal motility, post-operative gastrointestinal dysfunction, idiopathic constipation and other such conditions including, but not limited to, those mentioned above. However, it is unclear from the art whether the MNTX used in these studies was a mixture of R and S stereoisomers or a single stereoisomer.

The art suggests that isolated stereoisomers of a compound sometimes may have contrasting physical and functional properties, although it is unpredictable whether this is the case in any particular circumstance. Dextromethorphan is a cough suppressant, whereas its enantiomer, levomethorphan, is a potent narcotic. R,R-methylphenidate is a drug to treat attention deficit hyperactivity disorder (ADHD), whereas its enantiomer, S,S-methylphenidate is an antidepressant. S-fluoxetine is active against migraine, whereas its enantiomer, R-fluoxetine is used to treat depression. The S enantiomer of citalopram is therapeutically active isomer for treatment of depression. The R enantiomer is inactive. The S enantiomer of omeprazole is more potent for the treatment of heartburn than the R enantiomer.

Bianchetti et al, 1983 *Life Science* 33 (Sup I):415-418 studied three pairs of diastereoisomers of quaternary narcotic antagonist and their parent tertiary amines, levallorphan, nalorphine, and naloxone, to see how the configuration about the chiral nitrogen affected in vitro and in vivo activity. It was found that the activity varied considerably depending on how the quaternary derivatives were prepared. In each series, only the diastereomer obtained by methylation of the N-allyl-substituted tertiary amine (referred to as "N-methyl diastereomer") was potent in displacing $^3$H-naltrexone from rat brain membranes, and acting as a morphine antagonist in the guinea-pig ileum. Conversely, diastereoisomers obtained by reacting N-methyl-substituted tertiary amines with allyl halide (referred to as "N-allyl diastereomers") did not displace 3H-naltrexone and had negligible antagonist activity and slight agonist action in the guinea-pig ileum. In vivo findings were generally consistent with those in vitro. Thus only the "N-methyl" but not the "N-allyl diastereomers" inhibited morphine-induced constipation in rats and behaved as antagonists. The author stated that the prepared materials appeared to be pure by $^1$H and $^{13}$C nuclear magnetic resonance (NMR) analysis, but these methods are not accurate. The author cites a literature reference for the assignment of the R configuration to the "N-methyl diastereomer" of nalorphine. No assignment is proposed for the levallorphan and naloxone diastereomers. It would be adventurous to extrapolate the configuration to these diastereomers (R. J. Kobylecki et al, J. Med. Chem. 25, 1278-1280, 1982).

Goldberg et al.'s U.S. Pat. No. 4,176,186, and more recently Cantrell et al.'s WO 2004/043964 A2 describe a protocol for the synthesis of MNTX. Both describe a synthesis of MNTX by quaternizing a tertiary N-substituted morphinan alkaloid with a methylating agent. Both Goldberg et al. and Cantrell et al. are silent as to the stereoisomer(s) produced by the synthesis. The authors remained cautiously silent about the stereochemistry because the stereochemistry could not be determined based on prior art. The cyclopropylmethyl side-chain in naltrexone is different from the prior art side-chains and may have affected the stereochemical outcome in the synthesis of MNTX, as may other reaction parameters such as temperature and pressure. Based on the method of synthesis described in each, it is unknown whether the MNTX so produced was R, S or a mixture of both.

S-MNTX in pure form, and a method of making pure S-MNTX have not been described in the literature. Researchers would have been unable to definitively characterize and distinguish the stereoisomer(s) obtained by the. Goldberg et al. or Cantrell et al. synthesis-in the absence of S-MNTX as a standard.

SUMMARY OF THE INVENTION

S-MNTX has now been produced in high purity, permitting the characterization of its relative retention time in chromatography versus that of (R)-N-methylnaltrexone (R-MNTX). S-MNTX has been found to have activity different from the activity of MNTX reported in the literature.

The present invention provides highly pure S-MNTX, crystals of highly pure S-MNTX and intermediates thereof, novel methods for making highly pure S-MNTX, methods for analyzing S-MNTX in a mixture of R-MNTX and S-MNTX, methods of distinguishing R-MNTX from S-MNTX, methods of quantifying S-MNTX, pharmaceutical products containing the same and related uses of these materials.

S-MNTX, and salts thereof are provided. A protocol for obtaining S-MNTX was unpredictable from the prior art. In addition, it has been discovered, surprisingly, that S-MNTX has opioid agonist activity.

According to one aspect of the invention, a composition is provided. The composition is an isolated compound of the S configuration with respect to nitrogen of Formula I:

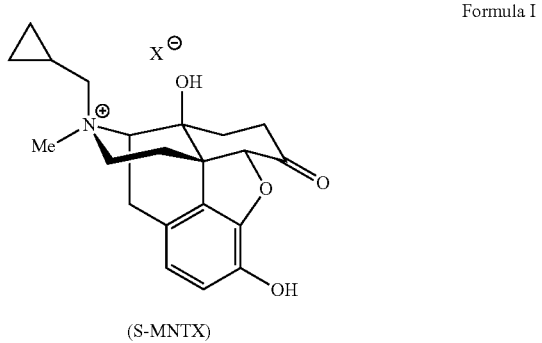

Formula I (S-MNTX)

to wherein X is a counterion.

S-MNTX is a salt. Therefore, there will be a counterion, which for the present application, includes the zwitterion. More typically, the counterion is a halide, sulfate, phosphate, nitrate, or anionic-charged organic species. Halides include fluoride, chloride, iodide and bromide. In some important embodiments, the halide is iodide and in other important embodiments the halide is bromide. In some embodiments the anionic-charged species is a sulfonate or a carboxylate. Examples of sulfonates include mesylate, besylate, tosylate, and triflate. Examples of carboxylates include formate, acetate, citrate, and fumarate.

According to the invention, S-MNTX is provided in isolated form. By isolated, it is meant at least 50% pure. In important embodiments, S-MNTX is provided at 75% purity, at 90% purity, at 95% purity, at 98% purity, and even at 99% purity or above. In one important embodiment, the. S-MNTX is in a crystal form.

According to another aspect of the invention, a composition is provided. The composition is MNTX, wherein the MNTX present in the composition is greater than 10% in S configuration with respect to nitrogen. More preferably, the MNTX present in the composition is greater than 30%, 40%, 50%, 60%, 70%, 75%, 80%, 85%, 90%, 95%, 96%, 97%, 98%, 98.5%, 99%, 99.5%, 99.6%, 99.7%, 99.8%, and even 99.9% in S configuration with respect to nitrogen. In some embodiments there is no detectable R-MNTX as measured by high performance liquid chromatography (HPLC).

The composition in some embodiments is a solution, in others an oil, in others a cream, and in still others a solid or semi-solid. In one important embodiment, the composition is a crystal.

According to another aspect of the invention, a pharmaceutical preparation is provided. The pharmaceutical preparation includes any one of the compositions of S-MNTX described above in a pharmaceutically acceptable carrier. The pharmaceutical preparation contains a effective amount of S-MNTX. In some embodiments, there is little or no detectable R-MNTX in the composition. If present, R-MNTX is at a level such that effective amounts of S-MNTX are administered to a subject. In some embodiments, the pharmaceutical preparation further includes a therapeutic agent other than MNTX. In one embodiment, the therapeutic agent is an opioid or opioid agonist. Examples of opioids or opioid agonists are alfentanil, anileridine, asimadoline, bremazocine, burprenorphine, butorphanol, codeine, dezocine, diacetylmorphine (heroin), dihydrocodeine, diphenoxylate, fedotozine, fentanyl, funaltrexamine, hydrocodone, hydromorphone, levallorphan, levomethadyl acetate, levorphanol, loperamide, meperidine (pethidine), methadone, morphine, morphine-6-glucuronide, nalbuphine, nalorphine, opium, oxycodone, oxymorphone, pentazocine, propiram, propoxyphene, remifentanyl, sufentanil, tilidine, trimebutine, tramadol, or combinations thereof. In some embodiments, the opioid or opioid agonist does not readily cross the blood brain barrier and, therefore, has substantially no central nervous system (CNS) activity when administered systemically (i.e., it is of the class of agents known as "peripherally acting") agents. In other embodiments the therapeutic agent is an opioid antagonist. Opioid antagonists include peripheral mu opioid antagonists. Examples of peripheral mu opioid antagonists include quaternary derivatives of noroxymorphone (See Goldberg et al, U.S. Pat. No. 4,176,186, and Cantrell et al WO 2004/043964), piperidine N-alkylcarboxylates such as described in U.S. Pat. Nos. 5,250,542; 5,434,171; 5,159,081; 5,270,328; and 6,469,030, opium alkaloid derivatives such as described in U.S. Pat. Nos. 4,730,048; 4,806,556; and 6,469,030, quaternary benzomorphan compounds such as described in U.S. Pat. Nos. 3,723,440 and 6,469,030.

In one embodiment, the peripheral opioid antagonist is R-MNTX. R-MNTX is the predominant form of MNTX following the manufacturing procedures described in the prior art, although it is believed that such preparations are contaminated with S-MNTX. Pure R-MNTX can be synthesized using the following protocol. In brief, stereoselective synthesis of R-MNTX is carried out by adding a hydroxyl protecting group to naltrexone to yield 3-O-protected-naltrexone; methylating the 3-O-protected-naltrexone to yield 3-O-protected-R-MNTX salt; and removing hydroxyl protecting group to yield R-MNTX. The hydroxyl protecting group can be added in the presence of each or both: an organic solvent, e.g. tetrahydrofuran, and/or a tertiary amine that is not naltrexone, e.g. triethylamine. The naltrexone can be methylated by reacting the 3-O-protected-naltrexone with methyl iodide to produce 3-O-protected-R-MNTX iodide salt. Naltrexone can be protected by a hydroxyl protecting group such as isobutyryl. The 3-O-protected-R-MNTX iodide salt can be treated with hydrobromic acid to remove the protecting group and produce R-MNTX bromide/iodide salt, and the bromide/iodide salt can be passed through an anion exchange resin column (bromide form) to yield R-MNTX bromide.

In other embodiments, the therapeutic agent is not an opioid, opioid agonist, or an opioid antagonist. For example, the therapeutic agent can be an antiviral agent, antibiotic agent, antifungal agent, antibacterial agent, antiseptic agent, anti-protozoal agent, anti-parasitic agent, anti-inflammatory agent, a vasoconstrictor agent, a local anesthetic agent, an anti-diarrheal agent, an anti-hyperalgesia agent, or combinations thereof.

In one aspect of the invention, the S-MNTX is combined with an anti-diarrhea agent that is loperamide, loperamide analogs, N-oxides of loperamide and analogs, metabolites and prodrugs thereof, diphenoxylate, cisapride, antacids, aluminum hydroxide, magnesium aluminum silicate, magnesium carbonate, magnesium hydroxide, calcium carbonate, polycarbophil, simethicone, hyoscyamine, atropine, furazolidone, difenoxin, octreotide, lansoprazole, kaolin, pectin, activated charcoal, sulphaguanidine, succinylsulphathiazole, phthalylsulphathiazole, bismuth aluminate, bismuth subcarbonate, bismuth subcitrate, bismuth citrate, tripotassium dicitrato bismuthate, bismuth tartrate, bismuth subsalicylate, bismuth subnitrate and bismuth subgallate, opium tincture (paregoric), herbal medicines, plant-derived anti-diarrheal agents or combinations thereof.

In one aspect of the invention, the S-MNTX is combined with an anti-inflammatory agent that is a non-steroidal anti-inflammatory drug (NSAID), a tumor necrosis factor inhibitor, basiliximab, daclizumab, infliximab, mycophenolate, mofetil, azothioprine, tacrolimus, steroids, sulfasalazine, olsalazine, mesalamine, or combinations thereof.

The pharmaceutical preparations of the invention can take on a variety of forms, including, but not limited to a composition that is enteric coated, a composition that is a controlled release or sustained release formulation, a composition that is a solution, a composition that is a topical formulation, a composition that is a suppository, a composition that is lyophilized, a composition that is in an inhaler, a composition that is in a nasal spray device, and the like. The composition can be for oral administration, parenteral administration, mucosal administration, nasal administration, topical administration, ocular administration, local administration, etc. If parenteral, the administration can be subcutaneous, intravenous, intradermal, intraperitoneal, intrathecal, etc.

According to another aspect of the invention, a method for synthesizing S-MNTX salt is provided. The method involves combining (iodomethyl) cyclopropane with oxymorphone in a first solvent to produce an iodo salt of S-MNTX. Counterions then may be substituted, optionally, for iodide by transferring the iodo salt S-MNTX to a second solvent and exchanging iodide for a counterion other than iodide. In one important embodiment, the iodo salt of S-MNTX is transferred from the first solvent to a second solvent, and the iodide is exchanged in the second solvent for bromide to produce a bromo salt of S-MNTX. The preferred first solvent is a dipolar aprotic solvent. Most preferred is N-methylpyrrolidone (NMP). The preferred second solvent is at least isopropyl acetate or dioxane. The method of the invention also involves purifying the salt of S-MNTX by chromatography, recrystallization, or a combination thereof. In one embodiment, the purification is by multiple recrystallizations. The reaction can be carried out across a wide temperature spectrum and at atmospheric conditions. In important embodiments, the reaction in the first solvent is conducted under a controlled reaction temperature between 65° to 75° C., preferable at about 70° C., and the reaction in the second solvent is conducted at room temperature.

More broadly, the method involves synthesizing S-MNTX plus counterion by combining a cyclopropylmethyl derivative with oxymorphone in a first solvent to produce the S-MNTX plus counterion. The cyclopropylmethyl derivative contains a leaving group. Preferably the leaving group is a halide or sulfonate . Preferably the leaving group is iodide. The first solvent may be a dipolar aprotic solvent. Examples of such solvents are N-methylpyrrolidone, dimethyl formamide, methylphosphoramide, acetone, 1,4-dioxane, and acetonitrile and combinations thereof. Preferred is N-methylpyrrolidone. The first solvent can be a dipolar protic solvent. Examples are 2-propanol, 1-propanol, ethanol, methanol. The method can further involve exchanging the counterion of S-MNTX with another counterion. Examples of counterions are bromide, chloride, fluoride, nitrate, sulfonate, or carboxylate. The sulfonate can be mesylate, besylate, tosylate or triflate. The carboxylate can be formate, acetate, citrate and fumarate. The method can involve transferring the S-MNTX counterion to a second solvent prior to exchanging the counterion of S-MNTX with another counterion. The method can further involve purifying the S-MNTX plus counterion, for example by recrystallization, by chromatography or by both.

According to another aspect of the invention, method is provided for inhibiting diarrhea in a subject, by administering to a subject in need of such treatment a pharmaceutical composition containing S-MNTX in an amount effective to treat or prevent the diarrhea. The pharmaceutical preparation can be of the type described above. The diarrhea can be acute or chronic. The diarrhea can be caused by any variety of circumstances, alone or combined, such as caused by an infectious agent, food intolerance, food allergy, malabsorption syndrome, reaction to a medication or nonspecific etiology. In some embodiments, the diarrhea is associated with irritable bowel disease or with inflammatory bowel disease. In one embodiment the inflammatory bowel disease is celiac disease. In another embodiment the inflammatory bowel disease is Crohn's disease. In yet another embodiment, the inflammatory bowel disease is ulcerative colitis. In other embodiments the diarrhea results from stomach or bowel resection, removal of a gall bladder, or organic lesions. In other embodiments, the diarrhea is associated with a carcinoid tumor or vasoactive intestinal polypeptide-secreting tumor. In still other embodiments, the diarrhea is chronic functional (idiopathic) diarrhea.

According to the invention, the S-MNTX may be administered in conjunction with an anti-diarrhea agent that is not S-MNTX. By in conjunction with, it is meant at the same time or close enough in time whereby both agents are treating the condition at the same time. In one embodiment, the agent is an opioid or an opioid agonist. In another embodiment, the agent is not an opioid or an opioid agonist.

According to another aspect of the invention, a method is provided for reducing a volume of discharge from a ileostomy or cholostomy in a subject. The method involves administering to a subject in need of such reduction a pharmaceutical composition containing S-MNTX in an amount effective to reduce the volume of discharge from the ileostomy or cholostomy. The pharmaceutical preparation can be of the type described above.

According to another aspect of the invention, a method is provided for reducing a rate of discharge from a ileostomy or cholostomy in a subject. The method involves administering to a subject in need of such reduction a pharmaceutical composition containing S-MNTX in an amount effective to reduce the rate of discharge from the ileostomy or cholostomy. The pharmaceutical preparation can be of the type described above.

According to another aspect of the invention, a method is provided for inhibiting gastrointestinal motility in a subject. The method involves administering to a subject in need of such inhibition a pharmaceutical composition containing S-MNTX in an amount effective to inhibit gastrointestinal motility in the subject. The pharmaceutical preparation can be of the type described above. According to the invention, the S-MNTX may be administered in conjunction with another motility inhibiting agent that is not S-MNTX. In one embodiment, the agent is an opioid or an opioid agonist. Opioids and opioid agonists are described above. In another embodiment, the agent is not an opioid or an opioid agonist. Examples of such gastrointestinal motility inhibiting agents are described below, each as if recited specifically in this summary of invention.

According to another aspect of the invention, a method is provided for treating irritable bowel syndrome. The method involves administering to a patient in need of such treatment a pharmaceutical composition containing S-MNTX in an amount effective to ameliorate at least one symptom of the irritable bowel syndrome. The pharmaceutical preparation can be of the type described above. In one embodiment, the symptom is diarrhea. In another embodiment, the symptom is alternating constipation and diarrhea. In another embodiment, the symptom is abdominal pain, abdominal bloating, abnormal stool frequency, abnormal stool consistency, or combinations thereof.

According to another aspect of the invention, a method is provided for inhibiting pain in a subject. The method involves administering to a patient in need of such treatment a pharmaceutical composition containing S-MNTX in an amount effective to inhibit the pain. The pharmaceutical preparation can be of the type described above. The method can further involve administering to the subject a therapeutic agent other than S-MNTX. In one embodiment the agent other than S-MNTX is an opioid. In another embodiment, the agent other than S-MNTX is a nonopioid pain relieving agent. Nonopioid pain relieving agents include corticosteroids and nonsteroidal anti-inflammatory drugs. Pain relieving agents are described in greater detail below, as if recited herein this summary. In another embodiment, the agent other than S-MNTX is an antiviral agent, antibiotic agent, antifungal agent, antibacterial agent, antiseptic agent, anti-protozoal agent, anti-parasitic agent, anti-inflammatory agent, a vasoconstrictor agent, a local anesthetic agent, an anti-diarrheal agent, or an anti-hyperalgesia agent. If the pain is peripheral hyperalgesia, it can result, for example, from a bite, sting, burn, viral or bacterial infection, oral surgery, tooth extraction, injury to the skin and flesh, wound, abrasion, contusion, surgical incision, sunburn, rash, skin ulcers, mucositis, gingivitis, bronchitis, laryngitis, sore throat, shingles, fungal irritation, fever blisters, boils, plantar's warts, vaginal lesions, anal lesions, corneal abrasion, post-radial keratectomy, or inflammation. It also can be associated with post-surgery recovery. The surgery can be, for example, radial keratectomy, tooth extraction, lumpectomy, episiotomy, laparoscopy, and arthroscopy.

In some embodiments, the pharmaceutical composition is administered locally to a site of the pain. In some embodiments, the administration is intra-articular. In some embodiments, the administration is systemic. In some embodiments, the administration is topical. In some embodiments, the composition is administered to the eye.

According to another aspect of the invention, a method is provided for inhibiting inflammation in a subject. The method involves administering to a patient in need of such treatment a pharmaceutical composition containing S-MNTX in an amount effective to inhibit the inflammation. The pharmaceutical preparation can be of the type described above. The method can also involve administering to the subject a therapeutic agent other than S-MNTX. The therapeutic agent other than S-MNTX can be an anti-inflammatory agent. The administration can be, for example, local administration at a site of the inflammation, systemic administration, or topical administration.

The inflammation in some embodiments is periodontal inflammation, orthodontic inflammation, inflammatory conjunctivitis, hemorrhoids and venereal inflammations. In other embodiments, the inflammation is a skin inflammatory condition. Examples include inflammation associated with a disorder selected from the group consisting of irritant contact dermatitis, psoriasis, eczema, pruritus, seborrheic dermatitis, nummular dermatitis, lichen planus, acne vulgaris, comedones, polymorphs, nodulokystic acne, conglobata, senile acne, secondary acne, medical acne, a keratinization disorder, and blistery derma, atopic dermatitis, and UV-induced inflammation. The skin inflammatory condition also can be associated with skin sensitizatiorior irritation arising from the use of a cosmetic or skin care product which causes skin sensitization or irritation or can be a non-allergic inflammatory skin condition. It also can be induced by all-trans-retinoic acid. In other embodiments, the inflammation can be a systemic inflammatory condition. Examples include conditions selected from the group consisting of inflammatory bowel disease, rheumatoid arthritis, cachexia, asthma, Crohn's disease, endotoxin shock, adult respiratory distress syndrome, ischemic/reperfusion damage, graft-versus-host reactions, bone resorption, transplantation and lupus. Other embodiments can involve inflammation associated with a. condition selected from the group consisting of multiple sclerosis, diabetes, and wasting associated with acquired immunodeficiency syndrome (AIDS) or cancer.

According to another aspect of the invention, a method is provided for inhibiting the production of tumor necrosis factor in a subject. The method involves administering to a patient in need of such treatment a pharmaceutical composition containing S-MNTX in an amount effective to inhibit the production of tumor necrosis factor. The pharmaceutical preparation can be of the type described above. The method can also involve administering to the subject a therapeutic agent other than S-MNTX.

According to another aspect of the invention, a method is provided for regulating gastrointestinal function in a subject. The method involves administering to a patient in need of such treatment a pharmaceutical composition containing S-MNTX and administering to the subject a peripheral mu opioid antagonist, both in amounts to regulate gastrointestinal function. In one embodiment, the peripheral mu opioid antagonist is R-MNTX.

According to another aspect of the invention, a method is provided. The method involves preventing or treating a psychogenic eating or digestive disorder by administering to a patient a composition described above in an amount effective to prevent or treat the psychogenic eating or digestive disorder.

According to another aspect of the invention, a kit is provided. The kit includes a package containing a sealed container of a pharmaceutical composition containing S-MNTX. The kit further can include a therapeutic agent other than S-MNTX. The therapeutic agent other than S-MNTX in one embodiment is an opioid or opioid agonist. In one aspect, the opioid or opioid agonist has substantially no CNS activity when administered systemically (i.e., is "peripherally acting"). In other embodiments, the therapeutic agent other than S-MNTX is an opioid antagonist. Opioid antagonists include peripheral mu opioid antagonists. In one embodiment, the peripheral opioid antagonist is R-MNTX. In other embodiments, the agent other than S-MNTX is an antiviral agent, antibiotic agent, antifungal agent, antibacterial agent, antiseptic agent, anti-protozoal agent, anti-parasitic agent, anti-inflammatory agent, a vasoconstrictor agent, a local anesthetic agent, an anti-diarrheal agent, or an anti-hyperalgesia agent, or combinations thereof.

According to another aspect of the invention, a method for analyzing S-MNTX in a mixture of R-MNTX and S-MNTX is provided. The method involves conducting high performance liquid chromatography (HPLC) and applying S-MNTX to the chromatography column as a standard. The method preferably involves applying both S-MNTX and R-MNTX as standards to determine relative retention/elution times. Relative Retention times of R and S-MNTX are disclosed therein. In one aspect of this invention, the chromatography is conducted using two solvents, solvent A and solvent B, wherein solvent A is an aqueous solvent and solvent B is a methanolic solvent and wherein both A and B contain trifluroacetic acid (TFA). Preferably, A is 0.1% aqueous TFA and B is 0.1% methanolic TFA. In important embodiments the column comprises a bonded, end-capped silica. In important embodiments, the pore size of the column gel is 5 microns. In a most preferred embodiment, the column, flow rate and gradient program are as follows:

Column: Luna C18(2), 150×4.6 mm, 5μ
Flow Rate: 1 mL/min
Gradient Program:

| Time (min) | % A | % B |
|---|---|---|
| 0:00 | 95 | 5 |
| 8:00 | 65 | 35 |
| 12:00 | 35 | 65 |
| 15:00 | 0 | 100 |
| 16:00 | 95 | 5 |
| 18:00 | 95 | 5 |

Detection can be carried out conveniently by ultraviolet (UV) @230 nm wavelength.

The foregoing HPLC also can be used to determine the relative amount of S-MNTX and R-MNTX by determining the area under the respective R and S curves in the chromatogram produced.

According to another aspect of the invention, methods are provided for ensuring the manufacture of S-MNTX (which is an opioid agonist) that is free of R-MNTX (which is an opioid antagonist). The methods permit for the first time the assurance that a pharmaceutical preparation of S-MNTX which is intended for agonist activity is not contaminated with a compound that opposes the activity of S-MNTX. In this aspect of the invention, a method is provided for manufacturing S-MNTX. The method involves: (a) obtaining a first composition containing S-MNTX, (b) purifying the first composition by chromatography, recyrallization or a combination thereof, (c) conducting HPLC on a sample of purified first composition using R-MNTX as a standard, and (d) determining the presence or absence of R-MNTX in the sample. In important embodiments, both R-MNTX and S-MNTX are used as standards to determine, for example, relative retention time of R-MNTX and S-MNTX. In one embodiment, the purifying is multiple recryallization steps or multiple chromatography steps. In another embodiment, the purifying is carried out until R-MNTX is absent from the sample as determined by HPLC. It should be understood, however, that the "purified first composition" in some aspects of the invention is not necessarily free of detectable R-MNTX. The presence of such R-MNTX, for example, might indicate that further purification steps should be conducted if pure S-MNTX is desired. The methods can further involve packaging purified first composition that is free of HPLC detectable R-MNTX. The methods further can include providing indicia on or within the packaged, purified first composition indicating that the packaged, purified first composition is free of HPLC detectable R-MNTX. The method further can involve packaging a pharmaceutically effective amount for treating anyone of the conditions described herein. The first composition containing S-MNTX can be obtained by the methods described herein. Pure R-MNTX can be obtained as described herein.

According to another aspect of the invention, a packaged product is provided. The package contains a composition comprising S-MNTX, wherein the composition is free of HPLC detectable R-MNTX, and indicia on or contained within the package indicating that the composition is free of detectable R-MNTX. The composition can take on a variety of forms, including, but not limited to, a standard for use in laboratory experiments, a standard for use in manufacturing protocols, or a pharmaceutical composition. If the composition is a pharmaceutical composition, then one important form of indicia is writing on a label or package insert describing the characteristics of the pharmaceutical preparation. The indicia can indicate directly that the composition is free of R-MNTX, or it can indicate the same indirectly, by stating for example that the composition is pure or 100% S-MNTX. The pharmaceutical composition can be for treating any of the conditions described herein. The pharmaceutical composition can contain an effective amount of the pure S-MNTX and can take any of the forms described below as if specifically recited in this summary, including, but not limited to, solutions, solids, semi-solids, enteric coated materials and the like.

These and other aspects of the invention are described in greater detail below.

DETAILED DESCRIPTION

Figure 1:
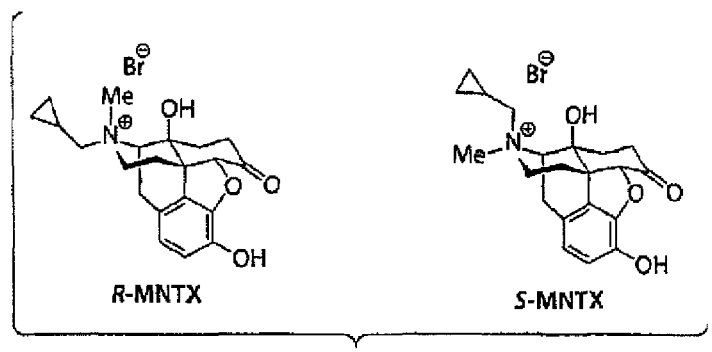
FIG. 1 provides the chemical structure of bromide salts of R-MNTX and S-MNTX.

The invention provides for the compound, S-MNTX, synthetic routes for stereoselective synthesis of S-MNTX, substantially pure S-MNTX, crystals of substantially pure S-MNTX, methods of analysis of S-MNTX, pharmaceutical preparations containing substantially pure S-MNTX, and methods for their use.

S-MNTX, also called (S)-N-(cyclopropylmethyl)-noroxymorphone methyl salt has the structure in Formula I:

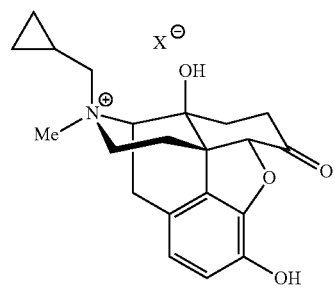

wherein X is a counterion. The counterion can be any counterion, including a zwitterion. Preferably the counterion is pharmaceutically acceptable. Counterions include halides, sulfates, phosphates, nitrates, and anionic-charged organic species. The halide can be iodide, bromide, chloride, fluoride, or combinations thereof. In one embodiment the halide is iodide. In a preferred embodiment the halide is bromide. The anionic-charged organic species may be a sulfonate or carboxylate.

It is believed that the methods of manufacture and the agonist properties of S-MNTX apply equally to S-quarternary derivatives of noroxymorphone other than where the derivative is cyclopropylmethyl. Thus, the invention is intended to embrace S-quarternary derivatives of noroxymorphone where the cyclopropylmethyl is replaced with a moiety R, where R is a 1-20 carbon hydrocarbyl consisting exclusively of carbon and hydrogen, including alkyl, alkenyl, alkynyl, and aryl, substituted or unsubstituted with hydrocarbons or with one or more atoms such as nitrogen, oxygen, silicon, phosphorus, boron, sulfur, or halogen (described in PCT publication WO 2004/043964.) In important embodiments, R is allyl, chloroallyl, or propargyl. In important embodiments, the hydrocarbyl contains 4-10 carbons.

"Alkyl", in general, refers to an aliphatic hydrocarbon group which may be straight, branched or cyclic having from 1 to about 10 carbon atoms in the chain, and all combinations and subcombinations of ranges therein. "Branched" refers to an alkyl group in which a lower alkyl group, such as methyl, ethyl or propyl, is attached to a linear alkyl chain. In certain preferred embodiments, the alkyl group is a $C_1$-$C_5$ alkyl group, i.e., a branched or linear alkyl group having from 1 to about 5 carbons. In other preferred embodiments, the alkyl group is a $C_1$-$C_3$ alkyl group, i.e., a branched or linear alkyl group having from 1 to about 3 carbons. Exemplary alkyl groups include methyl, ethyl, n-propyl, isopropyl, butyl, isobutyl, sec-butyl, tert-butyl, pentyl, hexyl, heptyl, octyl, nonyl and decyl. "Lower alkyl" refers to an alkyl group having 1 to about 6 carbon atoms. Preferred alkyl groups include the lower alkyl groups of 1 to about 3 carbons.

An "alkylating agent" is a compound that can be reacted with a starting material to bind, typically covalently, an alkyl group to the starting material. The alkylating agent typically includes a leaving group that is separated from the alkyl group at the time of attachment to the starting material. Leaving groups may be, for example, halogens, halogenated sulfonates or halogenated acetates. An example of an alkylating agent is cyclopropylmethyl iodide.

"Organic solvent" has its common ordinary meaning to those of skill in this art. Exemplary organic solvents useful in the invention include, but are not limited to tetrahydrofuran, acetone, hexane, ether, chloroform, acetic acid, acetonitrile, chloroform, cyclohexane, methanol, and toluene. Anhydrous organic solvents are included.

"Dipolar aprotic" solvents are protophilic solvents that cannot donate labile hydrogen atoms and that exhibit a permanent dipole moment. Examples include acetone, ethyl acetate, dimethyl sulfoxide (DMSO), dimethyl formamide (DMF) and N-methylpyrrolidone.

"Dipolar protic" solvents are those that can donate labile hydrogen atoms and that exhibit a permanent dipole moment. Examples include water, alcohols such as 2-propanol, ethanol, methanol, carboxylic acids such as formic acid, acetic acid, and propionic acid.

S-MNTX exhibits properties different from those of R-MNTX and different properties from a mixture of S- and R-MNTX. Those properties include mobility on chromatography columns, biological and functional activity, and crystal structure. It is believed that the in vivo clearance rate, the side-effect profile, and the like may also differ from R-MNTX or mixtures of R-MNTX and S-MNTX. As discovered and claimed herein, pure S-MNTX behaves as an agonist of peripheral opioid receptors as demonstrated by inhibition of gastrointestinal transit. As a consequence, S-MNTX activity may be interfered with or antagonized by R-MNTX in mixtures containing both R-MNTX and S-MNTX. It therefore is highly desirable to have S-MNTX in isolated and substantially pure form.

In one aspect of the invention, methods for the synthesis of S-MNTX are provided. S-MNTX may be produced at a purity of greater than or equal to 10%, 20%, 30%, 40%, 50%, 60%, 70%, 75%, 80%, 85%, 90%, 95%, 97%, 98%, 98.5%, 99%, and 99.5% area under the curve (AUC) based on chromatographic techniques. In a preferred embodiment, the purity of S-MNTX is 98% or greater. The amount of R-MNTX in the purified S-MNTX may be less than or equal to about 90%, 80%, 70%, 60%, 50%, 40%, 30%, 20%, 10%, 5%, 3%, 2%, 1%, 0.5%, 0.3%, 0.2%, 0.1% (AUC) or undetectable by chromatographic techniques described herein. It will be appreciated by the skilled artisan that the detection of the methods will depend upon the detection and quantitation limits of the employed technique. Quantitation Limit is the lowest amount of R-MNTX that can be consistently measured and reported, regardless of variations in laboratories, analysts, instruments or reagent lots. Detection Limit is the lowest amount of R-MNTX in a sample which can be detected but not necessarily quantitated as an exact value. In one embodiment of the invention the detection limit is 0.1% and the quantitation limit is 0.2%. In yet another embodiment the detection limit is 0.02% and the quantitation limit is 0.05%.

Figure 2:
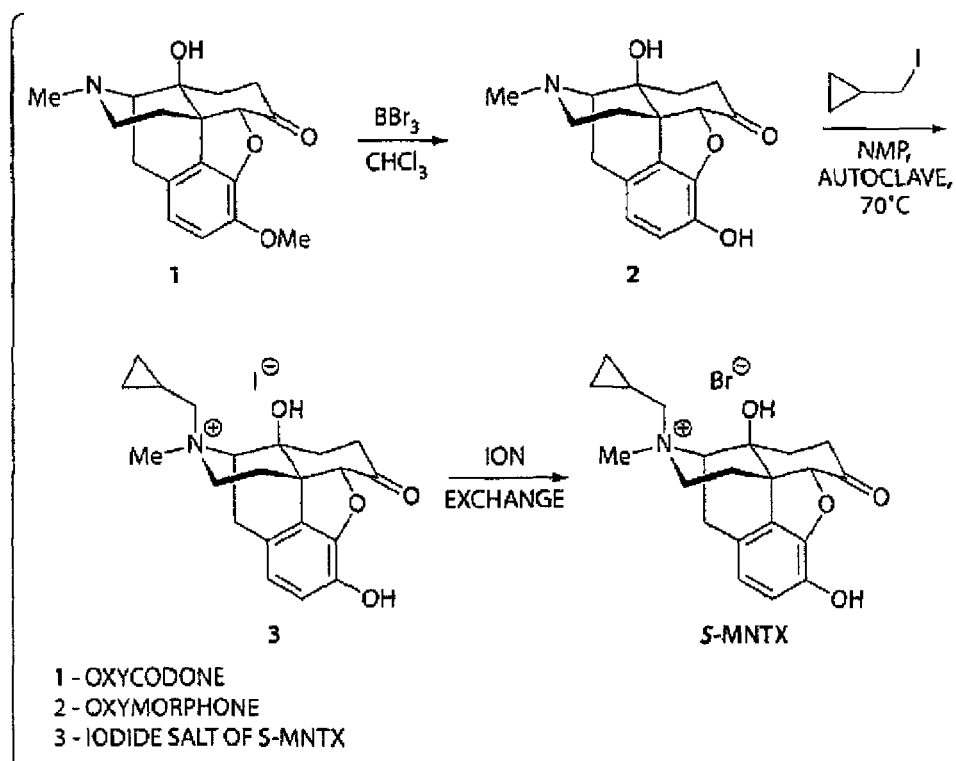
FIG. 2 illustrates a representative reaction scheme of the invention.

Various synthetic protocols were attempted to synthesize S-MNTX. Many of the syntheses failed to make S-MNTX or failed to make S-MNTX at acceptable purity levels or yields. In the successful method of the invention, S-MNTX was synthesized via the direct alkylation of oxymorphone while leaving the phenolic OH group of oxymorphone unprotected (FIG. 2). Oxymorphone was reacted with the methylcyclopropane species iodomethyl cyclopropane. The S-MNTX salt that results includes a counterion such as iodide, that can then be exchanged for a preferred counterion such as bromide. The starting material in the synthesis of S-MNTX, oxymorphone, may be obtained at about 95% yield through the demethylation of oxycodone, for example, with boron tribromide. Alternatively, the oxymorphone may be obtained through commercial sources.

An alkylation reaction may be performed in a solvent, or solvent system, that may be anhydrous. The solvent system may be a single solvent or may include a combination of two or more solvents. Suitable solvent systems may include dipolar aprotic solvents such as N-methylpyrrolidone (NMP), dimethyl formamide (DMF), hexamethylphosphoramide (HMPA), acetone, 1,4-dioxane and acetonitrile, and dipolar protic solvents such as 2-propanol. Solvent systems may also include dipolar aprotic solvents in combination with aliphatic ethers, such as tetrahydrofuran (THF), 1,2-dimethoxyethane (glyme), diethyleneglycol-dimethyl ether (diglyme), 1,4-dioxane, methyl t-butyl ether (methyl 1,1,-dimethylethyl ether, or 2-methyl-2-methoxypropane) diethyl ether, other polar solvents may also be included in some embodiments. For instance, the solvent system may include acetone, methylethylketone, diethylketone (3-pentanone), and t-butylmethylketone(3,3-dimethylbutan-2-one). Alkylation solvent systems may also include aliphatic or alicyclic congeners of any of the compounds disclosed above. Solvent systems may include two or more solvents in any proportion and appropriate proportions for a particular alkylation reaction may be determined through routine experimentation. Notwithstanding the foregoing, surprisingly, NMP proved the preferred solvent.

The solvent may be used at a ratio of less than, greater than, or equal to about 1, 2, 3, 4, 5, 10 or more volumes. In some cases it may be preferred to minimize the amount of solvent used, such as when product is to be transferred from the solvent using a liquid/liquid extraction or when product is to be crystallized or when the solvent is to be removed from the product.

The alkylating agent may be added to the starting material in various molar ratios, such as less than 8, 12, 16, 20, 24 or greater than 24 equivalents per equivalent of starting material. In some instances, it has been found that reaction efficiency (production of S-MNTX) may be substantially independent of the amount of alkylating agent used.

In one set of embodiments, alkylation may be performed using the Finkelstein reaction. An alkyl halide, such as cyclopropylmethyl chloride, can be combined with a halide salt, such as sodium iodide, to continuously supply a reactive halogenated alkylating agent, such as cyclopropylmethyl iodide, that is replenished as it is consumed.

Starting materials may be alkylated at atmospheric pressure in an open vessel or under pressure. The reaction is conducted such that the temperature is maintained or controlled over the reaction time at a prescribed temperature using methods/equipment as are known in the art. One device for maintaining a controlled temperature throughout the alkylation reaction is a heater/chiller unit. Controlling the temperature throughout the alkylation reaction inhibits or reduces temperature fluctuations. In one embodiment, the temperature does not exceed 110° C., preferably does not exceed 100° C. For example, oxymorphone may be alkylated in an open or closed vessel over a range of from 50 to 100° C., 60 to 90° C., or 65 to 75° C. The reaction is allowed to proceed up to about 22 hours, preferably for about 15 to 22 hours, more preferably about 16 to 20 hours. It is contemplated that reaction times may be shortened through the use of microwave irradiation. In one embodiment, reactants are placed in a closed vessel at 70° C. for about 17 hours to produce a product having a ratio of oxymorphone to S-MNTX of about 1:1. In a preferred embodiment, the alkylation is conducted at 70° C. for about 20 hours in an open vessel (atmospheric pressure) wrapped to reduce exposure to light.

In some embodiments, S-MNTX may be isolated from the solvent in which it is produced. For example, the solvent may be removed from a residue containing the S-MNTX, or any. S-MNTX may be transferred from the alkylation solvent to a transfer solvent. Transfer solvents may be polar or non-polar and may have boiling points below 100° C. Transfer solvents may include esters, aldehydes, ethers, alcohols, aliphatic hydrocarbons, aromatic hydrocarbons and halogenated hydrocarbons. Specific transfer to solvents include, for example, dioxane, ethyl acetate, isopropyl acetate, methanol, ethanol, dichloromethane, acetonitrile, water, aqueous HBr, heptane, and MTBE. In one embodiment, a mixture of isopropyl acetate and dioxane can be used to at least partially isolate S-MNTX from NMP. Upon mixing one or more of these solvents with a solution of S-MNTX in NMP, a light colored solid may develop that becomes an oil over time.

Any residue obtained from the solvent may be worked up to purify and isolate the product, S-MNTX. Purification and isolation may be done using methods known to those skilled in the art, such as by using separation techniques like chromatography, recrystallization, or combinations of various separation techniques as are known the art. In one embodiment, flash chromatography using a C18 column may be used with an aqueous methanol solvent modified with 0.2% HBr. Methanol content may vary from, for example, about 2.5% to about 50%. In a preferred embodiment, the S-MNTX is purified using recrystallization. The process may be repeated until desired purity of product is obtained. In one embodiment, S-MNTX is recrystallized at least two times, three times, or four or more times to achieve the desired level of purity. For example, S-MNTX may be obtained at purities of greater than or equal to 50%, 80%, 85%, 90%, 95%, 97%, 98%, 98.5%, 99.8% (AUC) based on chromatographic techniques. Any impurities may include the starting material, oxymorphone of less than 0.2%, with no detectable R-MNTX. Recrystallization may be achieved using a single solvent, or a combination of solvents. A preferred recrystallization is achieved by dissolving S-MNTX in a polar solvent, and then adding a less polar cosolvent. In a more preferred embodiment, S-MNTX is purified by recrystallization from methanol and the cosolvent $CH_2Cl_2$/IPA (6:1). The recrystallization is repeated to achieve desired purity.

S-MNTX, and its derivatives, are produced in the salt form. Derivatives such as zwitterions of S-MNTX are included. S-MNTX, as shown in FIG. 1, may include a positively charged quaternary ammonium group and may be paired with a counterion such as a monovalent or multivalent anion. These anions may include, for example, halides, sulfates, phosphates, nitrates and charged organic species such as sulfonates and carboxylates. Preferred anions include halides such as bromide, chloride, iodide, fluoride, and combinations thereof. In some embodiments, bromide is most preferred. Specific anions may be chosen based on factors such as, for example, reactivity, solubility, stability, activity, cost, availability and toxicity.

Counterions of the S-MNTX salt can be exchanged for alternative counterions. When an alternative counterion is desired, an aqueous solution of an S-MNTX salt can be passed over an anion exchange resin column to exchange some or all of the counterion of the S-MNTX salt for a preferred alternative counterion. Examples of anion exchange resins include AG 1-X8 in a 100 to 200 mesh grade, available from Bio-Rad. In another embodiment, the S-MNTX cation can be retained on a cation exchange resin and can then be exchanged by removing the S-MNTX from the resin with a salt solution that includes a preferred anion, such as bromide or chloride, forming the desired S-MNTX salt in solution.

The S-MNTX of the present invention has numerous utilities. One aspect of the invention is S-MNTX as a chromatographic standard in identifying and distinguishing S-MNTX from other components in a sample in a chromatographic separation. Another aspect of the invention is the use of S-MNTX as a chromatographic standard in identifying and distinguishing S-MNTX in a mixture containing S-MNTX and R-MNTX. Isolated S-MNTX is also useful in the development of protocols for purifying and distinguishing S-MNTX from R-MNTX in reaction mixtures. Such protocols are described herein and also in co-pending application entitled "Synthesis of (R)-N-Methylnaltrexone", , Ser. No. 60/684,616, filed on even date herewith.

The S-MNTX may be provided in a kit form with instruction for its use as a standard. The kit may further comprise an authentic R-MNTX as a standard. The S-MNTX for use as a standard preferably has a purity of 99.8% or greater with no detectable R-MNTX.

One aspect of the invention is a method of resolving and identifying S-MNTX and R-MNTX in a solution of MNTX. The S-MNTX also is useful in HPLC assay methods of quantifying an amount of S-MNTX in a composition or mixture in which the method comprises applying a sample of the composition or mixture to a chromatography column, resolving the components of the composition or mixture, and calculating the amount of S-MNTX in the sample by comparing the percentage of a resolved component in the sample with the percentage of a standard concentration of S-MNTX. The method is particularly useful in reverse phase HPLC chromatography. The S-MNTX of the present invention by virtue of its agonist activity on opioid receptors, is useful as a standard of agonist activity in in vitro and in vivo opioid receptor assays such as those described herein.

The S-MNTX can be used to regulate a condition mediated by one or more peripheral opioid receptors, prophylactically or therapeutically, to agonize peripheral opioid receptors, in particular peripheral mu opioid receptors. The subjects being administered S-MNTX may receive treatment acutely, chronically or on an as needed basis.

The subjects to which the S-MNTX is administered are vertebrates, in particular mammals. In one embodiment the mammal is a human, nonhuman primate, dog, cat, sheep, goat, horse, cow, pig and rodent. In a preferred embodiment, the mammal is a human.

Mu and other opioid receptors exist in the gastrointestinal tract. Of the major classes of opioid receptors in the GI tract, mu receptors are principally involved in modulation of GI activity. Kappa opioid receptors may play a role (Manara L et al *Ann. Rev. Phamacol. Toxicol,* 1985, 25:249-73). In general, the S-MNTX is used to prevent or treat conditions associated with the need for activation or modulation of opioid receptors, in particular, peripheral opioid receptors. Of interest is the use of S-MNTX to prevent or treat conditions associated with the need for activation or modulation of opioid receptors in the GI tract, in particular mu opioid receptors. Such conditions which may be prevented or treated include diarrhea and used to prevent or inhibit certain forms of gastrointestinal dysfunction including certain forms of inflammatory bowel syndrome, and eating and digestive disorders.

In one aspect, S-MNTX can be used to treat diarrhea. Gastrointestinal function is regulated, at least in part, by one or more opioid receptors as well as endogenous opioids. Opioid antagonists are known to increase gastrointestinal motility and may thus be used effectively as a treatment for constipation. Opioid agonists on the other hand, in particular peripheral opioid agonists such as loperamide are known to decrease gastrointestinal motility and can be useful in treating diarrhea in mammals. S-MNTX as discovered by Applicants as an opioid agonist, can be administered to a patient in need of treatment for diarrhea. Diarrhea as used herein is defined as one or more of the following: 1) stool loose in consistency; 2) passing of greater than 3 stools per day; and/or 3) passing a stool volume of ≥200 g (150 ml) per day. S-MNTX is administered in an amount effective to prolong the transit time of intestinal contents resulting in reduced fecal volume, increase fecal viscosity and bulk density and diminished loss of fluid and electrolytes.

The S-MNTX of the present invention by virtue of its opioid agonist activity is useful in the prevention and treatment of diarrhea having diverse etiology including acute and chronic forms of diarrhea, including chronic functional (idiopathic) diarrhea.

Acute diarrhea or short-term diarrhea as used herein is diarrhea lasting less than 1 week in duration, typically 1 to 3 days. Chronic diarrhea, ongoing or prolonged diarrhea as used herein is diarrhea lasting 1 week or longer duration. Chronic diarrhea may last for months or even years and may be continuous or intermittent. Various forms and causes of diarrhea which may benefit from treatment using S-MNTX include, but are not limited to those described below.

Viral gastroenteritis or "stomach flu" caused by any virus including but not limited to rotavirus, Norwalk virus, cytomegalovirus, herpes simples virus, Hepatitis virus, and Adenovirus, is amenable to treatment using S-MNTX.

Food poisoning and traveler's diarrhea which occur from eating food or drinking water contaminated with organisms such as bacteria and parasites are amenable to treatment using S-MNTX. Bacteria commonly causing diarrhea include *Escherichia coli, Salmonella, Shigella, Clostridia, Campylobacter, Yersinia,* and *Listeria.* Parasites which cause diarrhea include *Giardia lamblia, Entamaeba histolytica,* and *Cryptosporidium.* Fungus which may cause diarrhea includes *Candida.*

Certain medical conditions can also lead to diarrhea including malabsorption syndromes such as lactose intolerance, celiac disease (sprue or gluten malabsorption), cystic fibrosis, intolerance to the protein in cows milk or other specific foods like beans, or fruits. Allergies to specific foods is another condition which may cause gastrointestinal irritation and/or allergic reaction leading to diarrhea. Typical food allergens include peanuts, corn and shellfish. Diarrhea caused by or associated with these medical conditions is amendable to treatment using S-MNTX of the present invention.

Other medical conditions that lead to diarrhea, in particular chronic diarrhea include inflammatory bowel diseases which include Crohn's disease and ulcerative colitis, irritable bowel syndrome (IBS) and immune deficiency may also benefit from S-MNTX to prevent or treat the diarrhea.

S-MNTX is useful in preventing and treating diarrhea caused by medications and/or therapies such as antibiotics, laxatives containing magnesium, chemotherapeutics for cancer treatment and high dose radiation therapy.

Diarrhea is also associated with Zollinger-Ellison syndrome, nerve disorders such as autonomic neuropathy or diabetic neuropathy, carcinoid syndrome, vasoactive intestinal polypeptide-secreting tumor, and anatomical conditions of the gastrointestinal tract including short bowel syndrome, gastrectomy, bowel resection with or without ileostomy or colostomy, and removal of the gall bladder. Such conditions are amenable to treatment using S-MNTX.

S-MNTX may be administered through any route, oral or parenteral, including intraperitoneal, intravenous, vaginal, rectal, intramuscular, subcutaneously, aerosol, nasal spray, transmucosal, transdermal, topical, colonic, and the like for the prevention and treatment of diarrhea.

S-MNTX is also useful in methods of reducing a volume of discharge from a ileostomy or cholostomy in a subject. The S-MNTX is provided in an amount effective to reduce the volume of discharge from the ostomy, compared to the volume of discharge from the ostomy in the absence of S-MNTX. S-MNTX is also useful in controlling the rate of discharge from an ostomy, in particular in reducing the rate of discharge in a subject in need of lower rate of discharge.

According to another aspect of the invention, a method is provided for inhibiting gastrointestinal motility in a subject. The method involves administering to a subject in need of such inhibition a pharmaceutical composition containing S-MNTX in an amount effective to inhibit gastrointestinal motility in the subject. According to the invention, the S-MNTX may be administered in conjunction with another motility inhibiting agent that is not S-MNTX. In one embodiment, the agent is an opioid or an opioid agonist. Opioids and opioid agonists are described above. In another embodiment, the agent is not an opioid or an opioid agonist. Examples of such nonopioid gastrointestinal motility inhibiting agents include, for example, cisapride, antacids, aluminum hydroxide, magnesium aluminum silicate, magnesium carbonate, magnesium hydroxide, calcium carbonate, polycarbophil, simethicone, hyoscyamine, atropine, furazolidone, difenoxin, octreotide, lansoprazole, kaolin, pectin, activated charcoal, sulphaguanidine, succinylsulphathiazole, phthalylsulphathiazole, bismuth-containing preparations such as bismuth aluminate, bismuth subcarbonate, bismuth subcitrate, bismuth citrate, tripotassium dicitrato bismuthate, bismuth tartrate, bismuth subsalicylate, bismuth subnitrate and bismuth subgallate, opium tincture (paregoric), herbal medicines and plant-derived anti-diarrheal agents. Further such agents include benzodiazepine compounds, antispasmodic, selective serotonin reuptake inhibitors (SSRIs), cholecystokinin (CCK) receptor antagonists, natural killer (NK) receptor antagonists, Corticotropin Releasing Factor (CRF) receptor agonists, antacids, GI relaxants, anti-gas compounds, pentosan polysulfate, anti-emetic dopamine D2 antagonists, gonadotrophin-releasing hormone analogues (leuprolide), corticotrophin-1 antagonists, neurokinin 2 receptor antagonists, cholecystokinin-1 antagonists, beta-blockers, anti-esophageal reflux agents, anti-inflammatory agents, $5HT_1$ agonists, $5HT_3$ antagonists, $5HT_4$ antagonists, bile salt sequestering agents, bulk-forming agents, $alpha_2$-adrenergic agonists, antidepressants such as tricyclic antidepressants. Additional such agents include antimuscarinic agents, ganglion blocking agents, hormones and hormone analogs, and motilin receptor antagonists. Antimuscarinic agents include belladonna alkaloids, quaternary ammonium antimuscarinic compounds and tertiary amine antimuscarinic compounds. Examples of belladonna alkaloids include belladonna leaf extracts, belladonna tincture, and belladonna extract. Examples of quaternary ammonium antimuscarinic agents include Anisotropine or Anisotropine methylbromide (Valpin), Clidinium or Clidinium bromide (Quarzan), Glycopyrrolate (Robinul), Hexocyclium methylsulfate (Tral), Homatropine, Ipratropium or Ipratropium bromide, Isopropamide or Isopropamide iodide (Darbid), Mepenzolate or Mepenzolate bromide (Cantil), Methantheline or Methantheline bromide (Banthine), Methscopolamine or Methscopolamine bromide (Pamine), Oxyphenonium, and Propantheline or Propantheline bromide. Examples of tertiary amine antimuscarinic agents include Atropine, Dicyclomine or Dicyclomine hydrochloride (Bentyl and others), Flavoxate hydrochloride (Urispas), Oxybutynin or Oxybutynin chloride (Ditropan), Oxyphencyclimine or Oxyphencyclimine hydrochloride (Daricon), Propiverine, Scopolamine, Tolterodine, and Tridihexethyl or Tridihexethyl chloride (Pathilon). Other antimuscarinic agents include Pirenzepine, Telenzepine, AF-DX116, Methoctranine, Himbacine, and Hexahydrosiladifenidol. Ganglion blocking agents include synthetic amines such as Hexamethonium, Mecamylamine, Tetraethylammonium, and Acetylcholine. Examples of hormones or hormone analogs that are anti-gastrointestinal motility agents include: somatostatin and somatostatin receptor agonists. Examples of somatostatin analogs include octreotide (e.g., Sandostatin®) and vapreotide. Motilin to antagonists include (Phe3, Leu-13) porcine motilin, $214^{th}$ American Chemical Society (ACS) Meeting (Part V); Highlights from Medicinal Chemistry Poster Session, Wednesday 10 September, Las Vegas, Nev., (1997), Iddb Meeting Report Sep. 7-11 (1997); and ANQ-1 1 125, Peeters T. L., et al., Biochem. Biophys. Res. Commun., Vol. 198(2), pp. 411-416 (1994).

In another aspect, S-MNTX may be used to treat eating and digestive disorders. Eating disorders and digestive disorders amenable to treatment using S-MNTX according to the invention comprise, but are not limited to, the regulation of pathological imbalanced appetite, loss of appetite or diminished appetite, induced for example by pregnancy, cancer, infectious diseases such as influenza, HCV or HIV, as a result of catabolism, cachexy, anorexia, especially anorexia nervosa, dysorexia, dysponderosis, adiposity, bulimia, obesity, gastroparesis, especially neurogenic gastroparesis, diabetic gastroparesis, myogenic gastroparesis or gastroparesis induced by drugs, gastroatonia, gastroparalysis or enteroparesis, and stenosis of the gastrointestinal tract, especially stenosis of the pylorus.

Pain has been defined in a variety of ways. For example, pain can be defined as the perception by a subject of noxious stimuli that produces a withdrawal reaction by the subject Analgesia, is the reduction of pain perception. Agents that selectively block an animal's response to a strong stimulus without obtunding general behavior or motor function are referred to as analgesics. Opiates and opioid agonists affect pain via interaction with specific opioid receptors. Given the discovery that S-MNTX has opiate agonist activity on gastrointestinal transit in rats, there is a rationale for using S-MNTX in treatment of pain.

In general, administration of S-MNTX and derivatives thereof according to the invention can be used to facilitate management of pain that is associated with any of a wide variety of disorders, conditions, or diseases. "Pain" as used herein, unless specifically noted otherwise, is meant to encompass pain of any duration and frequency, including, but not limited to, acute pain, chronic pain, intermittent pain, and the like. Causes of pain may be identifiable or unidentifiable. Where identifiable, the origin of pain may be, for example, of malignant, non-malignant, infectious, non-infectious, or autoimmune origin. One embodiment is the management of pain associated with diseases, disorders, or conditions that require short-term therapy, e.g., dental procedures, bone fractures, outpatient surgeries, for which therapy involves treatment over a period of hours up to 3 days. Of particular interest is the management of pain associated with disorders, diseases, or conditions that require long-term therapy, e.g., chronic and/or persistent diseases or conditions for which therapy involves treatment over a period of several days (e.g., about 3 days to 10 days), to several weeks (e.g., about 2 weeks or 4 weeks to 6 weeks), to several months or years, up to and including the remaining lifetime of the subject; Subjects who are not presently suffering from a disease or condition, but who are susceptible to such may also benefit from prophylactic pain management using the compositions and methods of the invention, e.g., prior to traumatic surgery. Pain amenable to therapy according to the invention may involve prolonged episodes of pain alternating with pain-free intervals, or substantially unremitting pain that varies in severity.

In general, pain can be nociceptive, somatogenic, neurogenic, or psychogenic. Somatogenic pain can be muscular or skeletal (i.e., osteoarthritis, lumbosacral back pain, posttraumatic, myofascial), visceral (i.e., pancreatitis, ulcer, irritable bowel), ischemic (i.e., arteriosclerosis obliterans), or related to the progression of cancer (e.g., malignant or non-malignant). Neurogenic pain can be due to posttraumatic and postoperative neuralgia, can be related to neuropathies (i.e., diabetes, toxicity, etc.), and can be related to nerve entrapment, facial neuralgia, perineal neuralgia, postamputation, thalamic, causalgia, and reflex sympathetic dystrophy.

Specific examples of conditions, diseases, disorders, and origins of pain amenable to management according to the present invention include, but are not necessarily limited to, cancer pain (e.g., metastasis or non-metastatic cancer), inflammatory disease pain, neuropathic pain, postoperative pain, iatrogenic pain (e.g., pain following invasive procedures or high dose radiation therapy, e.g., involving scar tissue formation resulting in a debilitating compromise of freedom of motion and substantial pain), complex regional pain syndromes, failed-back pain (e.g., acute or chronic back pain), soft tissue pain, joints and bone pain, central pain, injury (e.g., debilitating injuries, e.g., paraplegia, quadriplegia, etc., as well as non-debilitating injury (e.g., to back, neck, spine, joints, legs, arms, hands, feet, etc.)), arthritic pain (e.g., rheumatoid arthritis, osteoarthritis, arthritic symptoms of unknown etiology, etc.), hereditary disease (e.g., sickle cell anemia), infectious disease and resulting syndromes (e.g., Lyme disease, AIDS, etc.), headaches (e.g., migraines), causalgia, hyperesthesia, sympathetic dystrophy, phantom limb syndrome, denervation, and the like. Pain can be associated with any portion(s) of the body, e.g., the musculoskeletal system, visceral organs, skin, nervous system, etc.

The methods of the invention can be used to manage pain in patients who are opioid naïve or who are no longer opioid naïve. Exemplary opioid nave patients are those who have not received long-term opioid therapy for pain management. Exemplary non-opioid naïve patients are those who have received short-term or long-term opioid therapy and have developed tolerance, dependence, or other undesirable side effect. For example, patients who have intractable adverse side effects with oral, intravenous, or intrathecal morphine, transdermal fentanyl patches, or conventionally administered subcutaneous infusions of fentanyl, morphine or other opioid can achieve good analgesia and maintain favorable side-effects profiles with deliver of S-MNTX and derivatives thereof.

The term "pain management or treatment" is used here to generally describe regression, suppression, or mitigation of pain so as to make the subject more comfortable as determined by subjective criteria, objective criteria, or both. In general, pain is assessed subjectively by patient report, with the health professional taking into consideration the patient's age, cultural background, environment, and other psychological background factors known to alter a person's subjective reaction to pain.

As mentioned above, S-MNTX can be administered together with a therapeutic agent that is not S-MNTX, including but not limited, therapeutic agents that are pain relieving agents. In one embodiment, the pain relieving agent is an opioid or opioid agonist. In another embodiment, the pain relieving agent is a nonopioid pain relieving agent such as a corticosteroid or a nonsteroidal anti-inflammatory drug (NSAID). Pain relieving agents include: Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Ibuprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lornoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentainl Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propiram Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium; Zucapsaicin, and combinations thereof.

Hyperalgesia is an increased senisitivy to pain or enhanced intensity of pain sensation. Hyperalgesia can result when a subject is hypersensitive to a stimulus, resulting in an exaggerated pain response to a given stimulus Hyperalgesia is often the result of a local inflammatory state and may follow trauma or injury to body tissue. Inflammation may follow, or be associated with, local infection, blisters, boils, skin injury such as cuts, scrapes, burns, sunburns, abrasions, surgical incisions, inflammatory skin conditions such as poison ivy, allergic rashes, insect bites and stings, and joint inflammation. S-MNTX can be used to prevent and treat peripheral hyperalgesia and to reduce pain and/or symptoms resulting from inflammation. As used herein, hyperalgesia includes pruritis, or itching, and S-MNTX may be used as an antipruritic treatment.

The compositions and methods herein are intended for the preventions and treatment of hyperalgesia association with numerous inflammatory conditions and injuries. The compositions and methods provided herein may be used to treat a variety of hyperalgesic conditions associated with burns, including, but not limited to, thermal, radiation, chemical, sun and wind bums, abrasions, including, for example, corneal abrasions, bruises, contusions, frostbite, rashes, including, for example, allergic heat and contact dermatitis, such as, for example, poison ivy and diaper rashes, acne, insect bites/stings, skin ulcers, including, but not limited to, diabetic and decubitus ulcers, mucositis, inflammation, for example, periodontal inflammation, orthodontic inflammation, inflammation/irritation arising from use of a cosmetic or skin care product, inflammatory conjunctivitis, hemorrhoids and venereal inflammations, gingivitis, bronchitis, laryngitis, sore throat, singles, fungal irritation, for example, athlete's foot and jock itch, fever blisters, boils, plantar's warts or vaginal lesions, including, for example, mycotic and sexually transmitted vaginal lesions.

Hyperalgesic conditions associated with skin surfaces include burns, including but not limited to, thermal, radiation, chemical, sun and wind burns, abrasions such as, for example, corneal abrasions, bruises, contusions, frostbite, rashes including allergic, heat contact dermatitis (for example, poison ivy) and diaper rashes), acne insect bites/stings and skin ulcers (including diabetic and decubitus ulcers). Hyperalgesic conditions of the mouth, larynx and bronchium include mucositis, post-tooth extraction, periodontal inflammation, gingivitis, orthodontic inflammation, bronchitis, laryngitis and sore throat. Hyperalgesic conditions of the eyes include corneal abrasions, post-radial keratectomy and inflammatory conjunctivitis. Hyperalgesic conditions of the rectum/anus include hemorrhoids and venereal inflammations. Hyperalgesic conditions associated with infectious agents include shingles, fungal irritations (including athlete's foot and jock itch), fever blisters, boils, plantar's warts and vaginal lesions (including lesions associated with mycosis and sexually transmitted diseases). Hyperalgesic conditions may also be associated with recovery following surgery, such as recovery following lumpectomy, episiotomy, laparoscopy, arthroscopy, radial keratectomy and tooth extraction.

As a preventative or treatment for peripheral hyperalgesia, S-MNTX can be administered using any pathway that provides for delivery of the compound to an afflicted area. Administration may be oral or parenteral. Methods of administration also include topical and local administration. S-MNTX can be applied to any body surface including skin, joints, eyes, lips and mucosal membranes.

S-MNTX may be delivered in combination with other compounds, such as those disclosed herein, that provide anti-hyperalgesic effects, including, but not limited to, pain medications, itching medications, anti-inflammatory agents, and the like. S-MNTX also may be administered with other compounds used to treat the conditions causing the inflammation, such as antivirals, antibacterials, antifungals, and anti-infectives. These other compounds may act and be administered locally or systemically and may be part of the same composition or may be administered separately. Such compounds are described in greater detail below.

Inflammation is often associated with an increase in Tumor Necrosis Factor (TNF) production and it is believed that a decrease in TNF production will result in a reduction in inflammation. Peripherally acting opioid agonists have been shown to decrease TNF production (U.S. Pat. No. 6,190,691). The peripherally selective k-opioid, asimadoline, has been shown to be a potent anti-arthritic agent in an adjuvant-induced arthritis animal model (Binder, W. and Walker, J. S. *Br. J. Pharma* 124:647-654). Thus the peripheral opioid agonist activity of S-MNTX and derivatives thereof provide for prevention and treatment of inflammatory conditions. While not being bound by theory, the anti-inflammatory effect of S-MNTX and derivatives thereof may be through inhibition of TNF production, directly or indirectly. The S-MNTX or derivatives thereof may be administered systemically or locally. S-MNTX may be administered in combination with another TNF inhibitor such as loperamide and diphenoxylate or with other anti-inflammatory agents described herein.

Another aspect of the present invention is prevention and/or treatment of a systemic inflammatory condition, preferably inflammatory bowel disease, rheumatoid arthritis, cachexia, asthma, Crohn's disease, endotoxin shock, adult respiratory distress syndrome, ischemic/reperfusion damage, graft-versus-host reactions, bone resorption, transplantation or lupus using S-MNTX or derivatives thereof.

In still another group of embodiments, the inflammatory condition amenable to treatment using S-MNTX or derivatives thereof is associated with multiple sclerosis, diabetes or wasting associated with acquired immunodeficiency syndrome (AIDS) or cancer.

In one group of embodiments, a skin inflammatory condition, preferably psoriasis, atopic dermatitis, UV-induced inflammation, contact dermatitis or inflammation induced by other drugs, including, but not limited to RETIN-A (all-trans-retinoic acid) is amenable to treatment using S-MNTX or derivative thereof.

Another aspect of the invention is a method of treating a non-allergic inflammatory skin condition comprising the administration of S-MNTX in an amount effective to treat the inflammatory condition. Non-allergic inflammatory skin conditions are associated with irritant contact dermatitis, psoriasis, eczema, pruritus, seborrheic dermatitis, nummular dermatitis, lichen planus, acne vulgaris, comedones, polymorphs, nodulokystic acne, conglobata, senile acne, secondary acne, medicinal acne, a keratinization disorder, and blistery dermatoses.

Certain patients particularly amenable to treatment are patients having the symptoms of any one of the foregoing conditions. The patients may have failed to obtain relief or ceased to obtain relief or a consistent degree of relief of their symptoms using other therapies. Such patients are said to be refractory to the conventional treatments. The condition may be induced or a consequence of one or more diverse conditions including, but not limited to, a disease condition, a physical condition, a drug-induced condition, a physiological imbalance, stress, anxiety, and the like. The conditions may be an acute condition or chronic condition.

Subjects can be treated with a combination of the S-MNTX and a therapeutic agent other than the S-MNTX. In these circumstances the S-MNTX and the other therapeutic agent(s) are administered close enough in time such that the subject experiences the effects of the various agents as desired, which typically is at the same time. In some embodiments the S-MNTX will be delivered first in time, in some embodiments second in time, and still in some embodiments at the same time. As discussed in greater detail below, the invention contemplates pharmaceutical preparations where the S-MNTX is administered in a formulation including another pharmaceutical agent. These formulations may be such as those described in U.S. patent application Ser. No. 10/821,809, which is hereby incorporated by reference in its entirety herein. Included are solid, semisolid, liquid, controlled release and other such formulations.

One important class of therapeutic agent which can be part of the prevention and treatment protocol together with the S-MNTX are opioids. It has been surprisingly found by Applicants that S-MNTX used in combination with the opioid, morphine results in an enhanced and apparently synergistic inhibition of gastrointestinal transit. Thus, the present invention provides pharmaceutical compositions comprising S-MNTX in combination with one or more opioids. This will permit alteration of doses not previously obtainable. For example, where a lower dose of opioid is desirable in treating certain peripherally mediated conditions this now is possible by combination with S-MNTX treatment.

The opioid can be any pharmaceutically acceptable opioid. Common opioids are those selected from the group consisting of alfentanil, anileridine, asimadoline, bremazocine, buprenorphine, butorphanol, codeine, dezocine, diacetylmorphine (heroin), dihydrocodeine, diphenoxylate, fedotozine, fentanyl, funaltrexamine, hydrocodone, hydromorphone, levallorphan, levomethadyl acetate, levorphanol, loperamide, meperidine (pethidine), methadone, morphine, morphine-6-glucoronide, nalbuphine, nalorphine, opium, oxycodone, oxymorphone, pentazocine, propiram, propoxyphene, remifentanyl, sufentanil, tilidine, trimebutine, and tramadol.

Depending on the desired effect to be achieved the opioid may be administered parenterally or other systemic route to affect both the central nervous system (CNS) and peripheral opioid receptors. The desired effect of the opioid in combination with S-MNTX may be prevention or treatment of diarrhea, prevention or treatment of pain from any cause or etiology including prevention or treatment of peripheral hyperalgesia. When the indication is prevention or treatment of peripheral hyperalgesia, it is desirable to provide an opioid which does not have concomitant CNS effects or alternatively to administer the opioid topically or locally such that the opioid does not substantially cross the blood brain barrier but provide an effect on peripheral opioid receptors.

Opioids particularly useful for prevention or treatment of diarrhea or prevention or treatment of peripheral hyperalgesia in combination with S-MNTX include but are not to limited to:

(i) loperamide [4-(p-chlorophenyl)-4-hydroxy-N-N-dimethyl-α,α-diphenyl-1-piperidinebutyramide hydrochloride]], loperamide analogs and related compounds as defined herein [see, U.S. Pat. Nos. 3,884,916 and 3,714,159; see, also U.S. Pat. Nos. 4,194,045, 4,116,963, 4,072,686, 4,069,223, 4,066,654.], N-oxides of loperamide and analogs, metabolites and prodrugs thereof and related compounds as defined herein [see, also, U.S. Pat. No. 4,824,853], and related compounds, such as (a), (b) and (c) as follows:

(a) 4-(aroylamino)pyridine-butanamide derivatives and N-oxides thereof as defined herein [see, also U.S. Pat. No. 4,990,521];

(b) 5-(1,1-diphenyl-3-(5- or 6-hydroxy-2-azabicyclo-(2.2.2)oct-2-yl)propyl)-2-alkyl-1,3,4-oxadiazoles, 5-(1,1-diphenyl-4-(cyclic amino)but-2-trans-en-1-yl)-2-alkyl-1,3,4-oxadiazoles, 2-[5-(cyclic amino)-ethyl-10,11-dihydro-5H-dibenzo[a,d]-cyclohepten-5-yl]-5-alkyl-1,3,4-oxadiazoles] and related compounds [see, U.S. Pat. Nos. 4,013,668, 3,996,214 and 4,012,393];

(c) 2-substituted-1-azabicyclo[2,2,2]octanes [see, U.S. Pat. No. 4,125,531];

(ii) 3-hydroxy-7-oxomorphinans and 3-hydroxy-7-oxoisomorphinans [see, e.g., U.S. Pat. No. 4,277,605]

(iii) amidinoureas as provided herein [see, also U.S. Pat. Nos. 4,326,075, 4,326,074, 4203,920, 4,060,635, 4,115,564, 4,025,652] and 2-[(aminophenyl and amidophenyl)amino]-1-azacycloalkanes [see, U.S. Pat. No. 4,533,739];

(iv) metkephamid [H-L-Tyr-D-Ala-Bly-L-Phe-N(Me) Met-NH$_2$; see, e.g., U.S. Pat. No. 4,430,327; Burkhart et al. (1982) *Peptides* 3-869-871; Frederickson et al. (1991) *Science* 211:603-605] and other synthetic opioid peptides, such as H-Tyr-D-Nva-Phe-Orn-NH$_2$, H-Tyr-D-Nle-Phe-Orn-NH$_2$, H-Tyr-D-Arg-Phe-A$_2$bu-NH$_2$, H-Tyr-D-Arg-Phe-Lys-NH$_2$, and H-Lys-Tyr-D-Arg-Phe-Lys-NH$_2$ [see, U.S. Pat. No. 5,312,899; see, also Gesellchen et al. (1981) *Pept.: Synth., Struct., Fund., Proc. Am. Pept. Symp.*, 7$^{th}$; Rich et al., (Eds), Pierce Chem. Co., Rochford, Ill., pp. 621-62] that do not cross the blood brain barrier;

(v) propanamines as defined in U.S. Pat. No. 5,236,947 and the like.

S-MNTX may also be used to treat diarrhea in combination with other anti-diarrheal compounds and compositions. For example, S-MNTX may be administered to a subject in combination with a known anti-diarrheal agent. Two or more compounds may be administered in a cocktail or the compounds may be administered separately using the same or different administration routes. Known anti-diarrheal agents include, for example, loperamide, loperamide analogs, N-oxides of loperamide and analogs, metabolites and prodrugs thereof, diphenoxylate, cisapride, antacids, aluminum hydroxide, magnesium aluminum silicate, magnesium carbonate, magnesium hydroxide, calcium carbonate, polycarbophil, simethicone, hyoscyamine, atropine, furazolidone, difenoxin, octreotide, lansoprazole, kaolin, pectin, activated charcoal, sulphaguanidine, succinylsulphathiazole, phthalylsulphathiazole, bismuth aluminate, bismuth subcarbonate, bismuth subcitrate, bismuth citrate, tripotassium dicitrato bismuthate, bismuth tartrate, bismuth subsalicylate, bismuth subnitrate and bismuth subgallate, opium tincture (paregoric), herbal medicines and plant-derived anti-diarrheal agents.

Other therapeutic agents which can be part of treatment protocols together with S-MNTX are irritable bowel syndrome (IBS) agents, antibiotics, antivirals, anti-fungals, anti-infectives, anti-inflammatory agents including anti-histamines, vasoconstrictors, anti-diarrheals, and the like.

IBS therapeutic agents which may be used in combination with S-MNTX include, but are not limited to, benzodiazepine compounds, antispasmodic, selective serotonin reuptake inhibitors (SSRIs), cholecystokinin (CCK) receptor antagonists, motilin receptor agonists or antagonists, natural killer (NK) receptor antagonists, Corticotropin Releasing Factor (CRF) receptor agonists or antagonists, somatostatin receptor agonists, antacids, GI relaxants, anti-gas compounds, bismuth-containing preparations, pentosan polysulfate, anti-emetic dopamine D2 antagonists, prostaglandin E analogs, gonadotrophin-releasing hormone analogues (leuprolide), corticotrophin-1 antagonists, neurokinin 2 receptor antagonists, cholecystokinin-1 antagonists, beta-blockers, anti-esophageal reflux agents, anti-muscarinics, antidiarrheals, anti-inflammatory agents, anti-motility agents, 5HT$_1$ agonists, 5HT$_3$ antagonists, 5HT$_4$ antagonists, 5HT$_4$ agonists, bile salt sequestering agents, bulk-forming agents, alpha$_2$-adrenergic agonists, mineral oils, antidepressants, herbal medicines.

Specific examples of IBS therapeutic agents include, but are not limited to, the following:

Benzodiazepine compounds and analogs which act to suppress seizures through an interaction with gamma-aminobutyric acid (GABA) receptors of the A-type (GABA$_A$), for example, DIASTAT® and VALIUM®; LIBRIUM®; and ZANAX®.

SSRIs, for example, fluvoxamine; fluoxetine; paroxetine; sertraline; citalopram; venlafaxine; cericlamine; duloxetine; milnacipran; nefazodone; and cyanodothiepin (See The Year Drugs News, 1995 Edition, pp. 47-48 by Prous J. R.) and WO 97/29739.

CCK receptor antagonists, for example, devazepide; lorglumide; dexioxiglumide; loxiglumide, D'Amato, M. et al., Br. J. Pharmacol. Vol. 102(2), pp. 391-395 (1991); Cl 988; L364,718; L3637260; L740,093 and LY288,513; CCK receptor antagonists disclosed in U.S. Pat. No. 5,220,017, Bruley-Des-Varannes, S, et al. Gastroenterol. Clin. Biol. Vol. 15. (10)9 pp. 744-757 (1991), and Worker C: EUPHAR'99—Second European Congress of Pharmacology (Part IV) Budapest, Hungary Iddb Meeting Report 1999 Jul. 3-7.

Motilin receptor agonists or antagonists which include e.g. motilin agonist ABT-269, (erythromycin, 8,9-didehydro-N-dimethyl deoxo-4",6,12-trideoxy-6,9-epoxy-N-ethyl), de(Nmethyl-N-ethyl-8,9-anhydroerythromycin A) and de(N-methyl)-N-isoprop-8,9anhydroerythromycin A), Sunazika T.

et al., Chem. Pharm. Bull., Vol. 37(10), pp. 2687-2700 (1989); A-173508 (Abbot Laboratories); motilin antagonists (Phe3, Leu-13) porcine motilin, 214$^{th}$ American Chemical Society (ACS) Meeting (Part V); Highlights from Medicinal Chemistry Poster Session, Wednesday 10 September, Las Vegas, Nev., (1997), Iddb Meeting Report Sep. 7-11 (1997); and ANQ-1 1 125, Peeters T. L., et al., Biochem. Biophys. Res. Commun., Vol. 198(2), pp. 411-416 (1994).

NK receptor antagonists which include e.g. FK 888 (Fujisawa); GR 205171 (Glaxo Wellcome); LY 303870 (Lilly); MK 869 (Merck); GR82334 (Glaxo Wellcome); L758298 (Merck); L 733060 (Merck); L 741671 (Merck); L 742694 (Merck); PD 154075 (Parke-Davis); S1 8523 (Servier); S1 9752 (Servier); OT 7100 (Otsuka); WIN 51708 (Sterling Winthrop); NKP-608A; TKA457; DNK333; CP-96345; CP-99994; CP122721; L-733060; L-741671; L742694; L-758298; L-754030; GR-203040; GR-205171; RP-67580; RPR-100893 (dapitant); RPR-107880; RPR-111905; FK-888; SDZ-NKT-343; MEN-10930; MEN-11149; S-18523; S-19752; PD-154075 (CAM-4261); SR-140333; LY-303870 (lanepitant); EP-00652218; EP00585913; L-737488; CGP-49823; WIN-51708; SR-48968 (saredutant); SR-144190; YM383336; ZD-7944; MEN-10627; GR-159897; RPR-106145; PD-147714 (CAM-2291); ZM253270; FK-224; MDL-1 05212A; MDL-105172A; L-743986; L-743986 analogs; S-16474; SR-1 42801 (osanetant); PD-161182; SB-223412; and SB-222200.

CRF receptor agonists or antagonists, e.g. as disclosed in WO 99/40089, AXC 2219, Antalarmin, NGD 1, CRA 0165, CRA 1000, CRA 1001.

Somatostatin receptor agonists, e.g. octreotide, vapreotide, lanreotide.

Anti-inflammatory compounds, particularly those of the immuno-modulatory type, for example, NSAIDS; Tumor Necrosis Factor (TNF, TNFa) inhibitors; basiliximab (e.g. SIMULECT®); daclizumab (e.g. ZENAPAX®); infliximab (e.g. REMICADE®); etanercept (e.g. ENBREL®)mycophenolate mofetil (e.g. CELLCEPT®); azathioprine (e.g. IMURAN®); tacrolimus (e.g. PROGRAF®); steroids; methotrexate and GI anti-inflammatory agents, for example, sulfasalazine (e.g. AZULFIDINE®); olsalazine (e.g. DIPENTUM®); and mesalamine (e.g. ASACOL®, PENTASA®, ROWASA®).

Antacids, such as aluminum and magnesium antacids; and calcium hydroxides such as MAALOX®.

Anti-gas compounds, for example, simethicone marketed under the trade names MYLANTA® and MYLICON®; and enzyme preps including PHAZYME® and BEANO®.

Bismuth-containing preparations, for example, bismuth subsalicylate also known as PEPTO-BISMOL®.

Pentosan polysulfate, a heparin-like macromolecular carbohydrate derivative which chemically and structurally resembles glycosaminoglycans, marketed under the trade name ELMIRON®.

Anti-emetic dopamine D2 antagonists which include e.g. domperidone.

Prostaglandin E analogs, gonadotrophin-releasing hormone analogues (leuprolide), corticotrophin-1 antagonists, neurokinin 2 receptor antagonists, cholecystokinin-1 antagonists, beta-blockers.

Anti-esophageal reflux agents include but are not limited to PRILOSEC®.

Antispasmodics and anti-muscarinics include, but are not limited to, dicyclomine, oxybutyin (e.g., oxybutynin chloride), tolterodine (e.g., tolterodine tartarate), alverine anisotropine, atropine (e.g., atropine sulfate), belladonna, homatropine, homatropine methobromide, hyoscyamine (e.g., hyoscyamine sulfate), methscopolamine, scopolamine (e.g., scopolamine hydrochloride), clidinium, cimetropium, hexocyclium, pinaverium, otilonium, glycopyrrolate, and mebeverine.

Antidiarrheals include, but are not limited to, ipratropium, isopropamide, mepenzolate, propantheline, oxyphencylcimine, pirenzepine, diphenoxylate (e.g., diphenoxylate hydrochloride), atropine sulfate, alosetron hydrochloride, difenoxin hydrochloride, bismuth subsalicylate, lactobacillus acidophilus, trimebutine, asimadoline, and octreotide acetate.

Anti-inflammatory agents also include, but are not limited to, mesalamine, sulfasalazine, balsalazide disodium, hydrocortisone, and olsalazine sodium.

$5HT_1$ agonists include, but are not limited to, buspirone.

$5HT_3$ antagonists include, but are not limited to, ondansetron, cilansetron, and alosetron.

$5HT_4$ antagonists include, but are not limited to, piposcrod.

$5HT_4$ agonists include, but are not limited to, tegaserod (e.g., tegaserod maleate), and povcalopride.

Antidepressants include, but are not limited to, desiprimine, amitryptiline, imiprimine, fluoxetine, and paroxetine.

Other IBS therapeutic agents include dexloxiglumide, TAK-637, talnetant, SB 223412, AU 244, neurotrophin-3, GT 160-246, immunoglobulin (IgG), ramoplanin, risaxmin, rimethicone, darifenacine, zamifenacin, loxiglumide, misoprostil, leuprolide, domperidone, somatostatin analogues, phenytoin, NBI-34041, saredutant, and dexloxiglumide.

Antibiotics include, but are not limited to, tetracycline antibiotics, such as chlortetracycline, oxytetracycline, tetracycline, demethylchlortetracycline, metacycline, doxycycline, minocycline and rolitetracycline; such as kanamycin, amikacin, gentamicin $C_{1a}$, $C_2$, $C_{2b}$ or $C_1$, sisomicin, netilmicin, spectinomycin, streptomycin, tobramycin, neomycin B, dibekacin and kanendomycin; macrolides, such as maridomycin and erythromycin; lincomycins, such as clindamycine and lincomycin; penicillanic acid (6-APA)- and cephalosporanic acid (7-ACA)-derivatives having (6β- or 7β-acylamino groups, respectively, which are present in fermentatively, semi-synthetically or totally synthetically obtainable 6β-acylaminopenicillanic acid or 7β-acylaminocephalosporanic acid derivatives and/or 7β-acylaminocephalosporanic acid derivatives that are modified in the 3-position, such as penicillanic acid derivatives that have become known under the names penicillin G or V, such as phenethicillin, propicillin, nafcillin, oxycillin, cloxacillin, dicloxacillin, flucloxacillin, cyclacillin, epicillin, mecillinam, methicillin, azlocillin, sulbenicillin, ticarcillin, mezlocillin, piperacillin, carindacillin, azidocillin or ciclacillin, and cephalosporin derivatives that have become known under the names cefaclor, cefuroxime, cefazlur, cephacetrile, cefazolin, cephalexin, cefadroxil, cephaloglycin, cefoxitin, cephaloridine, cefsulodin, cefotiam, ceftazidine, cefonicid, cefotaxime, cefmenoxime, ceftizoxime, cephalothin, cephradine, cefamandol, cephanone, cephapirin, cefroxadin, cefatrizine, cefazedone, ceftrixon and ceforanid; and other β-lactam antibiotics of the clavam, penem and carbapenen type, such as moxalactam, clavulanic acid, nocardicine A, sulbactam, aztreonam and thienamycin; and other antibiotics including bicozamycin, novobiocin, chloramphenicol or thiamphenicol, rifampicin, fosfomycin, colistin, and vancomycin.

Antiviral agents include, but are not limited to, nucleoside analogs, nonnucleoside reverse transcriptase inhibitors, nucleoside reverse transcriptase inhibitors, protease inhibitors, integrase inhibitors, including the following: acemannan; acyclovir; acyclovir sodium; adefovir; alovudine; alvircept sudotox; amantadine hydrochloride; aranotin; arildone;

atevirdine mesylate; avridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscarnet sodium; fosfonet sodium; ganciclovir; ganciclovir sodium; idoxuridine; indinavir; kethoxal; lamivudine; lobucavir; lopinovir; memotine hydrochloride; methisazone; nelfinavir; nevirapine; penciclovir; pirodavir; ribavirin; rimantadine hydrochloride; ritonavir; saquinavir mesylate; somantadine hydrochloride; sorivudine; statolon; stavudine; tenofovir; tilorone hydrochloride; trifluridine; valacyclovir hydrochloride; vidarabine; vidarabine phosphate; vidarabine sodium phosphate; viroxime; zalcitabine; zerit; zidovudine (AZT); and zinviroxime.

Anti-infective agents include, but are not limited to, difloxacin hydrochloride; lauryl isoquinolinium bromide; moxalactam disodium; ornidazole; pentisomicin; sarafloxacin hydrochloride; protease inhibitors of HIV and other retroviruses; integrase Inhibitors of HIV and other retroviruses; cefaclor (ceclor); acyclovir (zovirax); norfloxacin (noroxin); cefoxitin (mefoxin); cefuroxime axetil (ceftin); ciprofloxacin (cipro); aminacrine hydrochloride; benzethonium chloride: bithionolate sodium; bromchlorenone; carbamide peroxide; cetalkonium chloride; cetylpyridinium chloride: chlorhexidine hydrochloride; clioquinol; domiphen bromide; fenticlor; fludazonium chloride; fuchsin, basic; furazolidone; gentian violet; halquinols; hexachlorophene: hydrogen peroxide; ichthammol; imidecyl iodine; iodine; isopropyl alcohol; mafenide acetate; meralein sodium; mercufenol chloride; mercury, ammoniated; methylbenzethonium chloride; nitrofurazone; nitromersol; octenidine hydrochloride; oxychlorosene; oxychlorosene sodium; parachlorophenol, camphorated; potassium permanganate; povidone-iodine; sepazonium chloride; silver nitrate; sulfadiazine, silver; symclosene; thimerfonate sodium; thimerosal: troclosene potassium.

Antifungal (antibiotics) include: polyenes such as Amphotericin-B, candicidin, dermostatin, filipin, fungichromin, hachimycin, hamycin, lucensomycin, mepartricin, natamycin, nystatin, pecilocin, perimycin; and others, such as azaserine, griseofulvin, oligomycins, pyrrolnitrin, siccanin, tubercidin and viridin. Antifungal synthetics include: allylamines such as naftifine and terbinafine; imidazoles such as bifonazole, butoconazole, chlordantoin, chlormidazole, cloconazole, clotrimazole, econazole, enilconazole, fenticonazole, isoconazole, ketoconazole, miconazole, omoconazole, oxiconazole nitrate, sulconazole and tioconazole; triazoles such as fluconazole, itraconazole, terconazole. Others include acrisorcin, amorolfine, biphenamine, bromosalicylchloranilide, buclosamide, chlophenesin, ciclopirox, cloxyquin, coparaffinate, diamthazole, dihydrochloride, exalamide, flucytosine, halethazole, hexetidine, loflucarban, nifuratel, potassium iodide, propionates, propionic acid, pyrithione, salicylanilide, sulbentine, tenonitrozole, tolciclate, tolindate, tolnaftate, tricetin, ujothion, and undecylenic acid. Antifungals also include the echinocandin class class or antifungals; including caspofungin, micafungin, anidulafungin, aminocandin, and the like.

Vasoconstrictors include, but are not limited to, epinephrine, norepinephrine, pseudoephedrine, phenylephrine, oxymetazoline, propylhexedrine, naphazoline, tetrahydrolozine, xylometazonline, ethylnorepinephrine, methoxamine, phenylhexedrine, mephentermine, metaraminol, dopamine, dipivefrin, norphedrine and ciraxzoline may be advantageously used in the compositions and methods herein. Use of such should aid in reducing systemic delivery of the active antihyperalgesic agent.

The pharmaceutical preparations of the invention, when used alone or in cocktails, are administered in therapeutically effective amounts. A therapeutically effective amount will be determined by the parameters discussed below; but, in any event, is that amount which establishes a level of the drug(s) effective for treating a subject, such as a human subject, having one of the conditions described herein. An effective amount means that amount alone or with multiple doses, or the rate of delivery necessary to delay the onset of, lessen the severity of, or inhibit completely, lessen the progression of, or halt altogether the onset or progression of the condition being treated or a symptom associated therewith. In the case of diarrhea, an effective amount can be, for example, that amount which results in one or more of the following: 1) decreasing the frequency of bowel movements; 2) increasing the consistency of the stool, and/or 3) decreasing the stool volume to less than 200 g per day. In one embodiment, an effective amount is an amount that results in 3 or less per bowel movments per day, preferably 2 or less per day, more preferably 1 bowel movement per day. In certain instances, the amount is sufficient to decrease bowel movements within 12 hours of administration of the MNTX, 10 hours, 8 hours, 6 hours, 4 hours, 2 hours, 1 hour and even immediately upon administration, depending upon the mode of administration. Intravenous administration can produce an immediate effect. In restoring gastrointestinal function, an effective amount can be, for example, that amount necessary to increase oral-cecal transit time. For management or treatment of pain, an effective amount can be, for example, that amount to sufficient to make a subject more comfortable as determined by subjective criteria, objective criteria or both. In the case of peripheral hyperalgesia, an effective amount can be, for example, that amount which relieves a symptom of peripheral hyperalgesia such as hypersensitivity to pain or pruritis. For the prevention or treatment of inflammation, an effective amount can be, for example, the amount sufficient to reduce or lessen the redness, swelling, or tissue damage associated with the inflammation or to increase the mobility of an affected area such as a joint. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation.

Generally, oral doses of S-MNTX will be from about 0.05 to about 40 mg/kg, from 0.05 to about 20.0 mg/kg, from about 0.05 to about 10 mg/kg, or from about 0.05 to about 5 mg/kg body weight per day. Generally, parenteral administration, including intravenous and subcutaneous administration, will be from about 0.001 to 1.0 mg/kg, from about 0.01 to 1.0 mg/kg, or from about 0.1 to 1.0 mg/kg body weight depending on whether administration is as a bolus or is spread out over time such as with an I.V. drip. It is expected that doses ranging from about 0.05 to 0.5 mg/kg body weight will yield the desired results. Dosage may be adjusted appropriately to achieve desired drug levels, local or systemic, depending on the mode of administration. For example, it is expected that the dosage for oral administration of the S-MNTX in an enterically-coated formulation would be lower than in an immediate release oral formulation. In the event that the response in a patient is insufficient at such doses, even higher doses (or effectively higher dosage by a different, more localized delivery route) may be employed to the extent that the patient tolerance permits. Multiple doses per day are contemplated to achieve appropriate systemic levels of compounds.

Appropriate systemic levels can be determined by, for example, measurement of the patient's peak or sustained plasma level of the drug. "Dose" and "dosage" are used interchangeably herein.

A variety of administration routes are available. The particular mode selected will depend, of course, upon the particular combination of drugs selected, the severity of the condition being treated, or prevented, the condition of the patient, and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, transdermal, sublingual, intravenous infusion, pulmonary, intra-arterial, intra-adipose tissue, intra-lymphatic, intramuscular, intracavity, aerosol, aural (e.g., via eardrops), intranasal, inhalation, intra-articular, needleless injection, subcutaneous or intradermal (e.g., transdermal) delivery. For continuous infusion, a patient-controlled analgesia (PCA) device or an implantable drug delivery device may be employed. Oral, rectal, or topical administration may be important for prophylactic or long-term treatment. Preferred rectal modes of delivery include administration as a suppository or enema wash.

The pharmaceutical preparations may conveniently be presented in unit dosage form and may be prepared by any of the methods well known in the art of pharmacy. All methods include the step of bringing the compounds of the invention into association with a carrier which constitutes one or more accessory ingredients. In general, the compositions are prepared by uniformly and intimately bringing the compounds of the invention into association with a liquid carrier, a finely divided solid carrier, or both, and then, if necessary, shaping the product.

When administered, the pharmaceutical preparations of the invention are applied in pharmaceutically acceptable compositions. Such preparations may routinely contain salts, buffering agents, preservatives, compatible carriers, lubricants, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, p-toluenesulfonic, tartaric, citric, methanesulfonic, formic, succinic, naphthalene-2-sulfonic, pamoic, 3-hydroxy-2-naphthalenecarboxylic, and benzene sulfonic.

It should be understood that when referring to MNTX, R- and S-MNTX, and therapeutic agent(s) of the invention, it is meant to encompass salts of the same. Such salts are of a variety well known to those or ordinary skill in the art. When used in pharmaceutical preparations, the salts preferably are pharmaceutically-acceptable for use in humans. Bromide is an example of one such salt.

The pharmaceutical preparations of the present invention may include or be diluted into a pharmaceutically-acceptable carrier. The term "pharmaceutically-acceptable carrier" as used herein means one or more compatible solid or liquid fillers, diluents or encapsulating substances which are suitable for administration to a human or other mammal such as non-human primate, a dog, cat, horse, cow, sheep, pig, or goat. The term "carrier" denotes an organic or inorganic ingredient, natural or synthetic, with which the active ingredient is combined to facilitate the application. The carriers are capable of being commingled with the preparations of the present invention, and with each other, in a manner such that there is no interaction which would substantially impair the desired pharmaceutical efficacy or stability. Carrier formulations suitable for oral administration, for suppositories, and for parenteral administration, etc., can be found in Remington's Pharmaceutical Sciences, Mack Publishing Company, Easton, Pa.

Aqueous formulations may include a chelating agent, a buffering agent, an anti-oxidant and, optionally, an isotonicity agent, preferably pH adjusted to between 3.0 and 3.5. Examples of such formulations that are stable to autoclaving and long term storage are described in co-pending U.S. application Ser. No. 10/821,811, entitled "Pharmaceutical Formulation."

Chelating agents include, for example, ethylenediaminetetraacetic acid (EDTA) and derivatives thereof, citric acid and derivatives thereof, niacinamide and derivatives thereof, sodium desoxycholate and derivatives thereof, and L-glutamic acid, N, N-diacetic acid and derivatives thereof.

Buffering agents include those selected from the group consisting of citric acid, sodium citrate, sodium acetate, acetic acid, sodium phosphate and phosphoric acid, sodium ascorbate, tartaric acid, maleic acid, glycine, sodium lactate, lactic acid, ascorbic acid, imidazole, sodium bicarbonate and carbonic acid, sodium succinate and succinic acid, histidine, and sodium benzoate and benzoic acid, or combinations thereof.

Antioxidants include those selected from the group consisting of an ascorbic acid derivative, butylated hydroxy anisole, butylated hydroxy toluene, alkyl gallate, sodium metabisulfite, sodium bisulfite, sodium dithionite, sodium thioglycollate acid, sodium formaldehyde sulfoxylate, tocopheral and derivatives thereof, monothioglycerol, and sodium sulfite. The preferred antioxidant is monothioglycerol.

Isotonicity agents include those selected from the group consisting of sodium chloride, mannitol, lactose, dextrose, glycerol, and sorbitol.

Preservatives that can be used with the present compositions include benzyl alcohol, parabens, thimerosal, chlorobutanol and preferably benzalkonium chloride. Typically, the preservative will be present in a composition in a concentration of up to about 2% by weight. The exact concentration of the preservative, however, will vary depending upon the intended use and can be easily ascertained by one skilled in the art.

The compounds of the invention can be prepared in lyophilized compositions, preferably in the presence of a cryoprotecting agent such as mannitol, or lactose, sucrose, polyethylene glycol, and polyvinyl pyrrolidines. Cryoprotecting agents which result in a reconstitution pH of 6.0 or less are preferred. The invention therefore provides a lyophilized preparation of therapeutic agent(s) of the invention. The preparation can contain a cryoprotecting agent, such as mannitol or lactose, which is preferably neutral or acidic in water.

Oral, parenteral and suppository formulations of agents are well known and commercially available. The therapeutic agent(s) of the invention can be added to such well known formulations. It can be mixed together in solution or semi-solid solution in such formulations, can be provided in a suspension within such formulations or could be contained in particles within such formulations.

A product containing therapeutic agent(s) of the invention and, optionally, one or more other active agents can be configured as an oral dosage. The oral dosage may be a liquid, a semisolid or a solid. An opioid may optionally be included in the oral dosage. The oral dosage may be configured to release the therapeutic agent(s) of the invention before, after or simultaneously with the other agent (and/or the opioid). The oral dosage may be configured to have the therapeutic agent(s) of the invention and the other agents release completely in the stomach, release partially in the stomach and partially in the intestine, in the intestine, in the colon, partially in the stomach, or wholly in the colon. The oral dosage also may be configured whereby the release of the therapeutic agent(s) of the invention is confined to the stomach or intestine while the release of the other active agent is not so confined or is confined differently from the therapeutic agent(s) of the invention. For example, the therapeutic agent(s) of the invention may be an enterically coated core or pellets contained within a pill or capsule that releases the other agent first and releases the therapeutic agent(s) of the invention only after the therapeutic agent(s) of the invention passes through the stomach and into the intestine. The therapeutic agent(s) of the invention also can be in a sustained release material, whereby the therapeutic agent(s) of the invention is released throughout the gastrointestinal tract and the other agent is released on the same or a different schedule. The same objective for therapeutic agent(s) of the invention release can be achieved with immediate release of therapeutic agent(s) of the invention combined with enteric coated therapeutic agent(s) of the invention. In these instances, the other agent could be released immediately in the stomach, throughout the gastrointestinal tract or only in the intestine.

The materials useful for achieving these different release profiles are well known to those of ordinary skill in the art. Immediate release is obtainable by conventional tablets with binders which dissolve in the stomach. Coatings which dissolve at the pH of the stomach or which dissolve at elevated temperatures will achieve the same purpose. Release only in the intestine is achieved using conventional enteric coatings such as pH sensitive coatings which dissolve in the pH environment of the intestine (but not the stomach) or coatings which dissolve over time. Release throughout the gastrointestinal tract is achieved by using sustained-release materials and/or combinations of the immediate release systems and sustained and/or delayed intentional release systems (e.g., pellets which dissolve at different pHs).

In the event that it is desirable to release the therapeutic agent(s) of the invention first, the therapeutic agent(s) of the invention could be coated on the surface of the controlled release formulation in any pharmaceutically acceptable carrier suitable for such coatings and for permitting the release of the therapeutic agent(s) of the invention, such as in a temperature sensitive pharmaceutically acceptable carrier used for controlled release routinely. Other coatings which dissolve when placed in the body are well known to those of ordinary skill in the art.

The therapeutic agent(s) of the invention also may be mixed throughout a controlled release formulation, whereby it is released before, after or simultaneously with another agent. The therapeutic agent(s) of the invention may be free, that is, solubilized within the material of the formulation. The therapeutic agent(s) of the invention also may be in the form of vesicles, such as wax coated micropellets dispersed throughout the material of the formulation. The coated pellets can be fashioned to immediately release the therapeutic agent(s) of the invention based on temperature, pH or the like. The pellets also can be configured so as to delay the release of the therapeutic agent(s) of the invention, allowing the other agent a period of time to act before the therapeutic agent(s) of the invention exerts its effects. The therapeutic agent(s) of the invention pellets also can be configured to release the therapeutic agent(s) of the invention in virtually any sustained release pattern, including patterns exhibiting first order release kinetics or sigmoidal order release kinetics using materials of the prior art and well known to those of ordinary skill in the art.

The therapeutic agent(s) of the invention also can be contained within a core within the controlled release formulation. The core may have any one or any combination of the properties described above in connection with the pellets. The therapeutic agent(s) of the invention may be, for example, in a core coated with a material, dispersed throughout a material, coated onto a material or adsorbed into or throughout a material.

It should be understood that the pellets or core may be of virtually any type. They may be drug coated with a release material, drug interspersed throughout material, drug adsorbed into a material, and so on. The material may be erodible or nonerodible.

The therapeutic agent(s) of the invention, may be provided in particles. Particles as used herein means nano or microparticles (or in some instances larger) which can consist in whole or in part of the therapeutic agent(s) of the inventions or the other agents as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the antagonist in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as nonimmediate release formulations, with nonimmediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug therefrom. "Delayed release" may or may not involve gradual release of drug over an extended period of time, and thus may or may not be "sustained release." These formulations may be for any mode of administration.

Delivery systems specific for the gastrointestinal tract are roughly divided into three types: the first is a delayed release system designed to release a drug in response to, for example, a change in pH; the second is a timed-release system designed to release a drug after a predetermined time; and the third is a microflora enzyme system making use of the abundant enterobacteria in the lower part of the gastrointestinal tract (e.g., in a colonic site-directed release formulation).

An example of a delayed release system is one that uses, for example, an acrylic or cellulosic coating material and dissolves on pH change. Because of ease of preparation, many reports on such "enteric coatings" have been made. In general, an enteric coating is one which passes through the stomach without releasing substantial amounts of drug in the stomach (i.e., less than 10% release, 5% release and even 1% release in the stomach) and sufficiently disintegrating in the intestinal tract (by contact with approximately neutral or alkaline intestine juices) to allow the transport (active or passive) of the active agent through the walls of the intestinal tract.

Various in vitro tests for determining whether or not a coating is classified as an enteric coating have been published in the pharmacopoeia of various countries. A coating which remains intact for at least 2 hours, in contact with artificial gastric juices such as HCl of pH 1 at 36 to 38° C. and thereafter disintegrates within 30 minutes in artificial intestinal juices such as a $KH_2PO_4$ buffered solution of pH 6.8 is one example. One such well known system is EUDRAGIT material, commercially available and reported on by Behringer, Manchester University, Saale Co., and the like. Enteric coatings are discussed further, below.

A timed release system is represented by Time Erosion System (TES) by Fujisawa Pharmaceutical Co., Ltd. and Pulsincap by R. P. Scherer. According to these systems, the site of drug release is decided by the time of transit of a preparation in the gastrointestinal tract. Since the transit of a preparation in the gastrointestinal tract is largely influenced by the gastric emptying time, some time release systems are also enterically coated.

Systems making use of the enterobacteria can be classified into those utilizing degradation of azoaromatic polymers by an azo reductase produced from enterobacteria as reported by the group of Ohio University (M. Saffran, et al., Science, Vol. 233: 1081 (1986)) and the group of Utah University (J. Kopecek, et al., Pharmaceutical Research, 9(12), 1540-1545 (1992)); and those utilizing degradation of polysaccharides by beta-galactosidase of enterobacteria as reported by the group of Hebrew University (unexamined published Japanese patent application No. 5-50863 based on a PCT application) and the group of Freiberg University (K. H. Bauer et al., Pharmaceutical Research, 10(10), S218 (1993)). In addition, the system using chitosan degradable by chitosanase by Teikoku Seiyaku K. K. (unexamined published Japanese patent application No. 4-217924 and unexamined published Japanese patent application No. 4-225922) is also included.

The enteric coating is typically, although not necessarily, a polymeric material. Preferred enteric coating materials comprise bioerodible, gradually hydrolyzable and/or gradually water-soluble polymers. The "coating weight," or relative amount of coating material per capsule, generally dictates the time interval between ingestion and drug release. Any coating should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention. The selection of the specific enteric coating material will depend on the following properties: resistance to dissolution and disintegration in the stomach; impermeability to gastric fluids and drug/carrier/enzyme while in the stomach; ability to dissolve or disintegrate rapidly at the target intestine site; physical and chemical stability during storage; non-toxicity; ease of application as a coating (substrate friendly); and economical practicality.

Suitable enteric coating materials include, but are not limited to: cellulosic polymers such as cellulose acetate phthalate, cellulose acetate trimellitate, hydroxypropylmethyl cellulose phthalate, hydroxypropyhmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl methacrylate (e.g., those copolymers sold under the trade name EUDRAGIT); vinyl polymers and copolymers such as polyvinyl acetate, polyvinylacetate phthalate, vinylacetate crotonic acid copolymer, and ethylene-vinyl acetate copolymers; and shellac (purified lac). Combinations of different coating materials may also be used. Well known enteric coating material for use herein are those acrylic acid polymers and copolymers available under the trade name EUDRAGIT from Rohm Pharma (Germany). The EUDRAGIT series E, L, S, RL, RS and NE copolymers are available as solubilized in organic solvent, as an aqueous dispersion, or as a dry powder. The EUDRAGIT series RL, NE, and RS copolymers are insoluble in the gastrointestinal tract but are permeable and are used primarily for extended release. The EUDRAGIT series E copolymers dissolve in the stomach. The EUDRAGIT series L, L-30D and S copolymers are insoluble in stomach and dissolve in the intestine, and are thus most preferred herein.

A particular methacrylic copolymer is EUDRAGIT L, particularly L-30D and EUDRAGIT L 100-55. In EUDRAGIT L-30D, the ratio of free carboxyl groups to ester groups is approximately 1:1. Further, the copolymer is known to be insoluble in gastrointestinal fluids having pH below 5.5, generally 1.5-5.5, i.e., the pH generally present in the fluid of the upper gastrointestinal tract, but readily soluble or partially soluble at pH above 5.5, i.e., the pH generally present in the fluid of lower gastrointestinal tract. Another particular methacrylic acid polymer is EUDRAGIT S, which differs from EUDRAGIT L-30D in that the ratio of free carboxyl groups to ester groups is approximately 1:2. EUDRAGIT S is insoluble at pH below 5.5, but unlike EUDRAGIT L-30D, is poorly soluble in gastrointestinal fluids having a pH in the range of 5.5 to 7.0, such as in the small intestine. This copolymer is soluble at pH 7.0 and above, i.e., the pH generally found in the colon. EUDRAGIT S can be used alone as a coating to provide drug delivery in the large intestine. Alternatively, EUDRAGIT S, being poorly soluble in intestinal fluids below pH 7, can be used in combination with EUDRAGIT L-30D, soluble in intestinal fluids above pH 5.5, in order to provide a delayed release composition which can be formulated to deliver the active agent to various segments of the intestinal tract. The more EUDRAGIT L-30D used, the more proximal release and delivery begins, and the more EUDRAGIT S used, the more distal release and delivery begins. It will be appreciated by those skilled in the art that both EUDRAGIT L-30D and EUDRAGIT S can be replaced with other pharmaceutically acceptable polymers having similar pH solubility characteristics. In certain embodiments of the invention, the preferred enteric coating is ACRYL-EZE™ (methacrylic acid co-polymer type C; Colorcon, West Point, Pa.).

The enteric coating provides for controlled release of the active agent, such that drug release can be accomplished at some generally predictable location. The enteric coating also prevents exposure of the therapeutic agent and carrier to the epithelial and mucosal tissue of the buccal cavity, pharynx, esophagus, and stomach, and to the enzymes associated with these tissues. The enteric coating therefore helps to protect the active agent, carrier and a patient's internal tissue from any adverse event prior to drug release at the desired site of delivery. Furthermore, the coated material of the present invention allows optimization of drug absorption, active agent protection, and safety. Multiple enteric coatings targeted to release the active agent at various regions in the gastrointestinal tract would enable even more effective and sustained improved delivery throughout the gastrointestinal tract.

The coating can, and usually does, contain a plasticizer to prevent the formation of pores and cracks that would permit the penetration of the gastric fluids. Suitable plasticizers include, but are not limited to, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating comprised of an anionic carboxylic acrylic polymer will usually contain approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance and the coated product.

The coating can be applied to particles of the therapeutic agent(s), tablets of the therapeutic agent(s), capsules containing the therapeutic agent(s) and the like, using conventional coating methods and equipment. For example, an enteric coating can be applied to a capsule using a coating pan, an airless spray technique, fluidized bed coating equipment, or the like. Detailed information concerning materials, equipment and processes for preparing coated dosage forms may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, 6th Ed. (Media, Pa.: Williams & Wilkins, 1995). The coating thickness, as noted above, must be sufficient to ensure that the oral dosage form remains intact until the desired site of topical delivery in the lower intestinal tract is reached.

In another embodiment, drug dosage forms are provided that comprise an enterically coated, osmotically activated device housing a formulation of the invention. In this embodiment, the drug-containing formulation is encapsulated in a semipermeable membrane or barrier containing a small orifice. As known in the art with respect to so-called "osmotic pump" drug delivery devices, the semipermeable membrane allows passage of water in either direction, but not drug. Therefore, when the device is exposed to aqueous fluids, water will flow into the device due to the osmotic pressure differential between the interior and exterior of the device. As water flows into the device, the drug-containing formulation in the interior will be "pumped" out through the orifice. The rate of drug release will be equivalent to the inflow rate of water times the drug concentration. The rate of water influx and drug efflux can be controlled by the composition and size of the orifice of the device. Suitable materials for the semipermeable membrane include, but are not limited to, polyvinyl alcohol, polyvinyl chloride, semipermeable polyethylene glycols, semipermeable polyurethanes, semipermeable polyamides, semipermeable sulfonated polystyrenes and polystyrene derivatives; semipermeable poly(sodium styrenesulfonate), semipermeable poly(vinylbenzyltrimethylammonium chloride), and cellulosic polymers such as cellulose acetate, cellulose diacetate, cellulose triacetate, cellulose propionate, cellulose acetate propionate, cellulose acetate butyrate, cellulose trivalerate, cellulose trilmate, cellulose tripalmitate, cellulose trioctanoate, cellulose tripropionate, cellulose disuccinate, cellulose dipalmitate, cellulose dicylate, cellulose acetate succinate, cellulose propionate succinate, cellulose acetate octanoate, cellulose valerate palmitate, cellulose acetate heptanate, cellulose acetaldehyde dimethyl acetal, cellulose acetate ethylcarbamate, cellulose acetate methylcarbamate, cellulose dimethylaminoacetate and ethylcellulose.

In another embodiment, drug dosage forms are provided that comprise a sustained release coated device housing a formulation of the invention. In this embodiment, the drug-containing formulation is encapsulated in a sustained release membrane or film. The membrane may be semipermeable, as described above. A semipermeable membrane allows for the passage of water inside the coated device to dissolve the drug. The dissolved drug solution diffuses out through the semipermeable membrane. The rate of drug release depends upon the thickness of the coated film and the release of drug can begin in any part of the GI tract Suitable membrane materials for such a membrane include ethylcellulose.

In another embodiment, drug dosage forms are provided that comprise a sustained release device housing a formulation of the invention. In this embodiment, the drug-containing formulation is uniformly mixed with a sustained release polymer. These sustained release polymers are high molecular weight water-soluble polymers, which when in contact with water, swell and create channels for water to diffuse inside and dissolve the drug. As the polymers swell and dissolve in water, more of drug is exposed to water for dissolution. Such a system is generally referred to as sustained release matrix. Suitable materials for such a device include hydropropyl methylcellulose, hydroxypropyl cellulose, hydroxyethyl cellulose and methyl cellulose.

In another embodiment, drug dosage forms are provided that comprise an enteric coated device housing a sustained release formulation of the invention. In this embodiment, the drug containing product described above is coated with an enteric polymer. Such a device would not release any drug in the stomach and when the device reaches the intestine, the enteric polymer is first dissolved and only then would the drug release begin. The drug release would take place in a sustained release fashion.

Enterically coated, osmotically activated devices can be manufactured using conventional materials, methods and equipment. For example, osmotically activated devices may be made by first encapsulating, in a pharmaceutically acceptable soft capsule, a liquid or semi-solid formulation of the compounds of the invention as described previously. This interior capsule is then coated with a semipermeable membrane composition (comprising, for example, cellulose acetate and polyethylene glycol 4000 in a suitable solvent such as a methylene chloride-methanol admixture), for example using an air suspension machine, until a sufficiently thick laminate is formed, e.g., around 0.05 mm. The semipermeable laminated capsule is then dried using conventional techniques. Then, an orifice having a desired diameter (e.g., about 0.99 mm) is provided through the semipermeable laminated capsule wall, using, for example, mechanical drilling, laser drilling, mechanical rupturing, or erosion of an erodible element such as a gelatin plug. The osmotically activated device may then be enterically coated as previously described. For osmotically activated devices containing a solid carrier rather than a liquid or semi-solid carrier, the interior capsule is optional; that is, to the semipermeable membrane may be formed directly around the carrier-drug composition. However, preferred carriers for use in the drug-containing formulation of the osmotically activated device are solutions, suspensions, liquids, immiscible liquids, emulsions, sols, colloids, and oils. Particularly preferred carriers include, but are not limited to, those used for enterically coated capsules containing liquid or semisolid drug formulations.

Cellulose coatings include those of cellulose acetate phthalate and trimellitate; methacrylic acid copolymers, e.g. copolymers derived from methylacrylic acid and esters thereof, containing at least 40% methylacrylic acid; and especially hydroxypropyl methylcellulose phthalate. Methylacrylates include those of molecular weight above 100,000 daltons based on, e.g. methylacrylate and methyl or ethyl methylacrylate in a ratio of about 1:1. Typical products include Endragit L, e.g. L 100-55, marketed by Rohm GmbH, Darmstadt, Germany. Typical cellulose acetate phthalates have an acetyl content of 17-26% and a phthalate content of from 30-40% with a viscosity of ca. 45-90 cP. Typical cellulose acetate trimellitates have an acetyl content of 17-26%, a trimellityl content from 25-35% with a viscosity of ca. 15-20 cS. An example of a cellulose acetate trimellitate is the marketed product CAT (Eastman Kodak Company, USA). Hydroxypropyl methylcellulose phthalates typically have a molecular weight of from 20,000 to 130,000 daltons, a hydroxypropyl content of from 5 to 10%, a methoxy content of from 18 to 24% and a phthalyl content from 21 to 35%. An example of a cellulose acetate phthalate is the marketed product CAP (Eastman Kodak, Rochester N.Y., USA). Examples of hydroxypropyl methylcellulose phthalates are the marketed products having a hydroxypropyl content of from 6-10%, a methoxy content of from 20-24%, a phthalyl content of from 21-27%, a molecular weight of about 84,000 daltons, sold under the trademark HP50 and available from Shin-Etsu Chemical Co. Ltd., Tokyo, Japan, and having a hydroxypropyl content, a methoxyl content, and a phthalyl content of 5-9%, 18-22% and 27-35%, respectively, and a molecular weight of 78,000 daltons, known under the trademark HP55 and available from the same supplier.

The therapeutic agents may be provided in capsules, coated or not. The capsule material may be either hard or soft, and as will be appreciated by those skilled in the art, typically comprises a tasteless, easily administered and water soluble compound such as gelatin, starch or a cellulosic material. The capsules are preferably sealed, such as with gelatin bands or the like. See, for example, Remington: The Science and Practice of Pharmacy, Nineteenth Edition (Easton, Pa.: Mack Publishing Co., 1995), which describes materials and methods for preparing encapsulated pharmaceuticals.

A product containing therapeutic agent(s) of the invention can be configured as a suppository. The therapeutic agent(s) of the invention can be placed anywhere within or on the suppository to favorably affect the relative release of the therapeutic agent(s). The nature of the release can be zero order, first order, or sigmoidal, as desired.

Suppositories are solid dosage forms of medicine intended for administration via the rectum. Suppositories are compounded so as to melt, soften, or dissolve in the body cavity (around 98.6° F.) thereby releasing the medication contained therein. Suppository bases should be stable, nonirritating, chemically inert, and physiologically inert. Many commercially available suppositories contain oily or fatty base materials, such as cocoa butter, coconut oil, palm kernel oil, and palm oil, which often melt or deform at room temperature necessitating cool storage or other storage limitations. U.S. Pat. No. 4,837,214 to Tanaka et al. describes a suppository base comprised of 80 to 99 percent by weight of a lauric-type fat having a hydroxyl value of 20 or smaller and containing glycerides of fatty acids having 8 to 18 carbon atoms combined with 1 to 20 percent by weight diglycerides of fatty acids (which erucic acid is an example of). The shelf life of these type of suppositories is limited due to degradation. Other suppository bases contain alcohols, surfactants, and the like which raise the melting temperature but also can lead to poor absorption of the medicine and side effects due to irritation of the local mucous membranes (see for example, U.S. Pat. No. 6,099,853 to Hartelendy et al., U.S. Pat. No. 4,999, 342 to Ahmad et al., and U.S. Pat. No. 4,765,978 to Abidi et al.).

The base used in the pharmaceutical suppository composition of this invention includes, in general, oils and fats comprising triglycerides as main components such as cacao butter, palm fat, palm kernel oil, coconut oil, fractionated coconut oil, lard and WITEPSOL®, waxes such as lanolin and reduced lanolin; hydrocarbons such as VASELINE®, squalene, squalane and liquid paraffin; long to medium chain fatty acids such as caprylic acid, lauric acid, stearic acid and oleic acid; higher alcohols such as lauryl alcohol, cetanol and stearyl alcohol; fatty acid esters such as butyl stearate and dilauryl malonate; medium to long chain carboxylic acid esters of glycerin such as triolein and tristearin; glycerin-substituted carboxylic acid esters such as glycerin to acetoacetate; and polyethylene glycols and its derivatives such as macrogols and cetomacrogol. They may be used either singly or in combination of two or more. If desired, the composition of this invention may further include a surface-active agent, a coloring agent, etc., which are ordinarily used in suppositories.

The pharmaceutical composition of this invention may be prepared by uniformly mixing predetermined amounts of the active ingredient, the absorption aid and optionally the base, etc. in a stirrer or a grinding mill, if required at an elevated temperature. The resulting composition, may be formed into a suppository in unit dosage form by, for example, casting the mixture in a mold, or by forming it into a gelatin capsule using a capsule filling machine.

The compositions according to the present invention also can be administered as a nasal spray, nasal drop, suspension, gel, ointment, cream or powder. The administration of a composition can also include using a nasal tampon or a nasal sponge containing a composition of the present invention.

The nasal delivery systems that can be used with the present invention can take various forms including aqueous preparations, non-aqueous preparations and combinations thereof. Aqueous preparations include, for example, aqueous gels, aqueous suspensions, aqueous liposomal dispersions, aqueous emulsions, aqueous microemulsions and combinations thereof. Non-aqueous preparations include, for example, non-aqueous gels, non-aqueous suspensions, non-aqueous liposomal dispersions, non-aqueous emulsions, non-aqueous microemulsions and combinations thereof. The various forms of the nasal delivery systems can include a buffer to maintain pH, a pharmaceutically acceptable thickening agent and a humectant. The pH of the buffer can be selected to optimize the absorption of the therapeutic agent(s) across the nasal mucosa.

With respect to the non-aqueous nasal formulations, suitable forms of buffering agents can be selected such that when the formulation is delivered into the nasal cavity of a mammal, selected pH ranges are achieved therein upon contact with, e.g., a nasal mucosa. In the present invention, the pH of the compositions should be maintained from about 2.0 to about 6.0. It is desirable that the pH of the compositions is one which does not cause significant irritation to the nasal mucosa of a recipient upon administration.

The viscosity of the compositions of the present invention can be maintained at a desired level using a pharmaceutically acceptable thickening agent. Thickening agents that can be used in accordance with the present invention include methyl cellulose, xanthan gum, carboxymethyl cellulose, hydroxypropyl cellulose, carbomer, polyvinyl alcohol, alginates, acacia, chitosans and combinations thereof. The concentration of the thickening agent will depend upon the agent selected and the viscosity desired. Such agents can also be used in a powder formulation discussed above.

The compositions of the present invention can also include a humectant to reduce or prevent drying of the mucus membrane and to prevent irritation thereof. Suitable humectants that can be used in the present invention include sorbitol, mineral oil, vegetable oil and glycerol; soothing agents; membrane conditioners; sweeteners; and combinations thereof. The concentration of the humectant in the present compositions will vary depending upon the agent selected.

One or more therapeutic agents may be incorporated into the nasal delivery system or any other delivery system described herein.

A composition formulated for topical administration may be liquid or semi-solid (including, for example, a gel, lotion, emulsion, cream, ointment, spray or aerosol) or may be provided in combination with a "finite" carrier, for example, a non-spreading material that retains its form, including, for example, a patch, bioadhesive, dressing or bandage. It may be aqueous or non-aqueous; it may be formulated as a solution, emulsion, dispersion, a suspension or any other mixture.

Important modes of administration include topical application to the skin, eyes or mucosa. Thus, typical vehicles are those suitable for pharmaceutical or cosmetic application to body surfaces. The compositions provided herein may be applied topically or locally to various areas in the body of a patient. As noted above, topical application is intended to refer to application to the tissue of an accessible body surface, such as, for example, the skin (the outer integument or covering) and the mucosa (the mucous-producing, secreting and/or containing surfaces). Exemplary mucosal surfaces include the mucosal surfaces of the eyes, mouth (such as the lips, tongue, gums, cheeks, sublingual and roof of the mouth), larynx, esophagus, bronchial, nasal passages, vagina and rectum/anus; in some embodiments, preferably the mouth, larynx, esophagus, vagina and rectum/anus; in other embodiments, preferably the eyes, larynx, esophagus, bronchial, nasal passages, and vagina and rectum/anus. As noted above, local application herein refers to application to a discrete internal area of the body, such as, for example, a joint, soft tissue area (such as muscle, tendon, ligaments, intraocular or other fleshy internal areas), or other internal area of the body. Thus, as used herein, local application refers to applications to discrete areas of the body.

With respect to topical and/or local administration of the present compositions, desirable efficacy may involve, for example, penetration of therapeutic agent(s) of the invention into the skin and/or tissue to substantially reach a hyperalgesic site to provide desirable anti-hyperalgesic pain relief. The efficacy of the present compositions may be about the same as that achieved, for example, with central opiate analgesics. But, as discussed in detail herein, the efficacy achieved with therapeutic agent(s) of the invention is preferably obtained without the undesirable effects that are typically associated with central opiates including, for example, respiratory depression, sedation, and addiction, as it is believed that therapeutic agent(s) of the invention does not cross the blood brain barrier.

Also in certain preferred embodiments, including embodiments that involve aqueous vehicles, the compositions may also contain a glycol, that is, a compound containing two or more hydroxy groups. A glycol which is particularly preferred for use in the compositions is propylene glycol. In these preferred embodiments, the glycol is preferably included in the compositions in a concentration of from greater than 0 to about 5 wt. %, based on the total weight of the composition. More preferably, the compositions contain from about 0.1 to less than about 5 wt. % of a glycol, with from about 0.5 to about 2 wt. % being even more preferred. Still more preferably, the compositions contain about 1 wt. % of a glycol.

For local internal administration, such as intra-articular administration, the compositions are preferably formulated as a solution or a suspension in an aqueous-based medium, such as isotonically buffered saline or are combined with a biocompatible support or bioadhesive intended for internal administration.

Lotions, which, for example, may be in the form of a suspension, dispersion or emulsion, contain an effective concentration of one or more of the compounds. The effective concentration is preferably to deliver an effective amount, typically at a concentration of between about 0.1-50% [by weight] or more of one or more of the compounds provided herein. The lotions also contain [by weight] from 1% to 50% of an emollient and the balance water, a suitable buffer, and other agents as described above. Any emollients known to those of skill in the art as suitable for application to human skin may be used. These include, but are not limited to, the following: (a) Hydrocarbon oils and waxes, including mineral oil, petrolatum, paraffin, ceresin, ozokerite, microcrystalline wax, polyethylene, and perhydrosqualene. b) Silicone oils, including dimethylpolysiloxanes, methylphenylpolysiloxanes, water-soluble and alcohol-soluble silicone-glycol copolymers. (c) Triglyceride fats and oils, including those derived from vegetable, animal and marine sources. Examples include, but are not limited to, castor oil, safflower oil, cotton seed oil, corn oil, olive oil, cod liver oil, almond oil, avocado oil, palm oil, sesame oil, and soybean oil. (d) Acetoglyceride esters, such as acetylated monoglycerides. (e) Ethoxylated glycerides, such as ethoxylated glyceryl monstearate. (f) Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, isopropyl myristate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate. (g) Alkenyl esters of fatty acids having 10 to 20 carbon atoms. Examples thereof include, but are not limited to, oleyl myristate, oleyl stearate, and oleyl oleate. (h) Fatty acids having 9 to 22 carbon atoms. Suitable examples include, but are not limited to, pelargonic, lauric, myristic, palmitic, stearic, isostearic, hydroxystearic, oleic, linoleic, ricinoleic, arachidonic, behenic, and erucic acids. (i) Fatty alcohols having 10 to 22 carbon atoms, such as, but not limited to, lauryl, myristyl, cetyl, hexadecyl, stearyl, isostearyl, hydroxystearyl, oleyl, ricinoleyl, behenyl, erucyl, and 2-octyl dodecyl alcohols. (j) Fatty alcohol ethers, including, but not limited to ethoxylated fatty alcohols of 10 to 20 carbon atoms, such as, but are not limited to, the lauryl, cetyl, stearyl, isostearyl, oleyl, and cholesterol alcohols having attached thereto from 1 to 50 ethylene oxide groups or 1 to 50 propylene oxide groups or mixtures thereof. (k) Ether-esters, such as fatty acid esters of ethoxylated fatty alcohols. (1) Lanolin and derivatives, including, but not limited to, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases. (m) polyhydric alcohols and polyether derivatives, including, but not limited to, propylene glycol, dipropylene glycol, polypropylene glycol [M.W. 2000-4000], polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol [M.W. 200-6000], methoxy polyethylene glycols 350, 550, 750, 2000, 5000, poly(ethylene oxide) homopolymers [M.W. 100,000-5,000,000], polyalkylene glycols and derivatives, hexylene glycol (2-methyl-2,4-pentanediol), 1,3-butylene glycol, 1,2,6,-hexanetriol, ethohexadiol USP (2-ethyl-1,3-hexanediol), $C_{15}$-$C_{18}$ vicinal glycol and polyoxypropylene derivatives of trimethylolpropane. (n) polyhydric alcohol esters, including, but not limited to, ethylene glycol mono- and di-fatty acid esters, diethylene glycol mono- and di-fatty acid esters, polyethylene glycol [M.W. 200-6000], mono- and di-fatty esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters. (o) Wax esters, including, but not limited to, beeswax, spermaceti, myristyl myristate, and stearyl stearate and beeswax derivatives, including, but not limited to, polyoxyethylene sorbitol beeswax, which are reaction products of beeswax with ethoxylated sorbitol of varying ethylene oxide content that form a mixture of ether-esters. (p) Vegetable waxes, including, but not limited to, carnauba and candelilla waxes. (q) phospholipids, such as lecithin and derivatives. (r) Sterols, including, but not limited to, cholesterol and cholesterol fatty acid esters. (s) Amides, such as fatty acid amides, ethoxylated fatty acid amides, and solid fatty acid alkanolamides.

The lotions further preferably contain [by weight] from 1% to 10%, more preferably from 2% to 5%, of an emulsifier. The emulsifiers can be nonionic, anionic or cationic. Examples of satisfactory nonionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxide, mono- and di-fatty acid esters of ethylene glycol where the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include, but are not limited to, the fatty acid soaps, e.g., sodium, potassium and triethanolamine soaps, where the fatty acid moiety contains from 10 to 20 carbon atoms. Other suitable anionic emulsifiers include, but are not limited to, the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Among satisfactory cationic emulsifiers are quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably the compound, such as loperamide, is dissolved, suspended or otherwise uniformly dispersed in the mixture.

Other conventional components of such lotions may be included. One such additive is a thickening agent at a level from 1% to 10% by weight of the composition. Examples of suitable thickening agents include, but are not limited to: cross-linked carboxypolymethylene polymers, ethyl cellulose, polyethylene glycols, gum tragacanth, gum kharaya, xanthan gums and bentonite, hydroxyethyl cellulose, and hydroxypropyl cellulose.

Creams can be formulated to contain a concentration effective to deliver an effective amount of therapeutic agent(s) of the invention to the treated tissue, typically at between about 0.1%, preferably at greater than 1% up to and greater than 50%, preferably between about 3% and 50%, more preferably between about 5% and 15% therapeutic agent(s) of the invention. The creams also contain from 5% to 50%, preferably from 10% to 25%, of an emollient and the remainder is water or other suitable non-toxic carrier, such as an isotonic buffer. The emollients, as described above for the lotions, can also be used in the cream compositions. The cream may also contain a suitable emulsifier, as described above. The emulsifier is included in the composition at a level from 3% to 50%, preferably from 5% to 20%.

These compositions that are formulated as solutions or suspensions may be applied to the skin, or, may be formulated as an aerosol or foam and applied to the skin as a spray-on. The aerosol compositions typically contain [by weight] from 25% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used as understood in the art in a quantity and under a pressure suitable to expel the contents of the container.

Suitably prepared solutions and suspensions may also be topically applied to the eyes and mucosa. Solutions, particularly those intended for ophthalmic use, may be formulated as 0.01%-10% isotonic solutions, pH about 5-7, with appropriate salts, and preferably containing one or more of the compounds herein at a concentration of about 0.1%, preferably greater than 1%, up to 50% or more. Suitable ophthalmic solutions are known [see, e.g., U.S. Pat. No. 5,116,868, which describes typical compositions of ophthalmic irrigation solutions and solutions for topical application]. Such solutions, which have a pH adjusted to about 7.4, contain, for example, 90-100 mM sodium chloride, 4-6 mM dibasic potassium phosphate, 4-6 mM dibasic sodium phosphate, 8-12 mM sodium citrate, 0.5-1.5 mM magnesium chloride, 1.5-2.5 mM calcium chloride, 15-25 mM sodium acetate, 10-20 mM D.L.-sodium, .β.-hydroxybutyrate and 5-5.5 mM glucose.

Gel compositions can be formulated by simply admixing a suitable thickening agent to the previously described solution or suspension compositions. Examples of suitable thickening agents have been previously described with respect to the lotions.

The gelled compositions contain an effective amount of therapeutic agent(s) of the invention, typically at a concentration of between about 0.1-50% by weight or more of one or more of the compounds provided herein.; from 5% to 75%, preferably from 10% to 50%, of an organic solvent as previously described; from 0.5% to 20%, preferably from 1% to 10% of the thickening agent; the balance being water or other aqueous or non-aqueous carrier, such as, for example, an organic liquid, or a mixture of carriers.

The formulations can be constructed and arranged to create steady state plasma levels. Steady state plasma concentrations can be measured using HPLC techniques, as are known to those of skill in the art. Steady state is achieved when the rate of drug availability is equal to the rate of drug elimination from the circulation. In typical therapeutic settings, the therapeutic agent(s) of the invention will be administered to patients either on a periodic dosing regimen or with a constant infusion regimen. The concentration of drug in the plasma will tend to rise immediately after the onset of administration and will tend to fall over time as the drug is eliminated from the circulation by means of distribution into cells and tissues, by metabolism, or by excretion. Steady state will be obtained when the mean drug concentration remains constant over time. In the case of intermittent dosing, the pattern of the drug concentration cycle is repeated identically in each interval between doses with the mean concentration remaining constant. In the case of constant infusion, the mean drug concentration will remain constant with very little oscillation. The achievement of steady state is determined by means of measuring the concentration of drug in plasma over at least one cycle of dosing such that one can verify that the cycle is being repeated identically from dose to dose. Typically, in an intermittent dosing regimen, maintenance of steady state can be verified by determining drug concentrations at the consecutive troughs of a cycle, just prior to administration of another dose. In a constant infusion regimen where oscillation in the concentration is low, steady state can be verified by any two consecutive measurements of drug concentration.

Figure 7:
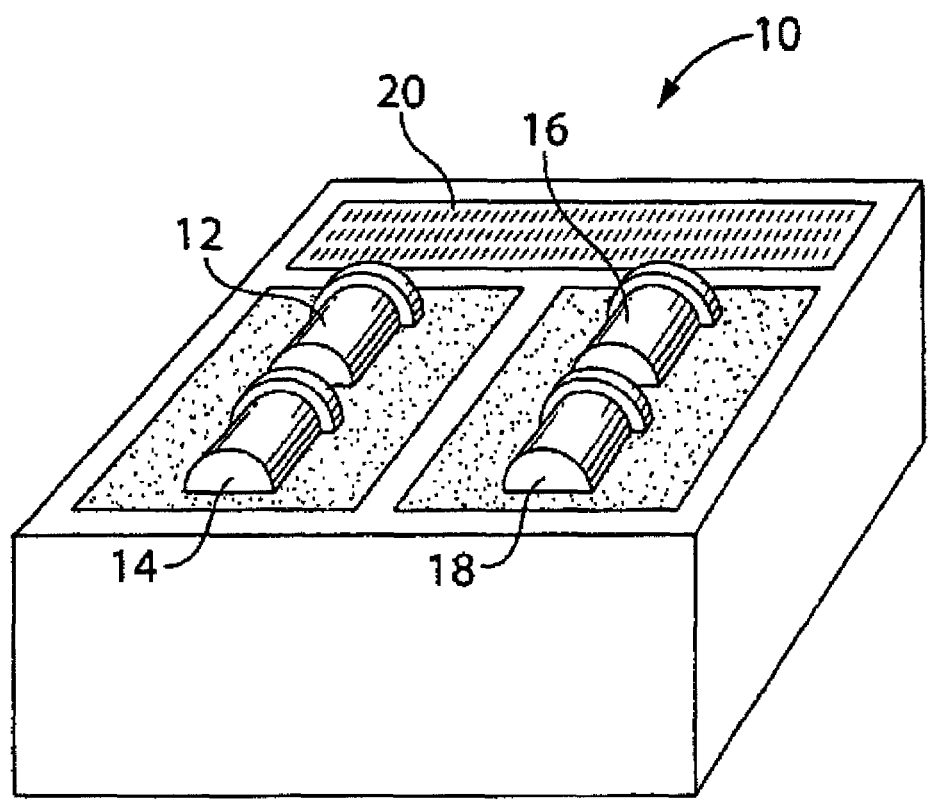
FIG. 7 illustrates a kit according to the invention.

FIG. 7 shows a kit according to the invention. The kit 10 includes a vial 12 containing opioid tablets. The kit 10 also includes a vial 14 containing S-MNTX tablets which comprise pellets, some of which are enterically coated with pH sensitive material and some of which are constructed and arranged to release the S-MNTX immediately in the stomach. The kit also includes instructions 20 for administering the tablets to a subject who has diarrhea or who has symptoms of diarrhea. The instructions include indicia, for example writing, indicating that the S-MNTX is pure S-MNTX free of R-MNTX.

In some aspects of the invention, the kit 10 can include optionally or alternatively a pharmaceutical preparation vial 16 and a pharmaceutical preparation diluent vial 18. The vial containing the diluent for the pharmaceutical preparation is optional. The diluent vial contains a diluent such as physiological saline for diluting what could be a concentrated solution or lyophilized powder of S-MNTX. The instructions can include instructions for mixing a particular amount of the diluent with a particular amount of the concentrated pharmaceutical preparation, whereby a final formulation for injection or infusion is prepared. The instructions 20 can include instructions for treating a patient with an effective amount of S-MNTX. It also will be understood that the containers containing the preparations, whether the container is a bottle, a vial with a septum, an ampoule with a septum, an infusion bag, and the like, can contain additional indicia such as conventional markings which change color when the preparation has been autoclaved or otherwise sterilized.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

EXAMPLES

A number of different synthetic pathways and protocols were attempted to find an efficient method for the production and purification of S-MNTX. A description of some of these are provided below. Also provided are procedures for producing reagents, intermediates and starting materials.

Example I

Deprotection of Oxycodone to Oxymorphone. Oxymorphone was synthesized from oxycodone. The deprotection of oxycodone to oxymorphone was done using conditions previously described in the literature. (Iijima, I.; Minamikawa, J.; Jacobson, A. E.; Brossi, A.; Rice, K. C. *J. Med. Chem.* 1978, 21(4), 398.) Yields ranged from 58-64% with purification consisting of filtration through a short plug of silica gel to remove baseline material. Purified oxymorphone was used for the alkylation reactions. Yields of oxymorphone up to 95% were obtained without purification. HPLC purities of this crude material were typically about 94%.

Preparation of (Iodomethyl)cyclopropane. (Iodomethyl) cyclopropane was prepared from (bromomethyl)cyclopropane through a Finkelstein reaction. Typical yields ranged from 68-70% and typical purities were 89-95% (AUC) by GC, with the starting bromide as the only major impurity.

Direct Alkylation of Oxymorphone. Direct alkylation of oxymorphone with cyclopropylmethyliodide as the alkylating agent proved to give productive yields of S-MNTX. The pathway is illustrated in FIG. 2. The direct alkylation of oxymorphone was observed to proceed to nearly 50% conversion as observed by HPLC (AUC), and was investigated further.

Oxymorphone was combined with cyclopropylmethyl iodide in NMP (10 vol) and heated to 70° C. The results are summarized below in Table 1. The decomposition of the alkylating agent did not completely consume the reagent during the reaction time and thus was not limiting the reaction from proceeding to completion. In addition, the ratio of oxymorphone to S-MNTX showed that the reaction proceeded to nearly 1:1 regardless of the number of equivalents of alkylating agent.

TABLE 1

Investigation Into the Effect of the Equivalents of Alkylating Agent Used

| Entry | Alkyl Iodide (Equiv) | Reaction Composition After 16 Hours at 70° C. (HPLC, AUC) | | |
|---|---|---|---|---|
| | | % Oxymorphone | % S-MNTX | % Alkyl Iodide |
| 1 | 8 | 33 | 30 | 16 |
| 2 | 12 | 29 | 27 | 25 |
| 3 | 16 | 27 | 23 | 35 |
| 4 | 20 | 23 | 20 | 42 |
| 5 | 24 | 22 | 18 | 44 |

Work up procedure. Since the presence of NMP in the crude product was found to prevent retention, a means of removing it was required. A mixture of isopropyl acetate and dioxane formed a flocculent, a light colored solid that eventually became an oil. The use of isopropyl acetate and the mixture of isopropyl acetate/dioxane were compared to determine which was more effective at removing the NMP. In each case, the product and starting material were precipitated from the mixture and NMP remained in solution. Analysis of the supernatant liquid and the precipitated material by HPLC showed no significant difference between the two.

Purification. Once the NMP was removed from the product, the residue was subjected to repetitive sequential reverse-phase chromatography using Biotage Flash chromatography systems, equipped with C18 cartridges. Initial chromatography was carried out using 50% aqueous methanol containing 0.2% HBr as a modifier. The solvent system was incrementally reduced in methanol content until 5% aqueous methanol was settled upon. The chromatography was repeated until S-MNTX was isolated at a purity of 89% (AUC). The counterion was not detectable by MS, but was expected to be a mixture of iodide and bromide.

With the workup and purification defined, the chemistry was scaled up and 28 g of oxycodone·HCl was carried through the process. The first step, demethylation, was carried out in one reaction using the procedure described in the literature and afforded 17 g of oxymorphone, after recrystallization from hot ethanol (10 volumes). The second step was carried out in five equal smaller reactions because of equipment limitations resulting from the size and mode of heating of the pressure tubes. Although analyzed separately, the mixtures were combined for the workup and purification after analysis indicated similar composition. The isopropyl acetate trituration proceeded as expected and the precipitated residue was dissolved into 20% aqueous methanol containing 0.2% HBr and was purified by chromatography on a Biotage Flash 40s, equipped with a C18 cartridge and eluted with 5% aqueous methanol containing 0.2% HBr. The fractions were analyzed by HPLC and the fractions of similar composition were combined, separated into <80%, 80-90%, and <90% purities (AUC). The combined fractions were concentrated and rechromatographed on a Biotage Flash 75L, equipped with a C18 cartridge. This chromatographic procedure was repeated to enhance the purity. Eventually it was discovered that the HBr modifier was unnecessary and was removed from the eluent. After six chromatographic purifications, nearly 11 g of S-MNTX iodide was isolated at approximately 80% purity (AUC).

It became apparent that during the concentration of the fractions that some form of decomposition was occurring and resulted in a significant darkening of the product. The decomposition was attributed to the iodide counterion and, thus, the material was passed through an anion-exchange column to exchange the iodide for bromide. Once the eluent containing product was collected, concentration did not appear to result in the familiar darkening and afforded a yellow oil. The chromatography was continued, separating the product streams by purity level (AUC by HPLC). Once the bulk of the material had been enhanced to approximately 90% purity, additional chromatography was carried out using 2.5% aqueous methanol as the eluent and eventually improved the purity of some material to >95% (AUC).

All the product streams were combined and lyophilized to afford free-flowing powders, 741 mg of S-MNTX was isolated at 95% pure, 2.5 g of S-MNTX was isolated at 90% purity, and 1.0 g of S-MNTX was isolated at 79% purity (AUC). The fractions of recovered oxymorphone were collected and recrystallized from ethanol to afford 2.4.g (>99% purity, AUC).

Reagent Preparation. In a series of experiments directed to producing S-MNTX, starting materials and reagents were obtained or made as described below. Equipment and instrumentation data are also provided.

All nonaqueous reactions were performed under dry nitrogen. Unless otherwise noted, reagents were purchased from commercial sources and used as received. Proton nuclear magnetic resonance spectra were obtained on a Bruker Avance 300 spectrometer at 300 MHz with tetramethylsilane used as an internal reference. Carbon nuclear magnetic resonance spectra were obtained on a Bruker Avance 300 Spectrometer at 75 MHz with the solvent peak used as the reference. Infrared spectra were obtained on a Perkin-Elmer Spectrum 1000 spectrophotometer. Mass spectra were obtained on a Finnigan mass spectrometer.

Thin layer chromatography (TLC) was performed using 2.5×10 cm Analtech Silica Gel GF plates (25 microns thick). Visualization of TLC plates was performed using UV and potassium permanganate stain. HPLC analysis was performed on a Varian ProStar HPLC controlled by Varian Star software using the following method:

HPLC Method I:
Column: Luna C18(2), 150×4.6 mm, 5μ
Flow Rate: 1 mL/min
Detection: UV@230 nm
Gradient Program:

| Time (min) | % A | % B |
|---|---|---|
| 0:00 | 95 | 5 |
| 8:00 | 65 | 35 |
| 12:00 | 35 | 65 |
| 15:00 | 0 | 100 |
| 16:00 | 95 | 5 |
| 18:00 | 95 | 5 |

Mobile phase A = 0.1% Aqueous TFA
Mobile phase B = 0.1% Methanolic TFA

HPLC Method II:
Chromatographic Conditions and Parameters: Analytical Column Description:
Phenomenex Inertsil ODS-3 150×4.6 mm, 5 μm Column Temperature: 50.0° C. Flow Rate: 1.5 mL/min Injection Volume: 20 μL Detection Wavelength: 280 nm Mobile Phase: A=Water: MeOH: TFA (95:5:0.1%; v/v/v) B=Water: MeOH: TFA (35:65:0.1%; v/v/v) Analysis Time: 50 min
Quantitation limit: 0.05%
Detection limit: 0.02%

Gradient Profile:

| Time (min) | % A | % B | Curve |
|---|---|---|---|
| 0:00 | 100 | 0 | Initial |
| 45 | 50 | 50 | Linear |
| 48 | 100 | 0 | Linear |
| 55 | 100 | 0 | Hold |

Mobile Phase A (Water:MeOH:TFA :: 95:5:0.1%, v/v/v)
Mobile Phase B (Water:MeOH:TFA :: 35:65:0.1%, v/v/v)
MeOH = Methanol
TFA = trifluoroacetic acid The synthesis and purification of S-MNTX were monitored using the above HPLC protocol. S-MNTX is distinguished from R-MNTX using the HPLC conditions described. Authentic R-MNTX for use as a standard may be made using the protocol described herein. In a typical HPLC run, S-MNTX elutes about 0.5 minutes before R-MNTX elutes. The retention time of S-MNTX is approximately 9.3 minutes; the retention time of R-MNTX is about 9.8 minutes.

Gas chromatographic (GC) analysis was performed on an HP 5890 Series II GC controlled by HP 3365 ChemStation software using the following method: GC Method:
Column: J&W Scientific DB-1, 30 m×0.53 mm, 3μ
Initial Temp: 40° C.
Initial Time: 10.00 min
Rate: 20° C./min
Final Temp: 250° C.
Final Time: 2.00 min
Injector Temp: 250° C.
Detector: Flame-Ionization Typical Alkylation Reaction. The substrate was charged to a 250-mL Parr flask along with 10 volumes alkylating agent. If dimethyl formamide (DMF) or NMP was used as a cosolvent, 2.5 volumes were added. The flask was placed in a Parr shaker (hydrogen tank closed off) and heated to the reaction temperature with shaking under pressure. Pressures typically seen during the reaction were 10-15 psi. The reaction was periodically sampled and analyzed by MS and HPLC to determine the extent of reaction and the nature of the products. At the end of the reaction, the mixture was transferred to a round-bottom flask with methanol and the volatiles removed. The residue was then chromatographed on silica gel eluting with 90:10:0.1 methylene chloride/methanol/ammonium hydroxide.

Preparation of the Ion-Exchange Column. AG 1-X8 resin (Bio-Rad, analytical grade, 100-200 mesh, chloride form) was packed into a glass column (50 mm×200 mm) and was washed with 1 N HBr (1 L, prepared with deionized (DI) water). The column was washed with DI water (approximately 10 L) until the eluent reached a pH of 6-7.

Preparation of S-MNTX. Into five, 25-mL threaded closure pressure tubes were combined oxymorphone (3.6 g, 11.9 mmol), cyclopropylmethyl iodide (17.39 g, 95.6 mmol), and N-methyl pyrrolidone (3.6 mL). The tubes were sealed with threaded Teflon caps and placed into a 6-well reactor block, preheated to 70° C. After 24 h, the reactions were visibly biphasic and HPLC analysis, sampling both solid and liquid phases, showed that the reactions proceeded to approximately 50% conversion. Heating was discontinued and the five reaction mixtures were transferred to a 1-L, round-bottom flask using methanol to transfer the mixtures and rinse the tubes. The methanol was removed under reduced pressure and the resulting NMP solution was treated with isopropyl acetate (900 mL), which resulted in both solid and oily precipitates. The oil was agitated with a spatula to afford a sticky solid. The supernatant liquid was decanted from the solid into a fluted filter paper. The solid collected in the filter paper was combined with the original solid, using methanol to aid in the recovery. The resulting solution was concentrated to a dark, viscous oil. The oil was dissolved into 20% aqueous methanol containing 0.2% HBr (20 mL) and was purified by chromatography on a Biotage Flash 75L equipped with a C18 cartridge. The fractions were analyzed by HPLC on a Luna C18(2) column (4×20 mm) and the product fractions were combined and concentrated. The resulting "purified" product dissolved into DI water (approximately 20 mL) and the chromatography was repeated with the process being repeated until the purity was enhanced to approximately 70% (AUC). The approximately 70% pure product (approximately 18 g) was dissolved into DI water (20 mL) and passed through a column of AG 1-X8 anion-exchange resin converted to the bromide form (see additional procedure) (5×25 cm). The column was eluted with DI water until no MNTX was detectable in the eluted stream. The aqueous solution was concentrated and the residue was dissolved into DI water (10 mL), which was purified by chromatography further using the Biotage Flash 75L system equipped with a C18 cartridge and eluted with 5% aqueous methanol. The fractions were analyzed by HPLC on a Luna C18(2) column(4.6×150 mm) and the product stream was partitioned into four streams based on purity (AUC); >90%, 50-90% with fast impurities, 50-90% with slow impurities, and <50%. The less-pure material was recycled through the chromatography to enhance the purity, which ultimately resulted in 3.0 g of S-MNTX that was 90% pure (AUC). The less-pure fractions were purified by chromatography further to provide approximately 1 g of 90% pure material, which was combined with 1.0 g of the 90% pure material previously isolated and purified by chromatography on a Biotage Flash 75L equipped with a C18 cartridge and eluted with 2.5% aqueous methanol. The chromatography was repeated to enhance the purity until >95% (AUC) was achieved. At the conclusion, the product streams were lyophilized from water to afford 741 mg of S-MNTX at 95.6% purity (AUC); 2.54 g of S-MNTX at 90% purity (AUC); and L08 g of S-MNTX at 79% purity (AUC).

Figure 3:
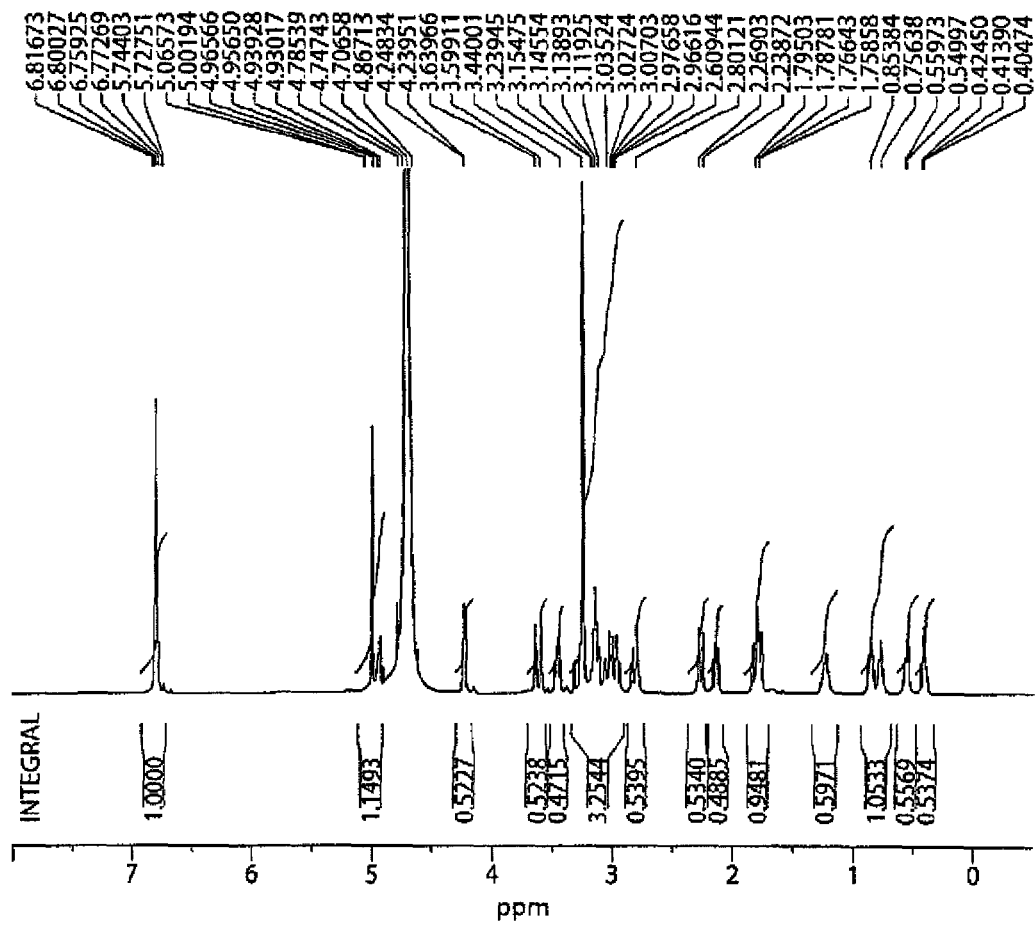
FIG. 3 provides a proton NMR spectrum of S-MNTX.
Figure 4:
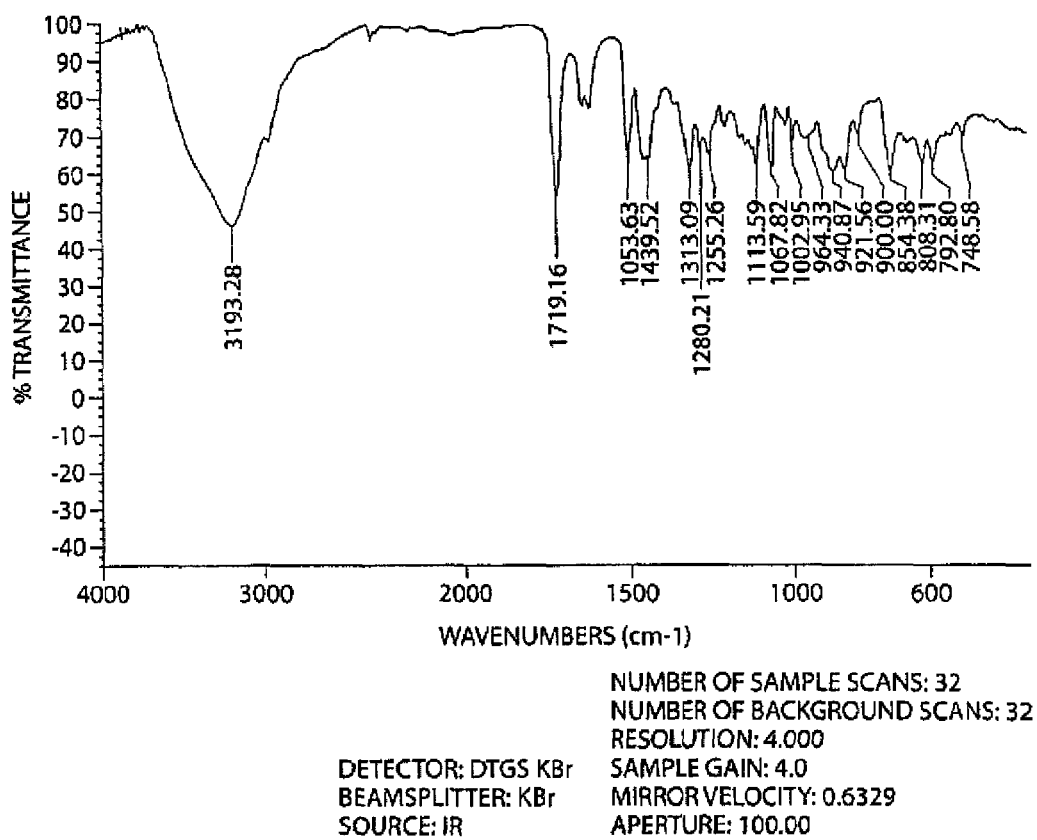
FIG. 4 provides an infrared spectrum of S-MNTX.
Figure 5:
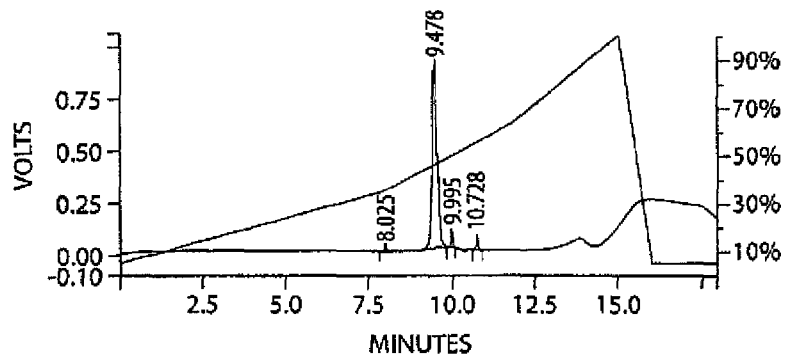
FIG. 5 provides an HPLC chromatogram of S-MNTX.
Figure 6:
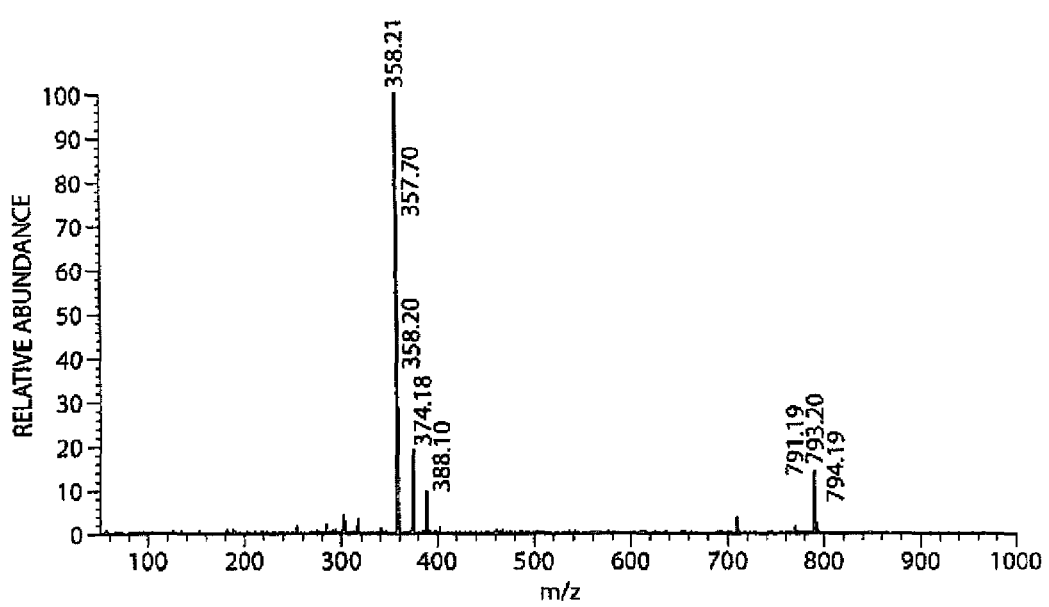
FIG. 6 provides a mass spectrogram of S-MNTX.

FIG. 3 provides a proton NMR spectrum of S-MNTX produced by this method. FIG. 4 provides an infrared spectrum of the S-MNTX product. FIG. 5 provides an HPLC chromatogram of the S-MNTX product. FIG. 6 provides a mass spectrogram of the S-MNTX product. These analytical data identify the "S" stereoisomer of MNTX at a purity of greater than 95%.

Example II

Optimization of the Synthesis and Purification of S-MNTX

Preparation of the Ion-Exchange Column. AG 1-X8 Resin (Bio-Rad, analytical grade, 100-200 mesh, chloride form, 50 wt equiv) was packed into a glass column and was washed with 1 N HBr (approximately 100 vol, prepared with DI water). The column was washed with DI water until the eluent reached a pH of 6-7.

Preparation of S-MNTX. A 250-mL, jacketed, three-neck flask was charged with oxymorphone (5.0 g, 16.6 mmol), NMP (5 mL) and copper wire (1.2 g, cut into 3-4 mm pieces). The flask was wrapped in aluminum foil and was connected to a pre-equilibrated heater/chiller set at 70° C. Cyclopropylmethyl iodide (24.16 g, 132.7 mmol) was added to the mixture and the reaction was stirred for 20 h. Analysis of a reaction aliquot by HPLC revealed a 1:1 ratio of 2:3. The reaction mixture was transferred into an Erlenmeyer flask containing IPAc (250 mL) that was vigorously stirred with an overhead mechanical stirrer. After the oily material solidified, the solid was filtered off and was transferred back into the flask; the filtrate was analyzed by HPLC and was discarded. The combined solid residues were dissolved in aqueous methanol and were filtered through a column of ion-exchange resin (Bio-Rad AG 1-X8, 50 wt equiv, converted to bromide form). The column was eluted with DI water and was rinsed until no UV active material was detected (254 nm). The resulting aqueous solution was concentrated and the residue was dissolved in IPA (5 vol) with a minimum amount of methanol to achieve solution. The solvent was stripped to remove traces of water and the resulting solid was dissolved in hot methanol (3 vol at approximately 50° C.). An ambient temperature mixture of methylene chloride/isopropyl alcohol ($CH_2Cl_2$/IPA) (6 vol/1 vol) was added and the resulting solution was allowed to stand under ambient conditions until crystallization began. The mixture was then kept in a −20° C. freezer for 2 days. The solid was collected by filtration and afforded 2.8 g of a nearly 1:1 mixture of 2 and S-MNTX. The solid was recrystallized from hot methanol (MeOH) (3 vol at approximately 50° C.) by adding $CH_2Cl_2$/IPA (6 vol/1 vol), and allowing the mixture to cool. The isolated solid (2.1 g, 29% based on weight) was found to be 94.1% pure (AUC) by HPLC analysis.

Purification of S-MNTX. The lots of S-MNTX of purity >94% (AUC) were combined and carried through the recrystallization procedure of dissolving in hot methanol (3 vol at approximately 50° C.) and then adding a $CH_2Cl_2$/IPA (6 vol/1 vol) mixture. The mixture was allowed to cool to ambient temperature and the solid was collected by filtration. Four iterations were required to improve the purity of S-MNTX from 94% to >99% and the overall mass recovery was 60%. In total, 8.80 g of S-MNTX were purified to 99.8% (AUC) as determined by HPLC analysis. The $^1$H NMR, $^{13}$C NMR, and MS spectra were consistent with the assigned structure. Karl Fischer Analysis (KF): 4.7% water; Anal. Calcd for $C_{21}H_{26}BrNO_4$: C, 57.80; H, 6.01; N, 3.21; Br, 18.31. Found: C, 54.58; H, 6.10; N, 2.82; Br, 16.37.

Example III

Opiate Receptor Binding of (S)-N-methylnaltrexone

Radioligand binding assays were conducted to determine the binding specificity of S-N-methylnaltrexone for μ-, κ-, and δ-opiate receptors using methods adapted from scientific literature (Simonin, F et al 1994, *Mol. Pharmacol* 46:1015-1021; Maguire, P. et al 1992, *Eur. J. Pharmacol.* 213:219-225; Simonin, F. et al *PNAS USA* 92(15):1431-1437; Wang, J B 1994, *FEBS Lett* 338:217-222).

S-MNTX was shown to bind human recombinant mu opioid receptors with a Ki=0.198 μM; to bind human recombinant kappa opioid receptors with Ki=1.76 μM, and did not bind to human recombinant delta opioid receptors.

Example IV

In Vitro Pharmacology of S-MNTX: μ (mu, MOP) Receptor Bioassay

Experimental Conditions. Segments of guinea pig terminal ileum were suspended in 20-ml organ baths filled with an oxygenated (95% $O_2$ and 5% $CO_2$) and pre-warmed (37° C.) physiological salt solution of the following composition (in mM): NaCl 118.0, KCl 4.7, $MgSO_4$ 1.2, $CaCl_2$ 2.5, $KH_2PO_4$ 1.2, $NaHCO_3$ 25.0 and glucose 11.0 (pH 7.4). Additional experimental conditions were as described in Hutchinson et al. (1975) Brit. J. Pharmacol., 55: 541-546.

Indomethacin (1 μM), nor-binaltorphimine (0.01 μM), methysergide (1 μM), ondansetron (10 μM) and GR1 13808 (0.1 μM) were also present throughout the experiments to prevent prostanoid release and to block the k-opioid, 5-HT2, 5-HT3 and 5-HT4 receptors, respectively. The tissues were connected to force transducers for isometric tension recordings. They were stretched to a resting tension of 1 g then allowed to equilibrate for 60 min during which time they were washed repeatedly and the tension readjusted. Thereafter, they were stimulated electrically with pulses of minimal intensity to trigger maximal contractions and 1 ms duration, delivered at 0.1 Hz by a constant current stimulator. The experiments were carried out using a semi-automated isolated organ system possessing eight organ baths, with multichannel data acquisition.

Experimental Protocols

Test for agonist activity. The tissues were exposed to a submaximal concentration of the reference agonist DAMGO (0.1 μM) to verify responsiveness and to obtain a control response. Following extensive washings and recovery of the control twitch contractions, the tissues were exposed to increasing concentrations of S-MNTX or the same agonist. The different concentrations were added cumulatively and each was left in contact with the tissues until a stable response was obtained or for a maximum of 15 min. If an agonist-like response (inhibition of twitch contractions) was obtained, the reference antagonist naloxone (0.1 μM) was tested against the highest concentration of S-MNTX to confirm the involvement of the μ receptors in this response.

Test for antagonist activity. The tissues were exposed to a submaximal concentration of the reference agonist DAMGO (0.1 μM) to obtain a control response. After stabilization of the DAMGO-induced response, increasing concentrations of S-MNTX or the reference antagonist naloxone were added cumulatively. Each concentration was left in contact with the tissues until a stable response was obtained or for a maximum of 15 min. If it occurred, an inhibition of the DAMGO-induced response by S-MNTX indicated an antagonist activity at the μ receptors.

Analysis and Expression of Results. The parameter measured was the maximum change in the amplitude of the electrically-evoked twitch contractions induced by each compound concentration. The results are expressed as a percent of the control response to DAMGO (mean values). The $EC_{50}$ value (concentration producing a half-maximum response) or $IC_{50}$ value (concentration causing a half-maximum inhibition of the response to DAMGO) were determined by linear regression analysis of the concentration-response curves.

Results. The effects of S-MNTX investigated from 1.0E−08 M to 1.0E−04 M for agonist and antagonist activities at the μ-opioid receptors in the guinea pig ileum bioassay are presented in Table IV.1 where those of the reference compounds are also reported. The $EC_{50}$ and $IC_{50}$ values determined for S-MNTX are indicated in Table IV.2.

In the field-stimulated guinea pig ileum, the μ receptor agonist DAMGO induced a concentration-dependent decrease in the twitch contraction amplitude which was reversed by the antagonist naloxone in a concentration-dependent manner.

In the untreated tissues, S-MNTX also caused a concentration-dependent and naloxone-sensitive decrease in the twitch contraction amplitude. In the tissues previously depressed with DAMGO, S-MNTX did not produce any recovery of the twitch contraction amplitude but caused a further decrease.

These results indicate that S-MNTX behaves as an agonist at the μ-opioid receptors in this tissue.

TABLE IV.1

Effects of S-MNTX evaluated for agonist and antagonist activities at the μ-opioid receptors in the guinea pig ileum Evaluation of agonist activity

| Compounds | Control response to DAMGO (1.0E−07M) | Responses to increasing concentrations of the compounds (M) | | | | | | | | | + naloxone (1.0E−07M) |
|---|---|---|---|---|---|---|---|---|---|---|---|
| | | 1.0E−08 | 3.0E−08 | 1.0E−07 | 3.0E−07 | 1.0E−06 | 3.0E−06 | 1.0E−05 | 3.0E−05 | 1.0E−04 | 1.0E−04M |
| S-MNTX | 100 | 0 | 0 | 5 | 16 | 35 | 59 | 92 | 109 | 109 | 17 |
| | | | 1.0E−09 | | | 1.0E−08 | | | 1.0E−07 | | 1.0E−07 |
| DAMGO | 100 | | 12 | | | 49 | | | 99 | | 3 |

Evaluation of antagonist activity

| Compounds | Control response to DAMGO (1.0E−07M) | Responses to DAMGO (1.0E−07M) in the presence of increasing concentrations of the compounds (M) | | | | | | | |
|---|---|---|---|---|---|---|---|---|---|
| | | 1.0E−08 | 3.0E−08 | 1.0E−07 | 3.0E−07 | 1.0E−06 | 3.0E−06 | 1.0E−05 | 3.0E−05 | 1.0E−04 |
| S-MNTX | 100 | 100 | 100 | 100 | 100 | 100 | 100 | 102 | 105 | 109 | 110 |
| | | | 5.0E−09 | | | 2.0E−08 | | | 1.0E−07 | | |
| naloxone | 100 | | 83 | | | 43 | | | −7 | | |

The results are expressed as a percent of the control response to DAMGO (decrease in twitch contraction amplitude)
(mean values; n = 2)

TABLE IV. 2

$EC_{50}$ and $IC_{50}$ values determined for S-MNTX at the μ-opioid receptors in the guinea pig ileum

| Compound | Agonist activity $EC_{50}$ value | Antagonist activity $IC_{50}$ value |
|---|---|---|
| S-MNTX | 2.0E−06 M | No antagonist activity |

Example V

Effect of S-N-Methylnaltrexone on Gastrointestinal Transit in Rats

The effect of S-N-methylnaltrexone (purity-99.81% S-N-methylnaltrexone; 0.19% oxymorphone; no detectable R-MNTX), as well as an authentic source of R-MNTX (purity 99.9%), on morphine-induced inhibition of gastrointestinal transit in rats was determined using methods described in A. F. Green, *Br. J. Pharmacol.* 14: 26-34, 1959; L. B. Witkin, C. F. et al *J. Pharmacol. Exptl. Therap.* 133: 400-408, 1961; D. E. Gmerek, et al *J. Pharmacol. Exptl. Ther.* 236: 8-13, 1986; and O. Yamamoto et al *Neurogastroenterol. Motil.* 10: 523-532, 1998.

S-MNTX or R-MNTX was administered subcutaneously to rats (Crl: CD®(SD)BR; 5-8 wks old; 180-250 gms wt) at concentrations of 1.0, 3.0, or 10.0 mg/kg. A control group of rats received 2 mL/kg of a 0.9% saline solution (n=10). After 15 minutes, rats were subcutaneously injected with saline (1 mL/kg) or morphine (3 mg/kg). A 10% suspension of activated charcoal in 0.25% methylcellulose was administered orally at 10 mL/kg to the rats 20 minutes (±2 minutes) after the subcutaneous dose of morphine or saline. The rats were euthanized 25 minutes (±3 minutes) after receiving the charcoal and the intestines were removed and lightly stretched on moist paper along a meterstick. The small intestine from pyloric sphincter to caecum was measured and the distance traveled by the charcoal as a fraction of that length was evaluated for each rat.

Statistically significant effects were determined by ANOVA with Tukey HSD Multiple Comparison Test. Differences with p values <0.05 were considered statistically significant.

Values for charcoal motility were expressed as a percent effect and were calculated in the following manner: The individual distance traveled by the charcoal in centimeters was divided by the total length of the intestines in centimeters (pyloric sphincter to caecum) for each rat. Mean values were calculated for each group, and the percent effect was calculated using the following formula:

$$\% \text{ Effect} = \frac{(\text{Mean value for controls}) - (\text{Mean value for treated})}{\text{Mean value for controls}} \times 100$$

Results

The results from the GI transit study are shown in Table 1. Morphine, known to affect both central and peripheral opioid receptors, decreased GI motility as reported in the literature. R-MNTX, a peripherally selective mu opioid receptor antagonist, had no effect on GI transit when administered alone. R-MNTX administered prior to morphine reversed the GI slowing effect of morphine as would be expected from an opioid antagonist. The antagonist activity of R-MNTX on morphine was dose-dependent, with a partial reversal at 1 mg/kg and reversal at 3 or 10 mg/kg to the degree that GI transit was returned to values that were not statistically significantly different from the control value. In contrast to the antagonist activity of R-MNTX, S-MNTX had agonist activity when used alone, i.e. it resulted in decreased GI motility as reflected in a statistically significantly decrease in GI transit. The agonist activity of S-MNTX in decreasing GI motility was even more pronounced using S-MNTX and morphine in combination. The combination of S-MNTX+morphine had a dramatic synergistic agonist effect in decreasing GI motility to levels not observed using either compound alone. The agonist activity of S-MNTX was manifested as a slowing of GI transit when it was administered by itself and also by the increase in the inhibitory effect of morphine when the two agents were used in combination.

TABLE 1

Effect of S-MNTX on GI Motility

| Treatment | Mean Motility | Percent Decrease |
| --- | --- | --- |
| Saline + Saline | 0.606 | — |
| Saline + Morphine | 0.407* | 33% |
| R-MNTX 10 mg/kg + Saline | 0.572 | 6% |
| R-MNTX 1 mg/kg + Morphine | 0.463* | 24% |
| R-MNTX 3 mg/kg + Morphine | 0.558 | 8% |
| R-MNTX 10 mg/kg + Morphine | 0.557 | 8% |
| S-MNTX 10 mg/kg + Saline | 0.476* | 21% |
| S-MNTX 1 mg/kg + Morphine | 0.281* | 54% |
| S-MNTX 3 mg/kg + Morphine | 0.258* | 57% |
| S-MNTX 10 mg/kg + Morphine | 0.122* | 80% |

Route—sc
Morphine dose = 3 mg/kg
Mean Motility—ratio of length of charcoal transit/total intestine length
*Statistically significant (p < 0.05) change when compared to the vehicle group Example VI Tests for Anti-Diarrheal Activity (a) Castor Oil Test in Rats [see, e.g., Niemegeers et al. (1972) *Arzneim Forsch* 22:516-518; U.S. Pat. Nos. 4,867,979; 4,990,521; 4,824,853]

Rats are fasted overnight. Each animal is treated intravenously with the desired dose of the compound to be tested. One hour thereafter, the animal receives 1 ml of castor oil orally. Each animal is kept in an individual cage and about 2 hours after the castor oil treatment, each animal is assessed for the presence or absence of diarrhea. The $ED_{50}$ value is determined as that dose in mg/kg body weight at which no diarrhea is present in 50% of the tested animals.

For example, young female Wistar rats (230-250 g body weight) are fasted to overnight and in the morning each animal is treated orally with a dose level of the compound to be tested. One hour thereafter, the animal receives 1 ml of castor oil orally. Each animal is kept in an individual cage. At different selected time intervals (e.g., 1, 2, 3, 4, 6 and 8 hrs) after the castor oil treatment, the presence or absence of diarrhea is noted. In more than 95% of 500 control animals, severe diarrhea is observed 1 hour after treatment with castor oil. Using this all-or-none criterion, a significant positive effect occurs with the tested compound if no diarrhea is observed 1 hour after the castor oil treatment. A minimum of 5 dose levels are used per drug, each dose level being given to 10 rats on ten different days. The $ED_{50}$ value, i.e., the dose level at which such effect is observed in 50% of the animals, for the compounds, such as the compounds of formula (II), generally ranges from about 0.01 to about 10 mg/kg.

(b) Castor Oil Test in Mice [See, e.g., U.S. Pat. No. 4,326,075]

Groups of mice are orally dosed with test compound and one-half hour later all mice are given 0.3 ml of castor oil. Three hours after castor oil administration, all of the mice are checked for diarrhea and the dose of testing compound which protected 50% of the mice from diarrhea is the $ED_{50}$ dose.

(c) Ricinus Oil Test [See, e.g., U.S. Pat. No. 4,990,521]

Rats, such as female Wistar rats or other laboratory strains, are fasted overnight. Each animal is treated orally with a dose level of the test compound. One hour thereafter, the animal is given an amount, typically 1 ml, of ricinus oil orally, each animal is kept in an individual cage and 1 hour after the ricinus oil treatment, the presence or absence of diarrhea is noted. The $ED_{50}$ value is determined as that dose in mg/kg body weight at which no diarrhea is present in 50% of the treated animals.

(d) Antagonism of $PGE_2$-induced Diarrhea in Mice

Anti-diarrheal activity can be determined by assessing the effects of a compound as an antagonist of $PGE_2$-induced diarrhea in mice [see, e.g., Dajani et al. 1975) *European Jour. Pharmacol.* 34:105-113; and Dajani et al. (1977) *J. Pharmacol. Exp. Ther.* 203:512-526; see, e.g., U.S. Pat. No. 4,870,084]. This method reliably elicits diarrhea in otherwise untreated mice within 15 minutes. Animals that are pretreated with the test agent in which no diarrhea occurs are considered protected by the test agent. The constipating effects of test agents are measured as an "all or none" response, and diarrhea is defined as watery unformed stools, very different from normal fecal matter, which has well-formed boluses, and is firm and relatively dry.

Standard laboratory mice, such as albino mice of the Charles River CD-1 strain, are used. They are typically kept in group cages. The weight range of the animals when tested is between 20-25 g. Pelleted rat chow is available ad libitum until 18 hours prior to testing, at which time food is withdrawn. Animals are weighed and marked for identification. Five animals are normally used in each drug treatment group and compared with controls. Mice weighing 20-25 g are housed in group cages, and fasted overnight prior to testing. Water is available. Animals are challenged with $PGE_2$ [0.32 mg/kg i.p. in 5% ETOH] one hour after test drug treatment, and immediately placed individually, for example, in transparent acrylic boxes. A disposable cardboard sheet on the bottom of the box is checked for diarrhea on an all or nothing basis at the end of 15 minutes.

Example VII

Analgesic Activity of S-MNTX in Pain Models

The following pain models are useful in determining the analgesic activity of S-MNTX.

1. Acetic Acid Writhing Assay in Mice

Mice (CD-1, male) are weighed and placed in individual squares. The test or control article are administered and after the appropriate absorption time, acetic acid solution are administered intraperitoneally. Ten minutes after the i.p. injection of acetic acid, the number of writhes are recorded for a period of 5 minutes.

The total number of writhes for each mouse are recorded. The mean number of writhes for the control and each test article group are compared using an ANOVA followed by a relevant multiple comparison test and percent inhibition calculated.

2. Phenylquinone (PPQ) Writhing Assay

Mice (CD-1, male) are weighed and placed in individual squares. The test or control article are administered and after the appropriate absorption time, the PPQ solution (0.02% aqueous solution) is administered intraperitoneally. Each animal is observed closely for ten minutes for exhibition of writhing.

The total number of writhes for each mouse are recorded. The mean number of writhes for the control and each test article group are compared using an ANOVA followed by a relevant multiple comparison test and percent inhibition calculated.

3. Randall-Selitto Assay in Rats

The purpose of this assay is to determine the effect of test articles upon the pain threshold of rats.

Following an overnight fast, rats are placed in groups of ten. Twenty rats are used as vehicle controls. The rats are then sequentially injected with a 20% Brewer's yeast suspension into the plantar surface of the left hind paw. Two hours later the rats are administered the test article, reference drug, or control vehicle. One hour after dose administration, the pain threshold of the inflamed and non-inflamed paw is measured by a "Analgesia Meter" that exerts a force which increases at a constant rate along a linear scale.

The control group threshold and standard deviation for the inflamed paw and non-inflamed paw are calculated. Rats in the test article group and reference group are considered protected if the individual pain threshold exceeds the control group mean threshold by two standard deviations of the means.

4. Hot Plate Analgesia Assay

Each mouse (CD-1, male) serves as its own control throughout the experiment. The mice are placed sequentially on a Hot Plate Analgesia Meter (set for 55° C.±2° C.). The mice react characteristically to the heat stimulus by:

1. Licking the forepaw
2. Rapid fanning of the hind paw
3. A sudden jump off the hot plate Any of the three types of reactions are taken as an end point to the heat stimulus. The mouse is removed from the hot plate immediately upon displaying the end point. The reaction time is measured quantitatively by the number of seconds that elapse between the placing of the mouse on the hot plate and the display of a definitive end point. Elapsed time is measured by a stop watch accurate to at least ⅕ of a second. Only mice whose control reaction time is 10.0 seconds or less are used. At 15, 30, 60 and 120 minutes (±1 to 5 minutes) after test or control article administration, reaction times will be obtained and recorded for the group sequentially.

Analgesic response is an increase in reaction time of the mouse to the heat stimulus. Percent analgesia is calculated from the average response of the group of ten mice per dose level at a specified time interval:

$$\% \text{ analgesia} = \frac{\text{average response time in seconds (test article treated)}}{\text{average response time in seconds (control)}} - 1.0 \times 100$$

An ANOVA with appropriate Multiple Comparison Test is then performed.

5. Rat Tail Radiant Heat Test (Tail Flick)

To evaluate the potential ability of a test article to produce an analgesic response to thermal stimulation in rats.

Following an overnight fast, rats are weighed and placed in groups of ten. The test or vehicle control articles are administered. A Tail Flick Analgesia Meter is used. Sixty minutes following oral administration (or as recommended by the Sponsor), the tail of each rat is exposed to a specific intensity of heat stimulus and the time required to elicit a response (a characteristic tail flick) is recorded.

Percent analgesia will be calculated using the mean control response compared to the mean test article response.

Example VIII

Identification of Compounds for Use as Peripheral Anti-Hyperalgesics

In general, the methods described above, are also useful for assessing peripheral anti-hyperalgesic activities of test compounds. Most preferred among the methods for assessing anti-hyperalgesic activity are those described in Niemegeers et al. (1974) *Drug Res.* 24:1633-1636.

1. Assessment of Ratio [C] of the $ED_{50}$ Value [A] in a Test for Anti-diarrheal Activity, Such as the Castor Oil Test, to the $ED_{50}$ Value [B] in a Test of CNS Effects, Such as the Tail Withdrawal Test The agents intended for use in the methods and compositions can be identified by their activity as anti-diarrheals, and their lack of CNS effects. In particular, the selected compound exhibits anti-hyperalgesic activity in any of the standard models, discussed above, and, preferably, either (a) the ratio of these activities [B/A], as measured in standard assays, is substantially greater or equal to [at least equal to, more preferably at least about 2-fold greater] than the ratio of such activities for diphenoxylate; or (b) the activity of the compound in an assay that measures CNS activity is substantially less [at least two-fold, preferably 3-fold or more] than diphenoxylate.

Example IX

In Vitro Pharmacology of S-MNTX: cAMP Assay in CHO Cells Expressing Human μ (Mu, MOP) Receptor The mu opioid receptor is $G_i$ coupled, which works by inhibiting a cAMP increase. Thus in these experiments, cellular cAMP was increased by addition of 10 μM forskolin. Prior addition of DAMGO, or similar agonists, e.g. endomorphin-1, fentanyl, or morphine, inhibited this forskolin-induced increase. The absence of agonist effect, produced a result equivalent to forskolin alone. Therefore, increasing agonist concentration decreased cAMP levels.

Antagonists, such as CTOP, naloxone and ciprodime inhibited the cAMP inhibition. Thus full antagonist effect was equivalent to forskolin without any addition of μ-opioid agonist. In these experiments, antagonist was added, then 30 μM DAMGO, then forskolin. Therefore, increasing antagonist concentration increased cAMP.

Experimental Protocol
Assay Characteristics:
EC50 (DAMGO): 12 nM
cAMP production
(with forskolin & IBMX): 3.4 pmol/well
Inhibition (10 uM DAMGO): 90%
Materials and Methods:
Cell Source: Human recombinant/CHO cells
Reference Agonist: DAMGO
Reference Inhibitor: CTOP (see antagonist SAP)
Reference Curve: DAMGO (cell activation)
cAMP (EIA control curve)
Cells were grown to confluence in 96-well plates. Cells were washed and equilibrated in physiological buffer before analysis. 20 ul of drug, 100 uM IBMX and 10uM forskolin were added and incubated for 25 minutes at room temperature and then the reaction was stopped with the addition of 0.1 N HCl. Extracted cAMP level was determined via competitive EIA assay utilizing alkaline phosphatase. Additional experimental conditions were as described in Toll L., J Pharmacol Exp Ther. (1995) to 273(2): 721-7.

Results

Agonist Assay: S-MNTX demonstrated an agonist response with EC50 of 600 nM. (6.0E-7M) as shown in Table IX.1. The agonist response was complete (not partial).

TABLE IX.1

| log {M} conc | S-MNTX | SD | DAMGO | SD |
|---|---|---|---|---|
| −4.0 | 3 | 6 | −1 | 3 |
| −4.5 | −3 | 1 | | |
| −5.0 | 4 | 9 | 2 | 5 |
| −5.5 | 11 | 6 | | |
| −6.0 | 32 | 7 | 1 | 6 |
| −6.5 | 66 | 21 | | |
| −7.0 | 70 | 17 | 2 | 6 |
| −7.5 | 79 | 24 | | |
| −8.0 | 104 | 10 | 68 | 28 |
| −9.0 | 86 | 5 | 63 | 10 |
| −10.0 | | | 88 | 22 |
| −11.0 | | | 105 | 13 |

Antagonist Assay: S-MNTX showed no antagonist effect, as it is demonstrated by the results presented in Table X.2.

TABLE IX. 2

| log {M} conc | S-MNTX | Range | CTOP | Range |
|---|---|---|---|---|
| −4.0 | −13 | 5 | | |
| −4.5 | −13 | 1 | | |
| −5.0 | −9 | 3 | 91 | 11 |
| −5.5 | −8 | 7 | | |
| −6.0 | −1 | 17 | 109 | 11 |
| −6.5 | 9 | 1 | | |
| −7.0 | 5 | 7 | 48 | 3 |
| −7.5 | 6 | 7 | | |
| −8.0 | 4 | 6 | 1 | 1 |
| −9.0 | 0 | 4 | | |
| −10.0 | | | | |
| −11.0 | | | −1 | 1 |

The disclosures of all patents, patent applications and scientific publications cited or referenced herein are incorporated by reference in their entirety, including U.S. Pat. No. 7,674,904, issued Mar. 9, 2010, titled: "SYNTHESIS OF (R)-N-METHYLNALTREXONE". In case of conflict between documents incorporated by reference and the instant application the instant application will control.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An isolated compound of the S configuration with respect to nitrogen of Formula I:

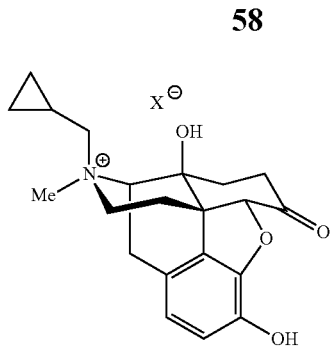

having at least 50% purity, and wherein X is a counterion.

2. The isolated compound of claim 1, wherein the counterion is a halide, bromide, iodide, sulfate, phosphate, nitrate, or anionic-charged organic species.

3. The isolated compound of claim 1, having at least 60% or 70% purity.

4. A composition comprising MNTX, wherein the MNTX present in the composition is greater than 50% in S configuration with respect to nitrogen.

5. The composition of claim 4, wherein the MNTX has a counterion that is a halide, iodide, bromide, sulfate, phosphate, nitrate, or anionic-charged organic species.

6. The composition of claim 4, wherein the composition is a solution or a solid.

7. A pharmaceutical composition comprising an effective amount of the composition of claim 4, and a pharmaceutically acceptable carrier.

8. The pharmaceutical composition of claim 7, further comprising an agent selected from the group consisting of an opioid, opioid agonist, opioid antagonist, antiviral agent, an antibiotic agent, an antifungal agent, an antibacterial agent, an antiseptic agent, an anti-protozoal agent, an anti-parasitic agent, an anti-inflammatory agent, a vasoconstrictor agent, a local anesthetic agent, an anti-diarrheal agent, an anti-hyperalgesia agent, a non-opioid pain relieving agent, an anti-infective agent, an anti-histamine, and an irritable bowel syndrome therapeutic agent.

9. A method for inhibiting diarrhea in a subject comprising administering to a subject in need of such treatment the pharmaceutical composition of claim 7 in an amount effective to treat or prevent the diarrhea.

10. A method of reducing a rate or a volume of discharge from an ileostomy or colostomy in a subject comprising administering to the subject in need of such reduction the pharmaceutical composition of claim 7 in an amount effective to reduce the rate or volume of discharge from the ileostomy or colostomy.

11. A method for inhibiting gastrointestinal motility in a subject in need of such treatment comprising administering to the subject the pharmaceutical composition of claim 7 in an amount effective to inhibit gastrointestinal motility in the subject.

12. A method for treating irritable bowel syndrome comprising administering to a patient in need of such treatment the pharmaceutical composition of claim 7 in an amount effective to ameliorate at least one symptom of the irritable bowel syndrome.

13. A method for inhibiting pain in a subject comprising administering the pharmaceutical composition of claim 7 in an amount sufficient to prevent or treat the pain.

14. A method for inhibiting inflammation in a subject comprising administering to a subject in need thereof the pharmaceutical composition of claim 7 in an amount effective to inhibit the inflammation.

15. A method of inhibiting production of tumor necrosis factor (TNF) in a subject, comprising administering to the subject a composition comprising a TNF production-inhibitory amount of the pharmaceutical composition of claim 7.

16. A method for inhibiting gastrointestinal function comprising administering to a subject in need thereof the pharmaceutical composition of claim 7, and administering to the subject a peripheral mu opioid antagonist.

17. A method for manufacturing S-MNTX comprising the following steps, (a) obtaining a first composition containing S-MNTX, (b) purifying the first composition by chromatography, recrystallization or a combination thereof, (c) conducting HPLC on a sample of purified first composition using S-MNTX as a standard, (d) determining the presence or absence of R-MNTX in the sample.

18. The isolated compound of claim 2, wherein the counterion is a halide.

19. The isolated compound of claim 18, wherein the halide is bromide.

20. The isolated compound of claim 18, wherein the halide is iodide.

21. The isolated compound of claim 1, wherein the isolated compound is in a crystal form.

22. The composition of claim 5, wherein the counterion is a halide.

23. The composition of claim 22, wherein the halide is bromide.

24. The composition of claim 22, wherein the halide is iodide.

25. The pharmaceutical composition of claim 7, wherein the composition is in a controlled release or sustained release formulation.

26. The pharmaceutical composition of claim 7, wherein the composition is a solution, a topical formulation, a suppository or is lyophilized.

27. An inhaler containing the pharmaceutical composition of claim 7.

28. A nasal spray device containing the pharmaceutical composition of claim 7.

29. The method of claim 13, wherein the pain is peripheral hyperalgesia.

* * * * *